United States Patent
Ruppersberg et al.

(10) Patent No.: US 9,931,021 B2
(45) Date of Patent: Apr. 3, 2018

(54) METHOD FOR IDENTIFYING OBJECTS IN A SUBJECT'S EAR

(71) Applicant: Helen of Troy Limited, Belleville (BB)

(72) Inventors: Peter Ruppersberg, Blonay (CH); Albrecht Lepple-Wienhues, Pontarlier (FR)

(73) Assignee: HELEN OF TROY LIMITED, Bellevile (BB)

( * ) Notice: Subject to any disclaimer, the term of this patent is extended or adjusted under 35 U.S.C. 154(b) by 89 days.

(21) Appl. No.: 14/762,435

(22) PCT Filed: Feb. 4, 2014

(86) PCT No.: PCT/EP2014/000293
§ 371 (c)(1),
(2) Date: Jul. 21, 2015

(87) PCT Pub. No.: WO2014/117954
PCT Pub. Date: Aug. 7, 2014

(65) Prior Publication Data
US 2015/0351606 A1    Dec. 10, 2015

Related U.S. Application Data

(60) Provisional application No. 61/809,048, filed on Apr. 5, 2013, provisional application No. 61/760,511, filed
(Continued)

(30) Foreign Application Priority Data

Feb. 4, 2013 (EP) .................................... 13000552
Feb. 4, 2013 (EP) .................................... 13000553
Apr. 5, 2013 (EP) .................................... 13001748

(51) Int. Cl.
*A61B 1/267* (2006.01)
*A61B 1/00* (2006.01)
(Continued)

(52) U.S. Cl.
CPC ...... *A61B 1/00142* (2013.01); *A61B 1/00009* (2013.01); *A61B 1/00057* (2013.01);
(Continued)

(58) Field of Classification Search
CPC ....... A61B 5/00; A61B 5/0059; A61B 5/0062; A61B 5/0068
(Continued)

(56) References Cited

U.S. PATENT DOCUMENTS 4,366,811 A    1/1983    Riester
4,380,998 A    4/1983    Kieffer, III et al.
(Continued)

FOREIGN PATENT DOCUMENTS

CN    1829468 A    9/2006
CN    102026574 A    4/2011
(Continued)

OTHER PUBLICATIONS

Salvinelli, F., et al., "The External Ear and the Tympanic Membrane—A Three-Dimensional Study," *Scandinavian Audiology* 20(4):253-256, 1991.
(Continued)

*Primary Examiner* — Ellen C Hammond
*Assistant Examiner* — Christina Negrellirodriguez
(74) *Attorney, Agent, or Firm* — Seed Intellectual Property Law Group LLP

(57) ABSTRACT

A method of identifying objects in a subject's ear, comprising the following steps: introducing an optical electronic imaging unit and a light source into an ear canal of a subject's outer ear, wherein the electronic imaging unit exhibits an optical axis directed in a distal direction, especially directed at the eardrum of the subject's ear; using the electronic imaging unit to capture an image from an eccentric observation point positioned on the optical axis and
(Continued)

positioned eccentrically within the ear canal; and determining brightness or color information to identify objects shown in the image by electronic means, in order to automatically identify the objects, especially the eardrum.

42 Claims, 16 Drawing Sheets

Related U.S. Application Data on Feb. 4, 2013, provisional application No. 61/760,507, filed on Feb. 4, 2013.

(51) Int. Cl.
| | | |
|---|---|---|
| A61B 1/07 | (2006.01) | |
| A61B 1/06 | (2006.01) | |
| A61B 5/01 | (2006.01) | |
| A61B 5/00 | (2006.01) | |
| A61B 1/227 | (2006.01) | |
| A61B 5/11 | (2006.01) | |
| A61B 1/05 | (2006.01) | |
| A61B 5/107 | (2006.01) | |

(52) U.S. Cl.
CPC ...... *A61B 1/00066* (2013.01); *A61B 1/00101* (2013.01); *A61B 1/00179* (2013.01); *A61B 1/05* (2013.01); *A61B 1/051* (2013.01); *A61B 1/0623* (2013.01); *A61B 1/0638* (2013.01); *A61B 1/0676* (2013.01); *A61B 1/0684* (2013.01); *A61B 1/07* (2013.01); *A61B 1/227* (2013.01); *A61B 1/2275* (2013.01); *A61B 5/0075* (2013.01); *A61B 5/0086* (2013.01); *A61B 5/01* (2013.01); *A61B 5/1077* (2013.01); *A61B 5/11* (2013.01); *A61B 5/6817* (2013.01); *A61B 5/7203* (2013.01); *A61B 5/7221* (2013.01); *A61B 5/7246* (2013.01); *A61B 5/7264* (2013.01); *A61B 5/7275* (2013.01); *A61B 5/74* (2013.01); *A61B 2562/0242* (2013.01)

(58) Field of Classification Search
USPC ................. 600/476–478, 199, 200
See application file for complete search history.

(56) References Cited

U.S. PATENT DOCUMENTS

| | | | |
|---|---|---|---|
| 4,685,452 A | 8/1987 | Riester | |
| 4,766,886 A | 8/1988 | Juhn | |
| 5,363,839 A * | 11/1994 | Lankford | A61B 1/04 600/112 |
| 5,868,682 A | 2/1999 | Combs et al. | |
| 5,919,130 A | 7/1999 | Monroe et al. | |
| 5,935,058 A | 8/1999 | Makita et al. | |
| 5,951,486 A | 9/1999 | Jenkins et al. | |
| 6,165,035 A | 12/2000 | Avner | |
| 6,898,457 B1 | 5/2005 | Kraus et al. | |
| 7,529,577 B2 | 5/2009 | Jensen et al. | |
| 2002/0087084 A1 | 7/2002 | Shahar et al. | |
| 2003/0108083 A1 | 6/2003 | Seitz | |
| 2003/0139672 A1 | 7/2003 | Cane et al. | |
| 2004/0136010 A1 | 7/2004 | Jensen et al. | |
| 2004/0158157 A1* | 8/2004 | Jensen | A61B 1/227 600/476 |
| 2005/0027168 A1 | 2/2005 | Strom et al. | |
| 2005/0192482 A1 | 9/2005 | Carpenter et al. | |
| 2005/0228231 A1 | 10/2005 | MacKinnon et al. | |
| 2008/0249369 A1 | 10/2008 | Seibel et al. | |
| 2009/0030295 A1 | 1/2009 | Shioi et al. | |
| 2009/0182526 A1 | 7/2009 | Quinn et al. | |
| 2010/0060718 A1 | 3/2010 | Forster et al. | |
| 2011/0063428 A1 | 3/2011 | Sonnenschein et al. | |
| 2011/0112791 A1 | 5/2011 | Pak et al. | |
| 2011/0137118 A1 | 6/2011 | Huang | |
| 2011/0257481 A1 | 10/2011 | Ogawa et al. | |
| 2012/0059224 A1 | 3/2012 | Wellen et al. | |
| 2012/0130168 A1 | 5/2012 | Konomura | |
| 2012/0179187 A1 | 7/2012 | Loushin et al. | |
| 2012/0253166 A1 | 10/2012 | Ahn et al. | |
| 2012/0327426 A1 | 12/2012 | Hart et al. | |
| 2013/0027515 A1 | 1/2013 | Vinther et al. | |
| 2013/0083823 A1 | 4/2013 | Harr et al. | |
| 2013/0237754 A1 | 9/2013 | Berglund et al. | |
| 2013/0296685 A1 | 11/2013 | Tsuboi et al. | |
| 2015/0351607 A1 | 12/2015 | Ruppersberg et al. | |
| 2015/0351616 A1 | 12/2015 | Ruppersberg et al. | |
| 2015/0351620 A1 | 12/2015 | Ruppersberg et al. | |
| 2015/0351637 A1 | 12/2015 | Ruppersberg et al. | |
| 2015/0374208 A1 | 12/2015 | Ruppersberg et al. | |

FOREIGN PATENT DOCUMENTS

| | | |
|---|---|---|
| EP | 0 472 490 A1 | 2/1992 |
| EP | 1 134 565 A1 | 9/2001 |
| EP | 1 477 107 B1 | 8/2007 |
| EP | 2 277 439 A2 | 1/2011 |
| EP | 2 289 391 A1 | 3/2011 |
| EP | 2 014 220 B1 | 12/2012 |
| JP | 63-40117 A | 2/1988 |
| JP | 5-253184 A | 10/1993 |
| JP | 7-111987 A | 5/1995 |
| JP | 9-19403 A | 1/1997 |
| JP | 11-28194 A | 2/1999 |
| JP | 11-113841 A | 4/1999 |
| JP | 11-316157 A | 11/1999 |
| JP | 2000-30063 A | 1/2000 |
| JP | 2001-517105 A | 10/2001 |
| JP | 2002-135887 A | 5/2002 |
| JP | 2002-528158 A | 9/2002 |
| JP | 2004-535834 A | 12/2004 |
| JP | 2005-519666 A | 7/2005 |
| JP | 2007-130084 A | 5/2007 |
| JP | 2007-144103 A | 6/2007 |
| JP | 2007-236734 A | 9/2007 |
| JP | 2009-153664 A | 7/2009 |
| JP | 2009-178482 A | 8/2009 |
| JP | 2009-201853 A | 9/2009 |
| JP | 2011-62370 A | 3/2011 |
| JP | 2011-72683 A | 4/2011 |
| JP | 2011-104333 A | 6/2011 |
| JP | 2011-520501 A | 7/2011 |
| JP | 2012-514200 A | 6/2012 |
| JP | 3178405 U | 8/2012 |
| JP | 2013-202260 A | 10/2013 |
| JP | 2014-525774 A | 10/2014 |
| JP | 2015-530886 A | 10/2015 |
| KR | 10-2006-0122567 A | 11/2006 |
| TW | 201225896 A1 | 7/2012 |
| WO | 02/39874 A2 | 5/2002 |
| WO | 2007-049562 A1 | 5/2007 |
| WO | 2009/139548 A2 | 11/2009 |
| WO | 2009/157825 A1 | 12/2009 |
| WO | 2012/061697 A1 | 5/2012 |
| WO | 2013/002935 A1 | 1/2013 |
| WO | 2013/016651 A1 | 1/2013 |

OTHER PUBLICATIONS

Wäny, M., et al., "Utrasmall Digital Image Sensor for Endoscopic Applications," in *Proc. of 2009 International Image Sensor Workshop*, Bergen, Norway, Jun. 22-28, 2009, 4 pages.

Wilke, M., et al., "Prospects and Limits in Wafer-Level-Packaging of Image Sensors," Electronic Components and Technology Conference (ECTC), 2011 IEEE 61st, Lake Buena Vista, Florida, May 31-Jun. 3, 2011, pp. 1901-1907.

* cited by examiner

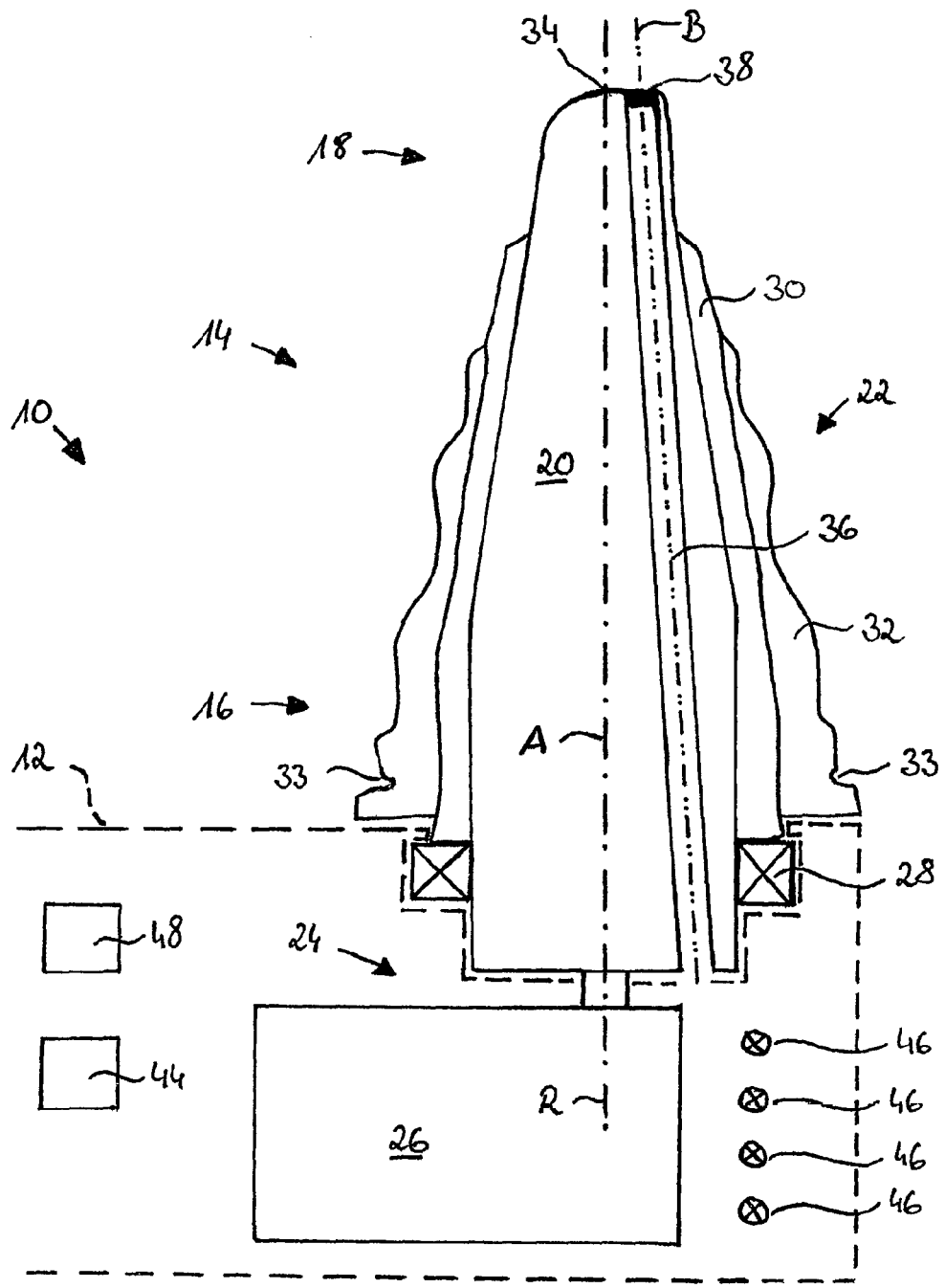
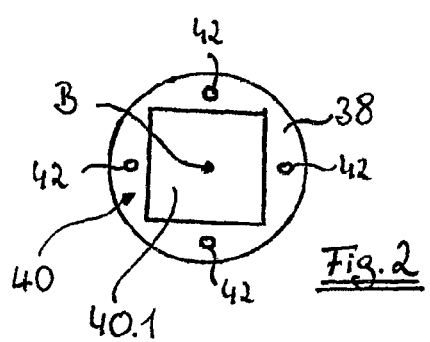
Fig. 1
Fig. 2

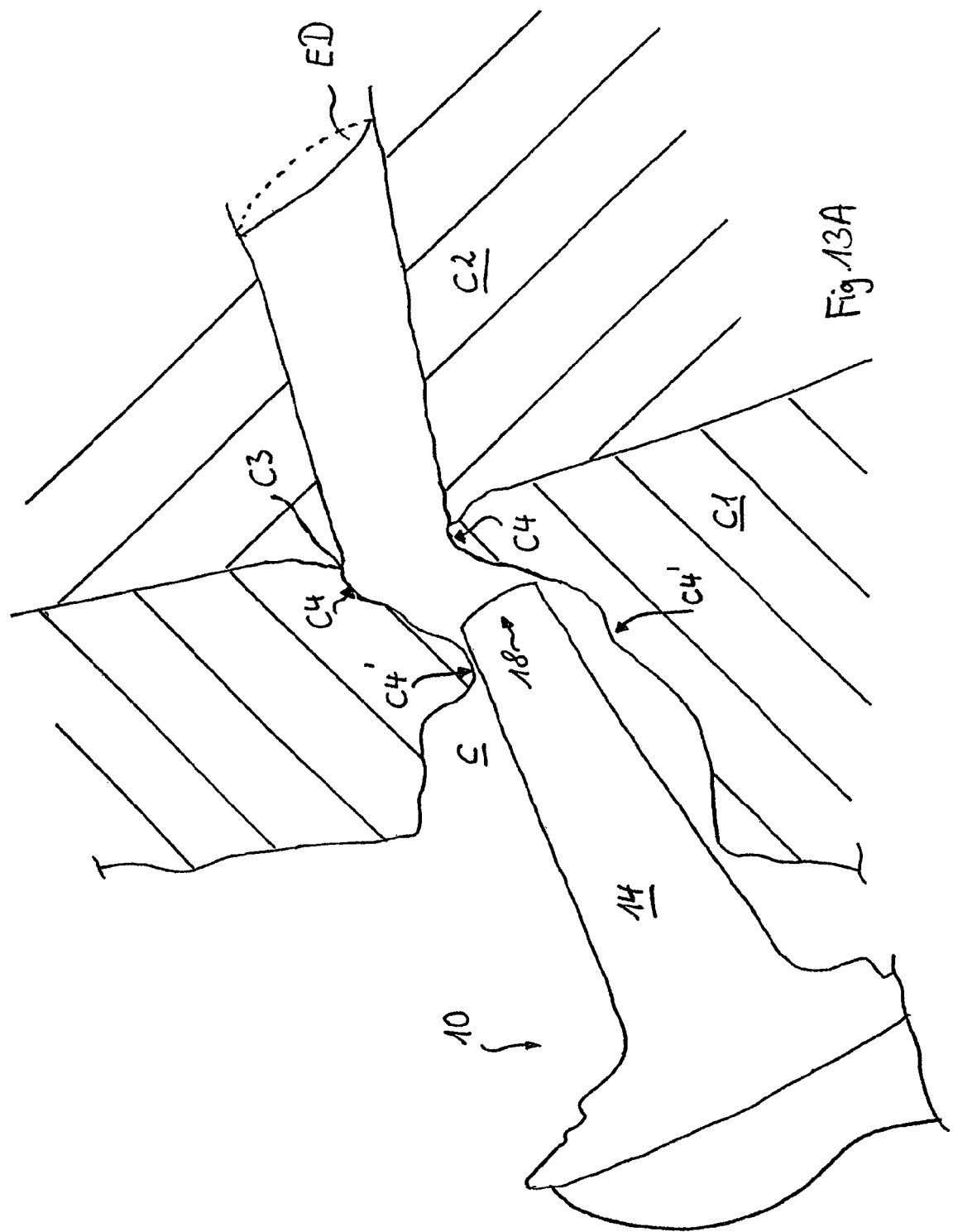

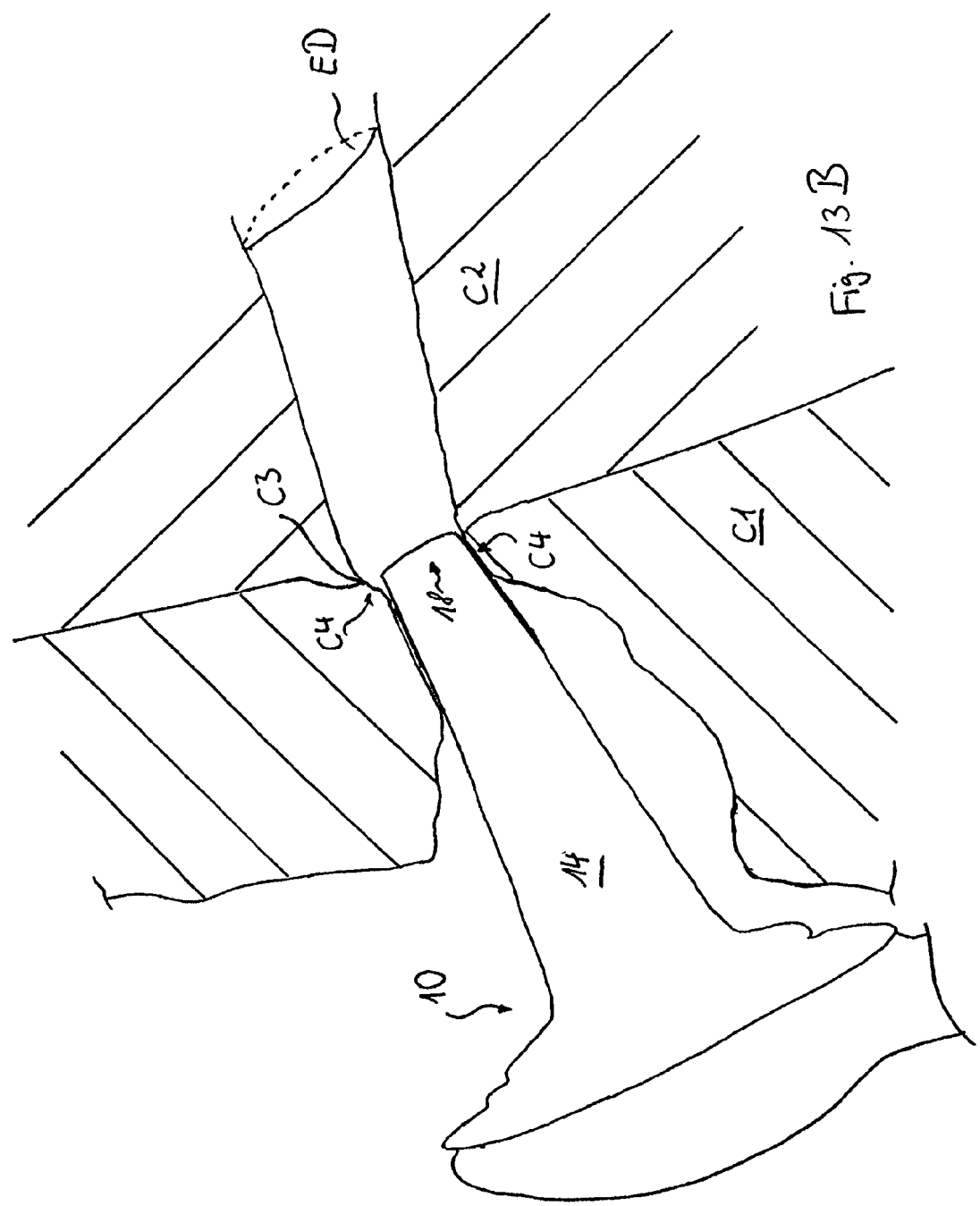

METHOD FOR IDENTIFYING OBJECTS IN A SUBJECT'S EAR

FIELD OF THE INVENTION

The invention refers to a method of identifying objects in a subject's ear. Looking into ears is called "otoscopy". Otoscopy is a standard medical examination technique established more than 100 years ago. Medical students learn otoscopy early in their studies during the practical course in physiology. Otoscopic examination assists the skilled physician in examining the ear canal or eardrum which may be affected e.g. by otitis media (OM), otitis media with effusion (OME), otitis externa, and eardrum perforation. OME is defined by the presence of middle ear effusion, i.e. a liquid behind an intact tympanic membrane without signs or symptoms of acute infection. OME is one of the most frequent pediatric diagnoses. Object recognition in otoscopy is also directed to the identification of particles or any material, e.g. hair, earwax, foreign objects, etc., which may obstruct the ear canal or coat the eardrum. Such applications are highly desired for routine care.

To perform otoscopy, a medical device called "otoscope" (sometimes also "auri-scope") is used. Otoscopy is a standard medical examination technique established more than 100 years ago. Medical students learn otoscopy early in their studies during the practical course in physiology. Typical diagnoses based on otoscopic examination are: otitis media (OM), otitis media with effusion (OME), otitis externa, and eardrum perforation. OME is defined by the presence of middle ear effusion, i.e. a liquid behind an intact tympanic membrane without signs or symptoms of acute infection. OME is one of the most frequent pediatric diagnoses. However, otoscopy is also used to generally identify and observe object's in the ear, such as earwax, hair and the eardrum. A typical otoscope 10' is shown in FIG. 3. The otoscope 10' comprises a handle portion 12' allowing the user to manipulate the otoscope during its application. The term "to manipulate" in this context refers to different kinds of manipulation, such as—but not limited to—holding the otoscope, aligning the otoscope with respect to the subject's ear, and turning on or off a light. The otoscope 10' further comprises a head portion 14' connected to the handle portion 12'. The head portion 14' exhibits a substantially tapering form—usually a conical form—extending along a longitudinal axis A' of the head portion 14'. The head portion 14' is substantially comprised of an empty funnel, wherein the tip of the funnel typically has a diameter of 3 mm. Furthermore, the head portion 14' has a proximal end 16' adjacent to the handle portion 12' and a smaller distal end 18' configured to be introduced into an ear canal C of a subject's outer ear. The term "end" in this context does not mean a single point but rather refers to a region or section of the head portion 14', wherein the proximal end 16' is located opposite to the distal end 18' with respect to the longitudinal axis A'. The ear canal C is partly surrounded by soft connective tissue C1 and—further down towards the middle ear—partly by hard bone C2.

If otoscopic methods of the art are applied e.g. to examine the subject's eardrum (as an object), the 3 mm tip has to be pushed deeply into the ear canal C while observing and simultaneously illuminating the subject's eardrum ED through the empty funnel. Normally, due to the natural curvature of the ear canal C, the eardrum ED is not visible from outside the ear. In order to overcome the natural curvature of the ear canal C, the skilled physician has to carefully pull the outer ear upward and to the back while carefully pushing the tip of the funnel into the ear canal as deeply as necessary to display the eardrum. The ear canal C has to be deformed in such a way that the physician has a free view onto the eardrum ED along the optical axis of the otoscope 10', wherein the optical axis corresponds to the longitudinal axis A' of the head portion 14'. The optics of an otoscope is situated only at the wider end of the funnel, i.e. at the proximal end 16' of the head portion 14', and essentially consists of a lamp and a lens (not shown) to magnify the image of the eardrum ED. The otoscopy procedure needs manual skills and significant training to carefully push the funnel into the ear canal C while looking inside and manipulating the curvature of the ear canal C by pulling the ear. For example, the trained physician is well aware to brace the hand holding of the otoscope against the subject's head to avoid injury to the ear canal C and the eardrum ED by placing the index finger or little finger against the head. In particular in young children—where the inner part of the ear canal is relatively short and where sudden head movement during examination may often occur—risk of penetration of the sensitive ear canal skin or even of the eardrum ED exists. Other than pain and handicapped hearing, such an injury is also known to potentially induce cardiovascular complication through vagal overstimulation and, therefore, has to be avoided under all circumstances.

Furthermore, especially in an inflamed ear, the mechanical manipulation of "straightening" the ear canal C typically causes considerable discomfort or even pain, rendering the examination of an infant even more difficult.

FIG. 4 illustrates that with a distal tip of the otoscope 10' being positioned far within the bony part C2, the ear canal C has to be "straightened" considerably in such a way that the longitudinal axis A is directed onto the eardrum ED, at least approximately. The distal tip of the head portion 14' is supported within the bony part C2, such that a proximal end of the head portion 14' contacting the soft connective tissue C1 can push the soft connective tissue C1 downwards. The head portion 14' is shaped such that there remains the danger of touching the eardrum ED.

For any application of an otoscope or its mode of use, it is desired to allow its user to distinguish the objects located in the ear canal or at its end, in particular the eardrum itself of any objects adhering to the eardrum.

BACKGROUND OF THE INVENTION

For the above reasons, reliably and securely handling an otoscope of the art is currently subject to only well trained physicians and not amenable to the larger community of practitioners. A study recently published in the US as a result of a survey has shown that even physicians often fail to (correctly) determine the status of e.g. the subject's eardrum or fail to correctly interpret the image provided by the otoscope (i.e. correct and meaningful object recognition). Such failures result in misinterpretation of the status of the inner ear canal or the eardrum. As a consequence, e.g. over-medication with antibiotics for treating supposed inflammations of the eardrum occurs, because physicians tend to err on the side of caution, or meaningless image interpretation occurs.

Notably, there also exist other otoscopic devices, as e.g. video otoscope, allowing a skilled expert to capture images of the subject's eardrum and the ear canal. Such video otoscopes comprise a bundle of light guides extending from the distal end of the head portion to a CCD-chip located remote from the distal end. The achievable resolution of the images depends on the number of light guides. In order to obtain images having a satisfying resolution, a significant number of individual light guides must be provided rendering devices by far too expensive for routine care. Moreover, all of the known video otoscopes having the CCD-chip located remote from the distal end of the head portion require superior handling skills by he physician. For the above reasons, they are not configured and suitable for domestic use by a larger community of practitioners, nor use by laypersons.

The otoscopic methods known in the art are—as a matter of fact—subject to the structural and geometrical characteristics of otoscopes as described above. All otoscopes currently on the market—including video otoscopes—generally are based on the following fundamental design: a relatively thin open funnel. Length, angle, field of vision and size of the funnels are essentially similar for all marketed otoscopes. As a result of these common characteristics, ease of use (due to safety issues) is limited for such devices. Methods for reliable detection of objects in the ear canal, including the eardrum, are remarkably intricate with such known otoscopes.

Consequently, until today otoscopy has almost exclusively been applied by well-trained medical doctors. However, it would be desirable to extend the capability of otoscopy beyond the trained professionals. Due to its broad spectrum of applications, it should be made amenable to any layperson, such as parents, who may desire to e.g. examine whether dirt or particles is/are located in the children's ear canal.

Prior art document US2013/027515 A1 describes an ear canal side scanner with a small diameter comprising a camera including e.g. a CCD or CMOS chip. The camera can be arranged at a tip of a probe of the side scanner. The scanner allows for side scans of lateral surfaces of the ear canal, e.g. in order to determine the length of the ear canal. The tip of the side scanner is positioned close to the eardrum before scanning.

Prior art document U.S. Pat. No. 5,910,130 A describes an otoscope with a miniature video camera or a solid-state imager, e.g. a CCD or CMOS. A light source can be provided in the form of a continuous ring of light emitting fibres. The head portion of the otoscope has to be introduced far into a straightened ear canal in order to observe the eardrum.

Prior art document US 2011/063428 A1 describes a medical device (an endoscope) comprising illumination means and a video camera based on wafer level optics, e.g. a solid state imager, and having a maximum outer diameter of less than 3.2 mm.

Prior art document US 2009/030295 A1 describes an instrument for capturing an image of an eardrum and a method for locating the eardrum on the image, especially based on color detection or brightness detection. Brightness can be evaluated in order to distinguish between two specific tissues. A rotation mechanism for applying one of two optical filters can be provided.

Prior art document U.S. Pat. No. 7,529,577 B2 describes a method for locating foreign objects in an ear canal, especially by determining the relative content of specific colours within the image using a color sensitive CCD element. Light can be passed from eccentrically arranged light guides via an annular lens on a mirror reflecting the light through a tube of transparent material, and reflected light passes via the mirror through a lens and is captured by a centrally arranged image guide.

Prior art document EP 2 014 220 A1 describes an apparatus for acquiring geometrical data of an ear's cavity with a black and white CCD or a colour sensitive CCD. Thereby, a distance measurement can be carried out, with respect to both a circumferential surface and the eardrum.

Prior art document EP 2 289 391 A1 describes an otoscope with a head portion and a fastening ring for reversibly mounting the head portion to a display portion.

Prior art document EP 2 277 439 A2 describes a clinical ear thermometer including an image sensor which is positioned radially offset, especially in order to provide a cavity in which a temperature sensor can be arranged at a distal end.

It is therefore an object of the present invention to provide a method that allows for reliable identification of objects in the subject's ear and that preferably shall be also domestically applied by laypersons without any—or at least with a significantly reduced—risk of causing injuries to the subject. In particular, it is an object of the present invention to provide a method of capturing images that allows for reliable identification of objects, especially the eardrum, without the need of introducing an otoscope as far as considerably within a section of the ear canal which is confined by hard bone. The object of the present invention can also be describes as to provide a method that allows for reliable identification of objects, especially the ear drum, substantially irrespective of any experience or knowledge with respect to the correct relative position of a head portion of an otoscope within the ear canal.

That object is achieved according to the present invention by a method exhibiting the features of claim 1. Preferred embodiments of the present invention are provided by the dependent claims.

In particular, that object is achieved by a method of identifying objects in a subject's ear, comprising the following steps: introducing an optical electronic imaging unit and at least one light source into an ear canal of a subject's outer ear, wherein the electronic imaging unit exhibits at least one optical axis directed in a distal direction, especially at the eardrum of the subject's ear; using the electronic imaging unit to capture at least one image from at least one eccentric observation point positioned on the at least one optical axis and positioned eccentrically within the ear canal; and determining brightness and/or color information to identify objects shown in the at least one image by electronic means, in order to automatically identify the objects, especially the eardrum. Such a method even allows for identification of objects which are arranged deep within the ear canal, e.g. the eardrum, even in case the electronic imaging unit is only introduced as far as a curvature or a transition area between soft tissue and hard bone confining the ear canal.

An electronic imaging unit according to the invention is preferably based on optical imaging and preferably comprises at least one optical camera defining an optical axis and/or comprises at least two optical axes defined by beam splitter optics.

As described above, in many cases, the optics of an otoscope adapted to carry out the otoscopic method according to art—comprising a lamp and a lens—are positioned anywhere between a proximal end and the distal end of the head portion, especially at the wider end of the funnel, i.e. not at the distal end of the head portion. As a consequence, the longitudinal axis of the head portion forms the optical axis of the otoscope. The optical axis has to directly point to the eardrum for enabling visual access through the ear canal to the eardrum. In order to enable such visual access state of the art methods require the practitioner to significantly deform the subject's ear, namely straightening the ear canal, and further require introducing a relatively narrow tip of the funnel deeply into the subject's ear canal, especially deeply into the bony part of the ear canal.

Introducing an electronic imaging unit which provides at least one eccentric observation point and/or at least one light source (preferably both) into an ear canal of a subject's outer ear and capturing imaged from the eccentric position—according to the method of the present invention—overcomes these disadvantages of such prior art methods using known otoscopes. In particular, an optical axis of an otoscope used for carrying out the method of the present invention does not have to correspond to the longitudinal axis of the head portion. Instead, an optical axis of the electronic imaging unit may be arranged radially offset.

In particular, in many cases, the ear canal of the outer ear is not straight-lined, but exhibits at least one curvature, especially at a transition area or transition point between soft connective tissue and hard bone confining the ear canal. The "corner" is provided by this curvature. Consequently, when carrying out the method of the present invention, the requirement to deform the subject's ear is eliminated or greatly reduced. Furthermore, the inventive method avoids the risk of injury to the ear canal, in particular the bony part of the ear canal, or to the eardrum by allowing the use of otoscopes with a tip of the head portion that exhibit significantly larger dimensions as compared to an otoscope according to the art. Thus, the risk of introducing the head portion of the otoscope too deeply into the subject's ear canal is considerably reduced. Both improvements pave the way to allow laypersons to carry out the method according to the invention.

An eccentric position or observation point allows for "looking around the corner". In particular, the eardrum can be observed in its entirety, even in case the distal tip of an otoscope is introduced only as far as a transition area between soft connective tissue and hard bone confining the ear canal. The larger the radial offset, the better the view onto the eardrum, even in case a distal end of an otoscope is positioned only in a transition area between soft connective tissue and hard bone confining the ear canal. Preferably, capturing the at least one image is carried out from an eccentric observation point which is positioned closer than 1.5 mm, more preferable closer than 1.0 mm, further preferred closer than 0.8 mm or even closer than 0.7 mm or 0.6 mm to an inner lateral surface of the ear canal, especially with respect to a diameter of the ear canal in the range between 4.8 mm and 5.2 mm. Such a method may be carried out with an otoscope exhibiting a head portion which fits into the ear canal, the head portion having radial dimensions (e.g. 5 mm) which at least approximately correspond to the diameter of the ear canal at a transition area between soft connective tissue and hard bone confining the ear canal.

In particular, a method according to the present invention allows for identifying the ear drum substantially irrespective of the relative position of a head portion of the otoscope within the ear canal, especially irrespective of any specific insertion depth into the bony part of the ear canal, i.e. the section confined by hard bone, or irrespective of any specific orientation of the head portion or a handle portion of the otoscope.

Preferably, an "optical axis of the electronic imaging unit" is an axis which extends from a most distal point of the electronic imaging unit in a distal direction, especially towards the eardrum, wherein its orientation is not modified any more by any optical components. The "optical axis of the electronic imaging unit" of an electronic imaging unit preferably is the optical axis with the largest radial offset.

As a further advantage of the present inventive method it enables the use of imaging devices which provide a larger field of vision. An optical component defining the field (or angle) of vision of the electronic imaging unit of such devices can be positioned at the distal end of the head portion, especially at the distal tip. Thereby, a much larger the field (or angle) of vision is obtainable than by methods which are based on the relatively acute empty funnel of an otoscope according to the prior art.

Once at least one image has been captured by the at least on electronic imaging unit, object recognition and unambiguous object identification (e.g. distinguishing objects, such as earwax, hair, and the eardrum) can be performed by determining brightness and/or color information of the pixels of the at least one captured image. Each pixel of the image obtained by the electronic imaging unit is characterized by a numerical value corresponding to the brightness of that pixel and—if the electronic imaging device comprises a color imaging device—also by a numerical value corresponding to the color of that pixel. Different objects can be identified e.g. by their typical color.

In a method according to the present invention, preferably, during capture of the at least one image, the ear canal is illuminated from an eccentric illumination point positioned eccentrically within the ear canal. Such a method allows illuminating the ear canal and even the eardrum, even if the otoscope is introduced only as deep as a transition area between two types of tissue or as a curvature. Such a method allows for providing appropriate illumination of all objects which may be captured from the at least one eccentric observation point.

In a method according to the present invention, the at least one image may be captured along at least one optical axis which is tilted, especially with respect to a longitudinal axis of the ear canal and/or with respect to a longitudinal axis of a head portion of an otoscope used for carrying out the method. A tilted optical axis allows for "looking around the corner" more effectively. In conjunction with an eccentric observation point, "looking around the corner" can be carried out even more effectively.

In other words: In addition to a radially offset arrangement, at lest one optical axis of the electronic imaging unit may be arranged at an angle with respect to the longitudinal axis (tilted against the longitudinal axis), allowing the device to "look around the corner" more effectively, or allowing the device to "look around the corner" even from a central observation point.

In a method according to the present invention, preferably, the method further comprises detecting infrared radiation by means of an infrared sensor unit. Providing a method comprising temperature detection in conjunction with an optical identification of objects allows for more reliable identification of the objects, e.g. of the eardrum. Providing an otoscope additionally with an infrared sensor unit, especially arranged centrically at the distal tip, allows for minimizing any risk of misdiagnosis. The infrared sensor unit can be connected to a logic unit, the logic unit being configured for processing data from both the infrared sensor unit and the electronic imaging unit, especially simultaneously. Data acquired by the infrared sensor unit can be verified based on data acquired by the electronic imaging unit, and vice versa. Brightness data or color information data can be correlated with temperature data. The infrared sensor unit can be provided at same positions like positions discussed in context with the electronic imaging unit or the light sources. Nonetheless, preferably, the infrared sensor unit is arranged for acquiring temperature data from a central point or any point which is arranged radially offset within the semicircle or the quadrant of the cross section of a distal tip of an otoscope in which the radially offset optical axis is arranged. Likewise, the infrared sensor unit can be displaced in the same manner as discussed in context with the electronic imaging unit or the light sources.

For improved object identification, a method according to the present invention preferably further comprises the following steps: using the electronic imaging unit to capture at least two images from different eccentric positions within the ear canal and/or with illumination from different eccentric positions within the ear canal; and comparing the at least two captured images with each other to identify objects shown in the images.

Thus, the above object is solved by a method of identifying objects in a subject's ear may comprise the following steps: introducing an electronic imaging unit and at least one light source into an ear canal of a subject's outer ear; using the electronic imaging unit to capture at least two images from different positions within the ear canal and/or with illumination from different positions within the ear canal; comparing the at least two captured images with each other to reliably identify objects shown in the images.

With these features, the electronic imaging unit is suitable to capture at least two images from different positions within the ear canal, e.g. by relocating one single electronic imaging unit when placed in the subject's ear canal and/or by providing images from two or more electronic imaging units positioned at different sites in the ear canal. Alternatively or additionally, the method may be based on the implementation of at least one illumination unit which is adapted to illuminate objects within the ear canal from different positions (e.g. from two or more positions). Preferably, a combination of both approaches is realized by the inventive method, which allows capturing images from different positions under differing illumination conditions. Such a mode of action allows for reliable identification of distinct objects (e.g. the eardrum, particles of earwax, hair, etc. in the subject's ear), as will be described in more detail below. Thereby, the risk of image misinterpretation and failure in object recognition is significantly reduced.

In a method according to the present invention, preferably, the different positions are defined or adjusted such that the captured images allow for stereoscopic viewing, the different positions being spaced apart from each other in a distance (d) of at least 2 mm or 3 mm, preferably at least 3.5 mm, more preferable at least 3.7 mm, especially between 3.7 mm and 4.4 mm for a distance between the positions for capturing the images, especially between at least two eccentric observation points (EOP), or especially between 3.7 mm and 4.6 mm for a distance between the positions for illumination, especially between at least two eccentric illumination points (EIP). Distances in such a range can ensure that the identified objects can be distinguished by stereoscopic viewing. Preferably, the distance is defined with respect to eccentric observation points. A large distance between different observation points facilitates stereoscopic viewing. Stereoscopic information determined by 3D mapping from parallax images can be determined.

In a method according to the present invention, preferably, the at least two images are captured from at least two different eccentric observation points (EOP), which are preferably arranged at the same radial offset within the ear canal, especially on the same pitch circle concentrically within the ear canal. A large radial offset can ensure that the objects can be observed from directions which vary considerably. Arranging the eccentric observation points (EOP) or optical axes on the same pitch circle allows for automatically displacing a plurality of eccentric observation points (EOP) by rotation, which facilitates differentiation of objects.

In a method according to the present invention, preferably, the at least two images are captured from at least two optical axes of the electronic imaging unit, in particular by a single image sensor of the electronic imaging unit or by at least two cameras of the electronic imaging unit. Alternatively, the at least two images are captured from a single optical axis of the electronic imaging unit. Capturing from different optical axes provides the advantage of e.g. fast acquisition of image data. Capturing from one single optical axes provides the advantage of e.g. acquiring image data continuously, e.g. during displacement of a camera of the electronic imaging unit. In other words: both alternatives provide the advantage of "looking around the corner" more effectively.

In a method according to the present invention, preferably, the at least two images are captured within a specific time frame, especially from at least two eccentric observation points. Time related capture of image data facilitates determining if a respective object is immobile or moves, e.g. an eardrum which is pressurized. For example, 10 or 20 images may be captures per second. At the maximum, e.g., 60 images are captures per second, especially during displacement of the respective optical axis or camera. The number of images captured per second can be adjusted in dependence on a speed of displacement, especially rotation, of the at least one optical axis or the at least one light source. In particular, the number of images captured per second increases with increasing speed of displacement.

In a method according to the present invention, preferably, during capture of the at least two images, illumination is sequentially switched on and off, the at least one light source preferably being provided by an LED, wherein illumination preferably is synchronized with a shutter of the electronic imaging unit. Synchronization with a shutter, i.e. a device that allows light to be collected for a determined period of time, exposing a light-sensitive electronic sensor, allows for exposure of individual frames at different illumination conditions. Such a method facilitates differentiation of objects. Also, such a method may allow for saving electrical power, and for increasing battery life, since illumination may be powered exclusively during exposure time of the imaging sensor.

If at least two images are captured from different positions within the ear canal, different objects, such as the eardrum and other objects are discriminated by comparing their positions as provided in the at least two images. That is, the inventive method makes it possible—in contrast to prior art methods—to determine the distance of various objects in the ear canal with respect to the electronic imaging unit according to the fundamental principle of stereoscopic viewing, also known as "parallax". Parallax is a displacement or difference in the apparent position of an object viewed along two different lines of sight, and is measured by the angle or semi-angle of inclination between those two lines. For example, a person closing only his left eye sees objects being relatively close at a position other than by closing only his right eye. However, the person will see relatively remote objects substantially at the same position. The human brain is thus able to determine the distance from the observer to the objects as a result of the parallax phenomenon. The same approach may be realized according to the present inventive method by the use of electronic means, such as a logic unit, when capturing images from different positions within the ear canal. Since the electronic imaging unit will not and cannot be introduced too deeply into the subject's ear canal according to the inventive method, the eardrum, as the membrane (object) terminating the ear canal, is relatively remote with respect to the electronic imaging unit, whereas other objects in the ear canal positioned more proximal to the electronic imaging unit are recognized as being less remote from the imaging unit as reference point. Thus, e.g. the eardrum can be readily distinguished from other objects located more proximal in the ear canal by the inventive method. Furthermore, a pathologic condition of the eardrum due to middle ear disease, e.g. retraction or bulging of the eardrum, can be distinguished. This also allows for better distinguishing between the eardrum and other objects within the ear canal. Alternatively or additionally, different objects, such as earwax, hair, and the eardrum, within the subject's ear canal may be discriminated by comparing their appearance as depicted by at least two images captured under illumination from different positions (for each single image) within the ear canal. If an object positioned relatively closely to the electronic imaging unit, such as earwax, is illuminated from different positions within the ear canal (by e.g. two or more distinct light sources or by e.g. one single light source which can be repositioned when carrying out the inventive method), the appearance of such an object will significantly differ in the at least two images captured according to the inventive method. Usually, the position of the sources of illumination is chosen such that, when carrying out the inventive method, they are still positioned closely to the electronic imaging unit. In contrast thereto, an object positioned relatively remote from the electronic imaging unit, such as the eardrum, will typically not change its appearance in the at least two images captured according to the inventive method by such illumination from different positions.

In a method according to the present invention, preferably, the at least two images are captured with illumination from at least two different eccentric illumination points (EIP), which are preferably arranged at the same radial offset within the ear canal, especially on the same pitch circle concentrically within the ear canal. Illuminating from eccentric illumination points allows for "looking around the corner" more effectively or with a better reliability. Eccentric illumination points enable illumination of the eardrum, especially the entire eardrum, even if a distal tip of an otoscope is introduced only as far as a transition area between soft connective tissue and hard bone confining the ear canal.

In a method according to the present invention, preferably, the at least two images are captured with illumination from at least two illumination axes, in particular by at least two light sources arranged eccentrically within the ear canal, especially at the same radial offset within the ear canal. Alternatively, the at least two images are captured with illumination from a single illumination axis, wherein a light source is displaced within the ear canal. Illuminating from different illumination axes provides the advantage of e.g. fast change or modification of the directions of illumination or light emission. Thereby, separate light sources may illuminate the ear canal without any displacement movement. Illuminating from one single illumination axes provides the advantage of e.g. modifying illumination continuously during displacement of at least one light source, e.g. in order to capture any images at specific instants at which illumination is favorable. In other words: both alternatives provide the advantage of providing favorable illumination conditions.

Furthermore, illumination at different angles may drastically change the reflective pattern and appearance of objects which are arranged close to the electronic imaging unit, while the reflective pattern and appearance of more distant objects only varies slightly. Thus, based on illumination at different angles, i.e. from different eccentric illumination points, the change in appearance can be evaluated in order to estimate the object's distance with respect to the imaging unit.

A method according to the present invention preferably further comprises a step of generating a calculated image based on the at least two captured images. One mode of carrying out the inventive method may be directed to exclusive object recognition of the eardrum. Thereby, the calculated image preferably does not display other more proximal (located more closely to the electronic imaging unit) objects, such as earwax and hair.

Under such circumstances, any object in the ear canal, e.g. a hair, which—at least partially—obstructs the view of the electronic imaging unit at a certain position within the ear canal onto the eardrum, may not prevent the user from obtaining the desired image information. The inventive method still allows to provide either a free view onto the eardrum by the electronic imaging unit, as the method allows to relocate the imaging unit to another position in the ear canal or may thereby at least provide a free view onto the part of the eardrum that was previously partially obstructed by the hair. For such an embodiment of the invention, the objects located relatively closely to the electronic imaging unit, such as earwax and hair, will be preferably identified as well, whereby the inventive method may provide an additional step, e.g. by electronic means, such as a logic unit, of generating a calculated image. Such a calculated image would not display any objects located relatively closely to the electronic imaging unit, such as earwax and hair, if the inventive method—as described for that embodiment—were intended to capture the best image possible of the eardrum. Consequently, an image will be calculated by the inventive method exclusively depicting the eardrum (and its structure), whereas other objects, such as hair and earwax, have been "eliminated" upon their recognition.

The term "relatively closely" in this context preferably refers to a distance of preferably not more than 6 mm, more preferably of no more than 4 mm from the reference point, e.g. the electronic image unit.

The image calculated according to the inventive method may be provided to a user by a display device, or may be stored to a storage card, or may be transferred to an external device via cable or wirelessly. If the calculated image is stored, the user, be it a layperson or a physician, may later analyze the image for whatever purpose.

If the electronic imaging unit comprises at least one color video camera, a method according to the present invention preferably further comprises a step of determining the spectral composition of reflections, especially the degree of reddishness, of any physiological objects in the ear canal (skin of the ear canal or of the eardrum), once the desired object (e.g. the eardrum) has been identified. Determining the spectral composition of reflections of e.g. the eardrum, or an area around the eardrum including the eardrum, may help the layperson to decide as to whether a physician should be visited or not, as it may potentially indicate inflammation of the eardrum. Inflammation of the eardrum may suggest e.g. a (bacterial/viral) infection. Any such more advanced or final disease diagnosis has to be carried out by the physician on the basis of other symptoms exhibited by the subject, which are observed by the physician, or by the physician's further examination. Disease diagnosis can therefore not be derived from the output provided by the method according to the invention, e.g. image information alone. Determining the degree of reddishness may help the layperson to decide not to visit a physician. Reddishness may also be observed elsewhere in the ear canal, as e.g. inflammation may also affect the inner part of the ear canal of the subject's outer ear. Thus, a method according to the present invention may additionally or alternatively determine the spectral composition of reflections of the inner part of the ear canal of the subject's outer ear, upon object recognition of the inner part of the ear canal by the inventive method.

The inventive method is based on an electronic imaging unit which preferably comprises a wide angle video camera, preferably a miniature camera, in particular a wafer-level camera. The term "wide angle" in this context refers to field of view angles of at least 80°, preferably of at least 110°, e.g. 120°. A method based on such wide angle cameras allows for detection of the subject's eardrum, even if the optical axis (corresponding to a "viewing direction") of the camera is not directly centered to the eardrum when applying the inventive method. The same holds if the eardrum is located—by applying the inventive method—relatively remote from the camera, compared to the distance between the eardrum and the tip end of an otoscope of the art during application. The electronic imaging unit used by a method of the invention may comprise a miniature camera, in particular a wafer-level camera of a substantially flat configuration, having dimensions of less than 3 mm×3 mm, preferably less than 2 mm×2 mm, even more preferable of about 1 mm×1 mm or even less than 1 mm×1 mm. Such a wafer-level camera can be produced nowadays extremely small in size with only about 3 microns per pixel. Therefore, wafer-level imaging technology allows for obtaining images of "sufficient" resolution of the eardrum, e.g. images of 250 pixels× 250 pixels, with a footprint of the camera including lens of only about 1 mm×1 mm or even smaller.

The term "miniature camera" refers to cameras having minimum dimensions with respect to the required method of capturing images, preferably lateral or radial dimensions in the range of 0.5 mm to 2.5 mm, more preferably in the range of 0.5 mm to 1.5 mm, or 1 mm. A "miniature camera" may exhibit a diameter in the range of e.g. 0.5 mm to 1.5 mm. The dimensions of the camera in an axial direction (parallel to the longitudinal axis) is circumstantial, i.e. only of minor importance. Radial dimensions of less than 2 mm×2 mm, even more preferable of about 1 mm×1 mm provide the advantage that an optical axis of the electronic imaging unit or camera can be arranged very close to an inner or outer lateral surface of the head portion, thereby enabling the otoscope to "look around the corner" with a relatively big angle, e.g. an angle in the range of 10° to 60°, preferably in the range of 15° to 40°, more preferable in the range of 20° to 30°.

A camera based on wafer technology provides a good compromise between light sensitivity and space requirements. The light sensitivity depends on the dimensions of an aperture or lens of the camera. The bigger the aperture, the higher the light sensitivity.

A wide angle camera may enable the otoscope to "look around the corner", in particular in conjunction with a radial offset and/or an optical axis which is tilted against the longitudinal axis of the head portion. A radial offset in conjunction with the ability of a "wide angle" may provide the advantage of "looking around the corner" without the need of an optical axis which is tilted. Nonetheless, the ability of "looking around the corner" can be ensured also by a camera being positioned radially offset and having an optical axis which is tilted. Most effectively, the ability of "looking around the corner" can be ensured by a wide angle camera which is positioned radially offset and which also has an optical axis which is tilted.

Preferably, the electronic imaging unit comprises at least three or four cameras, in particular miniature cameras, e.g. wafer-level cameras, which have dimensions such that all cameras can be arranged radially offset (with a maximum radial offset) from the longitudinal axis of the head portion.

In particular, especially with miniature cameras each having dimensions of about or even less than 1 mm×1 mm, a number of three cameras could be sufficient, as such small cameras can be positioned with a relatively high radial offset. The smaller the camera, the larger the realizable radial offset of an optical axis of the camera. A number of only three cameras also provides the advantage of reduced costs. In case the cameras have dimensions of e.g. about 1.2 mm×1.2 mm or 1.5 mm×1.5 mm, a number of four cameras is preferred. The higher the number of the cameras or optical axes, the higher the likelihood that at least one optical axis is positioned at a favorable eccentric position within the ear canal in order to entirely observe the eardrum. According to one embodiment, the electronic imaging unit comprises four cameras arranged at the same radial offset and having the same distance to each other in a circumferential direction.

A number of three, four, five or six miniature cameras or optical axes can eliminate any need for displacement or rotation of the head portion for positioning a camera in a preferred eccentric observation point. For example, with such an arrangement, it can be ensured that the head portion of the otoscope or the handle portion of the otoscope does not have to be rotated at all. In other words: The layperson only has to introduce the otoscope in an axial direction. It is not required to rotate any part of the otoscope. This may reduce the probability of any irritations of the tissue. Also, any prerequisite for skill or training of the layperson may be dispensable. Preferably, the electronic imaging unit exhibits a plurality of optical axes which are arranged rotationally symmetrically with respect to the longitudinal axis of the head portion. According to one embodiment, each optical axis may be provided by one camera.

Nonetheless, irrespective of the number of optical axes, additionally, a motion mechanism can be provided. Providing several cameras, e.g. two cameras, in conjunction with a motion mechanism provides the advantage that, if at all, the head portion or the otoscope only has to be rotated by a maximum angle of about 20° to 50°, in order to displace at least one of the cameras in a preferred position for "looking around the corner". A rotating movement of maximum 40° or 50° can position at least one of the cameras in a position in which the eardrum is best visible.

The present invention is based on the finding that an angle of 40° or 50° can be handled or operated without any problems, especially in an ergonomic way by laypersons, even in context with an application by the layperson. Thus, providing at least three optical axes may eliminate the need of any motion mechanism. It has been found that more than three or four cameras or optical axes are not necessarily required.

In a method according to the present invention, preferably, determining color information includes evaluation of the spectrum of reflected light, especially light reflected from the eardrum, especially in dependence on a specific intensity of illumination provided by the least one light source. Evaluation of the spectral response can lead to more certain information with respect to the type of tissue observed and/or a possible pathologic condition, e.g. an increased degree of reddishness in inflammation. Evaluation in dependence on the intensity can provide more reliable results, especially with respect to any characteristics of an inner lateral surface of the ear canal, facilitating to distinguish between the eardrum and an inner surface of the ear canal.

In a method according to the present invention, preferably, an intensity of illumination provided by the at least one light source is varied, especially during determination of the spectral composition of reflections, especially such that the degree of reddishness is determined based on at least two different intensities of illumination. Varying the intensity can provide more reliable results, especially with respect to any characteristics of the eardrum. In particular, the spectral composition of reflections can be determined with high accuracy. Preferably, the intensity is varied during the step of capturing a plurality of images, especially continuously varied. This allows for evaluating any change in the degree of reddishness more reliably.

In a method according to the present invention, preferably, a plurality of images is captured, each image being captured at a different intensity of illumination. Acquiring a plurality of images at different illumination levels allows for enhancing the dynamic range of the images. For each pixel, the information contained in the images can be evaluated in more detail. In particular, the method can be carried out with an otoscope which exhibits a logic unit allowing for processing or calculating a calculated image based on the plurality of images acquired at different illumination levels.

In a method according to the present invention, preferably, an intensity of illumination provided by the at least one light source is adjusted, preferably in dependence on reflected radiation as received by the imaging unit, especially such that the subject's tympanic cavity arranged behind the eardrum can be illuminated through the eardrum and reflected light from the tympanic cavity can be r observed. Adjusting the intensity such that the background of the eardrum can be observed enables identification of the eardrum with higher reliability. Thereby, optimally illuminating the eardrum or its background while respecting the dynamic range of the electronic imaging unit facilitates reliable identification of the objects. Furthermore, pathological conditions in the middle ear, i.e. tympanic cavity, can be determined. The present invention is also based on the finding that identification of the tympanic cavity covered by a semitransparent membrane can facilitate identification of the eardrum, as the eardrum is the sole tissue within the outer ear canal which is arranged in front of a cavity. A feedback illumination control can be provided in conjunction with illuminating the eardrum, especially by a logic unit which is coupled with one or several imaging units and light sources.

The present invention is also based on the finding that information relating to characteristics of the patient's tympanic cavity can be evaluated or processed (e.g. by a logic unit) in order to provide the layperson with an advice as to whether a physician should be visited or not. In particular, the present invention is also based on the finding that any serous or mucous fluid within the tympanic cavity can be an indicator of the eardrum itself, and can be an indicator of a pathologic condition in the middle ear. Within the ear canal, only behind the eardrum, such body fluid can be identified. Thus, evidence of any body fluid can provide evidence of the eardrum itself, as well as evidence of a pathologic condition, e.g. OME.

In a method according to the present invention, preferably, an intensity of illumination provided by the at least one light source is adjusted such that light emitted by the at least one light source is arranged for at least partially transilluminating the eardrum in such a way that it can be reflected at least partially by any object or body fluid within the subject's tympanic cavity arranged behind the eardrum. The present invention is based on the finding that translucent characteristics of the eardrum can be evaluated in order to distinguish between different objects within the ear canal, especially in order to identify the eardrum more reliably. Thereby, illumination can be adjusted such that tissue or hard bone confining the ear canal is overexposed, providing reflections (reflected radiation or light), especially reflections within a known spectrum, which can be ignored, i.e. automatically subtracted out. Such a method enables identification of the eardrum more reliably.

In particular, the degree of reddishness or reflectivity of light in the red spectral range can be determined at different illumination intensities. It can therefore be distinguished more reliably between light reflected by the eardrum itself, or by objects or fluids behind the eardrum, or by the mucosal covering the tympanic cavity wall. The reflectivity of light may be evaluated with respect to reflectivity within e.g. the green or blue spectral range. Typical spectral wavelength maxima are 450 nm (blue light), 550 nm (green light), and 600 nm (red light) for a respective (color) channel. The electronic imaging unit, e.g. comprising a color video camera, or any color sensitive sensor, may record images with respect to the red, green or blue spectral range, respectively. A logic unit may calculate, compare and normalize brightness values for each read, green and blue image, especially with respect to each separate pixel of the respective image. Such an evaluation may also facilitate medical characterization of the eardrum. In particular, the healthy eardrum is a thin, semitransparent membrane containing only few relatively small blood vessels. In contrast, an inflamed eardrum may exhibit thickening and/or increased vascularization. Also, any skin or tissue confining the ear canal as well as any mucosa in the middle ear may be heavily vascularized. In other words: The reflectivity in the different spectral ranges varies considerably between the different structures or objects as well as between healthy and inflamed tissue. Thus, referring to the spectral range enables more reliable differentiation between light reflected by the eardrum itself, or by objects or any fluid behind the eardrum, or by the tympanic cavity wall covered by mucosa.

Thereby, the risk of confounding any red (inflamed) section of the ear canal and the eardrum can be minimized. Also, the eardrum can be identified indirectly by identifying the tympanic cavity. In particular, any opaque fluid, especially amber fluid containing leukocytes and proteins, within the tympanic cavity may influence the spectrum of reflected light, depending on the intensity of illumination. At a relatively high intensity of illumination, the spectrum of reflected light will be typical for scattering in serous or mucous fluid containing particles like leukocytes, as light transmits the eardrum and is at least partially reflected by the opaque fluid. At a relatively low intensity of illumination, the spectrum of reflected light will be dominated by the eardrum itself, as a considerable fraction of the light does not transmit the eardrum, but is directly reflected by the eardrum. Thus, information relating to the tympanic cavity, especially more detailed color information, can facilitate identification of the eardrum as well as of pathologic conditions in the middle ear.

In particular, the present invention is also based on the finding that transilluminating the eardrum can provide supplemental information with respect to the characteristics of the eardrum (e.g. the shape, especially a convexity of the eardrum), and/or with respect to the presence of any fluid within the tympanic cavity. Spectral patterns of reflected light which are typical for eardrum reflection and tympanic cavity reflection can be use to determine the area of interest as well as a physiologic or pathologic condition of the eardrum and the tympanic cavity, especially in conjunction with feedback controlled illumination.

The present invention is also based on the finding that any fluid within the tympanic cavity evokes a higher degree of reflection than the physiologically present air. The fluid increases reflectance. In contrast, in case the tympanic cavity is filled with air, any light transilluminating the eardrum is only reflected with inferior intensity, as most of the light is absorbed within the tympanic cavity. In other words: transilluminating the eardrum and evaluating reflected light in dependence on the intensity of illumination can facilitate determining specific characteristics of the eardrum, e.g. an absolute degree of reflectivity in dependence on different wavelengths and intensities, providing more information or more certain information with respect to the type of tissue and its condition. Evaluating reflected light can comprise spectral analysis of translucent reflection, especially at different illumination intensities.

The present invention is also based on the finding that the degree of reflection in the red spectrum from the area of the eardrum may depend on the illumination level, i.e. the intensity of illumination. In particular, the red channel reflection can increase with increasing intensity of illumination. The higher the intensity of illumination, the higher the red channel reflection intensity. Also, it has been found that at relatively high intensities of illumination, not only the eardrum, but also any other tissue will reflect more light in the red spectrum. Therefore, on the one hand, providing a control or logic unit which is arranged for adjusting the intensity of illumination can facilitate identification of the eardrum. On the other hand, it can facilitate determining specific characteristics of the eardrum, e.g. an absolute degree of red channel reflection, such that the red channel reflection provides more information or more certain information with respect to the type of tissue and state of the tissue.

In particular, the present invention is also based on the finding that the degree of red channel reflection does not increase in the same manner with increasing intensity of illumination, depending on the presence of body fluid behind the eardrum. It has been found that in case there is body fluid within the tympanic cavity, with increasing intensity of illumination, the degree of red channel reflection does not increase as strongly as if the tympanic cavity was empty. Thus, based on the (absolute) degree of red channel reflection, the presence of fluid behind the eardrum can be evaluated. This may facilitate determination of pathologic conditions, e.g. OME.

In a method according to the present invention, preferably, identifying objects comprises pattern recognition of geometrical patterns, especially circular or ellipsoid shapes, or geometrical patterns characterizing the malleus bone, or further anatomical characteristics of the outer ear or the middle ear. Pattern recognition allows for more reliable identification of the eardrum. Pattern recognition can comprise recognition based on features and shapes such as the shape of e.g. the malleus, the malleus handle, the eardrum or specific portions of the eardrum such as the pasr flaccida or the fibrocartilagenous ring. In particular, pattern recognition may comprise edge detection and/or spectral analysis, especially shape detection of a circular or ellipsoid shape with an angular interruption at the malleus bone or pars flaccida.

In a method according to the present invention, preferably, pattern recognition is based on determination of an angle or range of angles of the objects, especially an angle with respect to an inner lateral surface of the ear canal or a longitudinal axis of the ear canal. Evaluation of the angle allows for more reliable identification of objects, especially the eardrum. Typically, the ear drum is arranged at an angle of about 30° to 60°, especially 40° to 50° with respect to an inner lateral surface of the ear canal or to a longitudinal axis of a section of the ear canal of the outer ear adjacent to the eardrum. It has been found that this anatomical characteristic can be used in order to facilitate identification of the eardrum, especially based on the assumption that any other objects within the ear canal are not arranged at any (single) specific angle.

Preferably, this method can be carried out with an otoscope comprising a logic unit which is arranged to determine the angle of any object which is identified, especially the angle with respect to a longitudinal axis of a head portion of the otoscope, and/or the angle with respect to a longitudinal axis of the ear canal.

In a method according to the present invention, preferably, identifying objects comprises determining the distance of the objects within the ear canal, especially with respect to an observation point of the electronic imaging unit. The present invention is also based on the finding that differentiation of different objects, especially identification of the eardrum can be facilitated by determining the most distant object within the ear canal of the outer ear. From an observation point within the ear canal of the outer ear, the eardrum is the most distant object.

In particular, the eardrum can be identified more reliably by evaluating if the distance of an object within the ear canal varied for a specific amount. The diameter of the eardrum typically is in the range between 8 mm and 11 mm. As the eardrum typically is arranged at an angle of about 30° to 60°, especially 40° to 50° with respect to an inner lateral surface or a longitudinal axis of the ear canal of the outer ear, the distance of the eardrum to an observation point considerably varies, especially in the range of about ±3 mm or 3.5 mm (maximum variation of about 5.5 mm to 7.5 mm).

Preferably, this method can be carried out with an otoscope comprising a logic unit which is arranged to determine the distance of any object which is identified.

In a method according to the present invention, preferably, the method further comprises calibrating a spectral sensitivity of the electronic imaging unit and/or calibrating color and/or brightness of the at least one light source. Calibration allows for more reliable identification of objects. It has been found that in case the light intensity is very high allowing for passing light through a healthy eardrum, which is semitransparent, a considerable amount of light within the red spectrum can be reflected by the tympanic cavity (especially due to illumination of red mucosa confining the middle ear). Thus, calibrating brightness or the intensity of emitted light enables more accurate evaluation of the (absolute) degree of red channel reflection and its source. In other words, spectral calibration of the imaging sensor in combination with spectral calibration of the illumination means allows for the evaluation of the tissue types and conditions.

In particular, with a method comprising calibration, any (actual) varying voltage of any batteries of an otoscope for carrying out the method does not imply or implicate any source of error. Using traditional otoscopes, it is likely that at low voltage, the spectrum of the illumination is shifted towards the red spectrum, i.e. less energy intensive wavelength, especially when using halogen light bulbs. Calibrating the spectral range and/or the intensity of illumination enables absolute spectral analysis. In other words: the electronic imaging unit can be provided with a calibrated color balance.

Calibration can be carried out e.g. based on feedback illumination control with respect to different objects or different kinds of tissue, once the respective object or tissue has been identified. Thereby, spectral norm curves with respect to different light intensities provide further data based on which calibration can be carried out.

A method according to the present invention preferably further comprises a step of informing the user correspondingly, if identification of the eardrum has failed. For example, it may be impossible for the electronic imaging unit to detect the eardrum and/or the inner part of the ear canal—irrespective of the position of the electronic imaging unit within the ear canal—because the ear canal is blocked by massive earwax or other particles. Alternatively, the eardrum may not be identified because the user did not carry out the inventive method due to inappropriate handling of the corresponding device (otoscope). In such a case, the user may try to repeat to carry out the method according to the present invention by re-adapting the position of the otoscope device in a correct manner, or by cleaning the ear canal.

In a method according to the present invention, preferably, the user is informed by an acoustic signal, especially an acoustic signal emitted outside of the ear canal, and/or by a visual signal. Emitting the acoustic signal out of the patient's ear which is inspected prevents that the patient is irritated by any sound. This enables calmly carrying on with diagnosis, especially self-diagnosis. Alternatively or in addition, a visual signal can provide any information, also additional information. A visual signal can be recognized by the user, even in context with self-diagnosis, e.g. in front of a mirror.

In a method according to the present invention, the at least one optical axis of the electronic imaging unit and/or the at least one light source is preferably displaced within the ear canal of the subject's outer ear along a predetermined path and/or by a predetermined distance between the moment of capturing a first image and the moment of capturing a second image. In order to allow for a relatively simple structural implementation of a corresponding motion mechanism for displacing the electronic imaging unit and/or the at least one light source within the ear canal, the predetermined path has preferably a circular form. Moreover, in order to clearly see a difference between the positions of an object shown in two images captured from different positions within the ear canal (according to the parallax phenomenon described above), the predetermined distance preferably amounts to at least about 1 mm.

In a method according to the present invention, preferably, the first and second images are captured during or before and after displacement of the at least one optical axis and/or the at least one light source. This enables fast acquisition of a plurality of images from favorable points of observation, which do not have to be predefined. Evaluation can be made based on the most favorable images, e.g. the images captures during most favorable illumination conditions.

Preferably, the electronic imaging unit or any component thereof, especially a camera, and the at least one light source are introduced into the ear canal of the subject's outer ear no further than to a distance from the eardrum of at least a few millimeters, preferably of at least 3 mm, more preferable of at least 10 mm, further preferred of at least 15 mm. This securely avoids injuries of the eardrum. As mentioned above, in order to avoid deeper introduction, the tip of the head portion of an otoscope adapted to carry out a method according to the present invention can exhibit greater dimensions compared to the otoscopes known in the art.

In a method according to the present invention, preferably, the electronic imaging unit and the at least one light source are introduced only as deep as not to touch a part of the ear canal which is confined by hard bone, or only as deep as a transition area between soft connective tissue and hard bone confining the ear canal. Such a short insertion depth facilitates or enables carrying out the method by laypersons.

In a method according to the present invention, preferably, the at least one image is captured from an eccentric observation point (EOP), especially on an optical axis which is tilted against a longitudinal axis of the ear canal or against a longitudinal axis of a head portion of an otoscope used for carrying out the method, such that the electronic imaging unit or at least one camera of the electronic imaging unit looks around a curvature of the ear canal. An eccentric observation point in conjunction with a tilted optical axis allows for effectively "looking around the corner" such that the eardrum can be observed from a point of observation which is arranged at a transition area between soft connective tissue and hard bone confining the ear canal. An eccentric observation point in conjunction with a tilted optical axis allows for introducing the distal tip not very deep, which ensures secure handling, even by laypersons.

In order to carry out the method of the present invention, preferably an otoscope is used, comprising a handle portion allowing a user to manipulate the otoscope during its application; and a head portion exhibiting a substantially tapering form extending along a longitudinal axis of the head portion, wherein the head portion has a proximal end adjacent to the handle portion and a smaller distal end configured to be introduced into the ear canal of the subject's outer ear. These features are also known from an otoscope of the art as described above. However, the otoscope used for carrying out the present invention preferably further comprises the electronic imaging unit, especially a camera, positioned in the distal end of the head portion, especially at a distal tip of the head portion, the at least one optical axis being positioned radially offset from the longitudinal axis, the radial offset preferably being at least factor 0.25 of the radial dimension of the distal end, more preferable at least factor 0.3, further preferred at least factor 0.35. Such a relatively large radial offset can ensure positioning the optical axis in a favorable eccentric observation point within the ear canal, even in case the distal tip in introduced only as deep as a transition point between soft connective tissue and hard bone.

Alternatively or in addition, the image can be captured from an observation point which is arranged eccentrically within the ear canal, wherein at least one of the at least one optical axis of the electronic imaging unit is be positioned radially offset from the longitudinal axis of the head portion. Such a configuration also allows obtaining a free view onto the eardrum without having to introduce the electronic imaging unit as deeply as it would be necessary if the electronic imaging unit were placed just centrally on the longitudinal axis of the head portion. The offset may be at least 1 mm, preferably at least 1.5 mm, more preferably at least 1.8 mm or 2 mm from the longitudinal axis.

When introducing the tip end of the head portion no deeper into the ear canal than to the border between the outer part and the inner part of the outer ear canal of the subject's outer ear, i.e. to a transition area between the two types of tissue, there is the risk that artifacts, such as earwax, hair and other kind of dirt from the outer part of the outer ear canal obstruct the view of the small electronic imaging unit onto the subject's eardrum. Therefore, it is advantageous to capture several images from different positions within the ear canal, especially from different eccentric optical axes. For doing so, the otoscope adapted for performing a method according to the present invention may comprise more than one optical axis, e.g. a plurality of optical axis provided by several cameras of the electronic imaging unit, and/or by beam splitter optics of the electronic imaging unit, positioned at the distal end of its head portion, respectively, and located at different positions on the head portion.

Providing a relatively small electronic imaging unit at the distal end of the head portion exhibiting at least one optical axis which is radially offset allows to "see" the patient's eardrum without the need to deform the patient's ear canal, or at least without having to deform the ear canal to such an extent as with the above described conventional otoscope. The reason for this is that there is no need for the "viewing direction" of the electronic imaging unit to correspond to the longitudinal axis of the head portion of the otoscope. Rather, the radial offset can ensure that there is a line of sight onto the eardrum even if the ear canal is not straightened, allowing the device to "look around the corner". In particular, in many cases, the ear canal of the outer ear is not straight-lined, but exhibits at least one curvature, especially at a transition area or transition point between soft connective tissue and hard bone confining the ear canal. The "corner" is provided by this curvature. In particular, virtually almost always, the ear canal has an S-shaped (sigmoid) form with a first curvature and a second curvature, the second curvature being closer to the eardrum than the first curvature. Particularly, the second curvature of the ear canal obstructs any optical line of sight or visual communication of an otoscope which is not introduced as far as at least some millimeters within the bony part of the ear canal. The "corner" can be defined as the second curvature of the ear canal. In particular, in a distal direction, the second curvature leads to the bony part of the ear canal. A transition point or area between soft connective tissue and hard bone is arranged at this second curvature. The second curvature leads into the section of the ear canal which is exclusively confined by hard bone. Preferably, the transition area can be defined as an area of about a few millimeters distal to (behind) and about a few millimeters proximal to (in front of) a curvature, especially 0 mm to 5 mm or 1 mm to 3 mm.

Such an electronic imaging unit can provide an otoscope which can be used by laypersons, without extensive otoscopy training and with a significantly reduced risk of causing injuries, especially with a significantly reduced risk of irritation of the patient's tissue, e.g. the tissue within the hard bone section of the ear canal. Such an electronic imaging unit allows for observing the eardrum substantially irrespective of the relative position of a head portion of the otoscope within the ear canal, especially irrespective of any specific insertion depth into the bony part of the ear canal, i.e. the section confined by hard bone. As the otoscope is arranged for "looking around the corner or curvature", the layperson does not have to introduce the head portion as far as a section of the ear canal which is confined by hard bone. While in traditional otoscopy, the physician has to introduce the otoscope at least as far as some millimeters within the bony part of the ear canal, i.e. considerably further inwards than the second curvature, an otoscope according to the present invention can be positioned adjacent to the second curvature. In traditional otoscopy, the otoscope is necessarily introduced far into the bony part of the ear canal, especially in order to provide a kind of support or rest or anchoring point at the distal tip of the otoscope. Once the distal tip of the otoscope is supported within the bony part, the physician can apply a leverage on the handle portion of the otoscope, in order to straighten the ear canal and in order to ensure an optical line of sight onto the eardrum. But, this kind of "alignment" of the otoscope or this kind of straightening out the ear canal is painful. In contrast, the otoscope according to the invention does not require such an "alignment" or straightening.

Preferably, the at least one miniature camera and/or any other optical unit or light source are positioned at a distance of less than 3 mm, preferably less than 2 mm, more preferable less than 1 mm, from the distal tip of the head portion, such that these components are introduced as deep as possible with respect to the position of the distal tip within the ear canal. Such an arrangement, especially as close as possible to the distal tip, allows for providing the maximum eccentricity within the ear canal, allowing for effectively "looking around the corner".

One optical axis of the electronic imaging unit may be positioned substantially centrically with respect to the longitudinal axis of the head portion. If one optical axis of the electronic imaging unit is positioned on the longitudinal axis of the head portion, a substantially flat optical component of the electronic imaging unit is preferable inclined or inclinable with respect to the longitudinal axis of the head portion, so that the one optical axis (or a "viewing direction") of the electronic imaging unit is angled with respect to the longitudinal axis of the head portion (tilted against the longitudinal axis), allowing the otoscope to "look around the corner" even from a central observation point.

In a method according to the present invention, preferably, at least two images are captured using at least two cameras of the electronic imaging unit each defining an optical axis of the electronic imaging unit and/or using beams splitter optics defining at least two optical axes, wherein the beams splitter optics preferably are used in conjunction with a single image sensor. Both alternative methods provide image data which can be evaluated in more detail than image data acquired from a single eccentric observation point. A plurality of different eccentric observation points facilitates e.g. evaluation of distances or three-dimensional shapes.

In case the electronic imaging unit exhibits beam splitter optics defining at least two optical axes which are arranged radially offset from the longitudinal axis, any objects, especially the eardrum, can be observed from different points of the distal tip of the head portion, without the need of a plurality of cameras. With beam splitter optics, a relatively large radial offset of each optical axis can be realized, especially a radial offset which can be even larger than the radial offset of a camera or a relatively small miniature camera. In particular, optical components of the beam splitter optics, such as lenses, mirrors or prisms, can be provided with relatively small radial dimensions. In particular, the optical components can be provided with a radial dimension or diameter smaller than 1 mm, preferably smaller than 0.9 mm, even smaller than 0.8 mm or 0.7 mm.

Also, beam splitter optics can provide an aperture which exhibits relatively large radial dimensions. A large aperture provides for good optical characteristics, especially good light sensitivity and/or a high dynamic range. Further, beam splitter optics can provide an arrangement for "looking around the corner" which is cost-effective.

Preferably, the beam splitter optics define a plurality of optical axes which are arranged rotationally symmetrically with respect to the longitudinal axis of the head portion. Such a design can ensure that the orientation of the head portion within the ear canal can be chosen freely by the user. The user does not have to orientate the handle portion of the otoscope in a specific direction.

Preferably, the electronic imaging unit exhibits an image sensor which is optically coupled with the beam splitter optics, especially with at least two of the optical axes, and which is positioned centrically on the longitudinal axis. An image sensor which is positioned centrically can provide a symmetric design of the imaging unit, which can be favorable also in view of constructing or manufacturing aspects. An image sensor which is arranged centrically can exhibit large radial dimensions, especially as the image sensor can be arranged more proximal in a section of the head portion which exhibits larger radial dimensions than the distal tip. Preferably, the image sensor is provided in conjunction with a plurality of optical axes, e.g. in conjunction with beam splitter optics. In other words: The electronic imaging unit is configured for providing an arrangement with a single image sensor and multiple optical axes. Reducing the number of image sensors can provide an otoscope with a straightforward design, which is cost-effective.

In a method according to the present invention, preferably, capturing the at least one image is carried out from a position within the ear canal in which the at least one optical axis is arranged at or adjacent to a transition point between soft connective tissue and hard bone confining the ear canal, especially in a maximum distance of 0 mm to 5 mm, preferably 1 mm to 3 mm. A maximum distance of 0 mm to 5 mm, preferably 1 mm to 3 mm with respect to the transition point or area allows for a minimum insertion depth.

In a method according to the present invention, preferably, at least one optical axis of the electronic imaging unit is parallel to the longitudinal axis or is tilted against the longitudinal axis, especially with a tilt angle ($\beta$) in the range of 10° to 60°, preferably in the range of 15° to 40°, more preferable in the range of 20° to 30. The optical axis is not necessarily tilted. Rather, an eccentric observation point and/or a field of vision exhibiting a wide angle, especially in conjunction with a miniature camera, allows for looking around a curvature, respectively.

In a method according to the present invention, preferably, at least two images are captured from at least two optical axes, preferably three or four optical axes, which are positioned in a predefined geometrical arrangement with respect to each other, especially with a maximum distance to each other and on the same pitch circle. A plurality of optical axes, especially arranged rotationally symmetrically on the same pitch circle with a maximum radial offset, facilitates capturing a plurality of images within short time. In particular, the ear canal can be observed from multiple favorable observation points at the same time, which may facilitate identification of objects, as it can be precluded that the user modifies the relative position of the head portion within the ear canal. Also, the predefined geometrical arrangement may facilitate evaluation of image data.

In a method according to the present invention, preferably, the at least one optical axis and/or the at least one light source is rotated, especially with respect to the handle portion. Displacement, especially rotation, of at least one optical axis allows for positioning the observation point in a most favorable position, substantially irrespective of the arrangement (orientation or depth) of the head portion within the ear canal. Also, multiple radially displaced cameras can be located at different preselected rotational locations (eccentric observation points).

In a method according to the present invention, preferably, the electronic imaging unit or camera or at least one optical axis and/or the at least one light source is rotated on a pitch circle having a maximum radial offset with respect to a diameter of a distal tip of the head portion. The maximum radial offset allows for favorable positions for observing the entire eardrum, even if the head portion is introduced only within the soft connective tissue (not contacting any bony part of the ear canal), or even if the position is unfavorable, e.g. because the layperson does not orientate or align the head portion correctly with respect to the longitudinal axis of the inner part of the ear canal.

In another preferred embodiment, the otoscope may further comprise a motion mechanism configured to allow displacement, especially along a predefined motion path, of the electronic imaging unit or the at least one optical axis and/or the at least one light source relative to the handle portion. With such a motion mechanism, it is possible to position the at least one optical axis in a favorable eccentric observation point, substantially irrespective of the position of the head portion within the ear canal. Also, it is possible to capture a plurality of images from different positions by one single camera or from one optical axis within the subject's ear canal, thereby avoiding the need for two or more cameras.

In a method according to the present invention, preferably, the electronic imaging unit or the at least one optical axis and/or the at least one light source is rotated by a motor, especially a brushless motor of a motion mechanism. Automatized displacement of a (respective) optical axis provides an otoscope which can be handled by layperson without any problems. The layperson does not have to align or orientate the head portion within the ear canal in any specific way. The layperson only has to introduce the head portion as far as a transition area. Additionally, a guidance system may guide the user in order to ensure an appropriate alignment and appropriate insertion depth.

In a method according to the present invention, preferably, identifying objects comprises determining the distance of the objects within the ear canal during rotation or from at least two different eccentric observation points. According to the invention, based on at least two different images taken from at least two different eccentric observation points, it has been found that the eardrum can be identified relatively easily. Typically, the ear drum is tilted at an angle of about 30° to 80° with respect to a longitudinal axis of the inner part of the ear canal. It has been found that two different eccentric observation points provided on a distal tip of a head portion of an otoscope arranged at least approximately concentrically within the ear canal of the outer ear are likely to be arranged at a different distance with respect to the respective opposing section of the eardrum. The front surface of the distal tip preferably is arranged at least approximately orthogonally with respect to the longitudinal axis of the ear canal of the outer ear. At least, the front surface is arranged at an angle with respect to an inner surface of the ear canal which is smaller than the angle at which the ear drum is arranged with respect to the inner lateral surface or a longitudinal axis of the ear canal. Therefore, almost inevitably or certainly, two different eccentric observation points provided on the distal tip are arranged at a different distance.

The otoscope may comprise a motion mechanism which is preferably configured to allow for at least partial rotation of the electronic imaging unit or the at least one optical axis and/or the at least one light source about an axis of rotation. The axis of rotation may correspond to the longitudinal axis of the head portion, especially along a predefined motion path. By displacing the electronic imaging unit along a predefined motion path, it is possible to automatically calculate the distance of the electronic imaging unit to the detected objects, as described above. In view of the typical size of objects found in the ear canal, such as hair and earwax particles, the motion mechanism preferably allows for displacement of the at least one optical axis of at least 1 mm, more preferable at least 2 mm, further preferred at least 3 mm, within the subject's ear canal. For example, in case a radial offset of 1.8 mm or 2 mm is realized, a rotation of 90° evokes a displacement of about 3 mm. A rotation of at least 90°, more preferably of at least 120°, even more preferably of 180° or even more degrees around the axis of rotation may be realized. In conjunction with an electronic imaging unit exhibiting two optical axes or comprising two cameras, a rotation of maximum 90° may be adequate in order to find the most favorable eccentric observation point. In conjunction with an electronic imaging unit exhibiting three optical axes or comprising three cameras, a rotation of maximum 60° or 70° may be adequate. Preferably, the motion mechanism allows for rotation in both directions, i.e. clockwise and counter-clockwise. The motion mechanism may also allow for rotational displacement about more than one axis. The motion mechanism may comprise at least one motor and one or more gears and/or bearings. The electronic imaging unit may be connected to a flexible cable, e.g. a flexible ribbon cable, to allow for such a movement.

An axis of rotation corresponding to the longitudinal axis of the head portion allows for displacing the at least one optical axis concentrically around the longitudinal axis. Thus, irrespective of the relative position of the optical axis, a maximum radial offset can be ensured.

In a method according to the present invention, preferably, the motion mechanism comprises a motor and is arranged for rotation about an axis of rotation, wherein the axis of rotation preferably corresponds to the longitudinal axis of the head portion. Such an arrangement ensures that the most favorable eccentric observation point can be found, at the lastest after having rotated the at least one optical axis around the longitudinal axis of the head portion for about 330° to 360°. Rotation can be carried out at a speed which is adjusted with respect to a preferred exposure time for capturing the images. Preferably, every 10°, an image or frame may be captured.

In a method according to the present invention, preferably, the electronic imaging unit or the at least one optical axis and/or the at least one light source is rotated such that it is positioned at the side of the ear canal which exhibits a relatively large radius of curvature. It has been found that from an eccentric observation point, the eardrum can be observed particularly well in case the eccentric observation point is positioned in a position next to a section of the ear canal exhibiting a large radius of curvature. In particular, in such a section, any getting out of position or any unintended displacement of the head portion does not affect the visibility of the eardrum as negatively as in a section of the ear canal exhibiting a small radius of curvature. In other words: positioning the eccentric observation point at a section of the ear canal exhibiting a high radius of curvature facilitates use of the otoscope by laypersons.

It has been found that an optimal eccentric position (eccentric observation point or eccentric illumination point) can be defined with respect to the smallest radius of curvature of the bend of the ear canal. In particular, the optimal eccentric position can be defined as a position which is laterally opposite of the smallest radius of curvature, i.e. as a position adjacent to the largest radius of curvature at the transition area between the two types of tissue or at the bend of the ear canal.

In a method according to the present invention, preferably, the at least one light source is rotated so as to maintain a predetermined distance with respect to the electronic imaging unit or the at least one optical axis, when the electronic imaging unit or the at least one optical axis is rotated by the motion mechanism. Such a method is advantageous, because the predetermined distal relationship between the at least one light source and the optical axis allows for improved (automatic) image analysis. If a motion mechanism is provided, the motion mechanism preferably also displaces the at least one light source. If the light source is provided in the form of a light guide, the light guide should be sufficiently flexible to allow for such a displacement of the at least one light source. Preferably, the light guide is fixed distally within the head portion, wherein the light guide is elastic, the elasticity allowing for bending and/or twisting. Alternatively, the light guide may be rigid, wherein the entire lightning apparatus may be displaced in conjunction with the head portion.

In a method according to the present invention, preferably, the at least one light source is rotated by rotating the electronic imaging unit, such that the motion mechanism allows for at least partial rotation of both the at least one light source and the electronic imaging unit by rotating the electronic imaging unit. Rotating the light source by means of the electronic imaging unit allows maintaining a predetermined distance there between with a high reliability.

Preferably, the electronic imaging unit or an optical component thereof, e.g. a camera, or the at least one optical axis and/or the at least one light source is tilted against an axis of rotation or against the longitudinal axis, so as to be continuously directed to a predetermined point on the axis of rotation or the longitudinal axis, the predetermined point having a fixed distance to the electronic imaging unit. In view of the typical length of the inner part of the outer ear canal of the subject's outer ear, the distance may be between 3 mm and 20 mm, preferably between 10 mm and 15 mm. Thus, an optical axis (corresponding to a "viewing direction") of the electronic imaging unit is optimized for centering on the eardrum.

In a method according to the present invention, preferably, the electronic imaging unit or the at least one optical axis and/or the at least one light source is tilted by a tilting mechanism, preferably at a tilt angle in a range between 10° and 50°, more preferably 20° and 40°, especially subsequent to the step of introducing the electronic imaging unit. A tilting mechanism allows for "looking around the corner" even more effectively. In case the head portion is positioned unfavorably, especially by a layperson, the tilting mechanism can ensure that the eardrum is visible anyhow. The tilting mechanism may be provided in conjunction with a motion mechanism. In particular, the motion mechanism may comprise a tilting mechanism.

In a method according to the present invention, preferably, displacement of the electronic imaging unit or at least one optical axis of the electronic imaging unit relative to the handle portion and/or tilting of the electronic imaging unit or the at least one optical axis against the longitudinal axis is carried out. Two motions, especially two motions which are controlled in dependence on each other, allow for "looking around the corner" more effectively. In particular, axially displacing or rotating an optical axis in conjunction with tilting the optical axis can enable observation of the entire eardrum, even from an observation point with a relatively small radial offset, or positioned unfavorably within the ear canal.

In other words: The otoscope may further comprising at least one mechanism configured to allow displacement of the electronic imaging unit or the at least one optical axis or at least one camera of the electronic imaging unit relative to the handle portion in conjunction with tilting it against the longitudinal axis. Such a combined mechanism, or two motion mechanisms combined with each other, especially two motion mechanisms which are controllable in dependence on each other, allow for "looking around the corner" more effectively. In particular, axially displacing or rotating an optical axis in conjunction with tilting the optical axis can enable observation of the entire eardrum, even from an observation point with a relatively small radial offset, or positioned unfavorably within the ear canal.

The head portion of the otoscope for carrying out the inventive method is preferably shaped in such a way that its distal end comprising the electronic imaging unit or optical component (e.g. camera) can be introduced only as deep into the ear canal as not to touch the eardrum, especially only as deep as a transition area between soft connective tissue and hard bone confining the ear canal. The ear canal of the subject's outer ear is limited by the eardrum. Notably, the ear canal of the subject's outer ear comprises an outer part which refers to a portion of the subject's outer ear (i.e. the subject's external auditory canal) that is surrounded by soft connective tissue and that usually contains hair and earwax. The outer part comprises approximately the outer half of the ear canal of the subject's outer ear. Furthermore, the ear canal of the subject's outer ear also comprises an inner part which refers to a portion of the subject's outer ear (i.e. the subject's external auditory canal) that is surrounded by hard skull bone and that is usually free from any hair and earwax. This portion extends from the proximal end of the outer part of the ear canal of the subject's outer ear to the eardrum. The inner part of the ear canal is very sensitive to pain in case of injury by mechanical friction. Injuring the inner part of the ear canal even bears the risk of cardiovascular complications through vagal overstimulation.

In a method according to the present invention, preferably, the head portion is introduced only as deep as a transition area between soft connective tissue and hard bone confining the ear canal, wherein the head portion is blocked within the ear canal. Preferably, the head portion exhibits a conical shape and the distal end exhibits a minimum diameter in the range of 4 mm to 6 mm, preferably 4.5 mm to 5.3 mm, further preferred 4.7 mm to 5.1 mm, especially 4.9 mm. Mechanically blocking the distal tip within the ear canal allows for secure handling.

Preferably, a tip portion of the distal end can be introduced into the ear canal of the subject's outer ear no further than to a distance from the eardrum of at least a few millimeters, preferably of at least 3 mm, more preferable of at least 10 mm, further preferred of at least 15 mm.

The tapering head portion of the otoscope for performing a method according to the present invention can be shaped with a blunt, rounded tip end, as compared to a conventionally known otoscope, thereby reducing the risk of introducing injury or discomfort to the subject. Thus, the device can be securely handled by laypersons. The otoscope adapted for performing a method according to the present invention, nevertheless, allows detecting the eardrum, since the electronic imaging unit is provided at the distal end of the head portion, exhibiting at least one optical axis which is radially offset.

Preferably, the distal end of the head portion is provided with a round and smooth shape. Moreover, the distal end may be made from a relatively soft material, such as silicone, or it may comprise an outer surface made of such a soft material. Furthermore, the longitudinal force upon introduction into the ear canal can be limited by a telescoping mechanism or the use of an elastic element. In case a telescoping mechanism is provided, preferably, the telescoping mechanism may be fixed, in order to facilitate detection of a force exerted on the otoscope.

The functional concept of a otoscope of the art as described above, however, requires the tip end of the head portion to be relatively small and acute (sharp), usually having a diameter of only about 3 mm. It is noted that the diameter of the inner part of the outer ear canal of an adult is about 4 mm. Therefore, if the user (untrained) does not pay attention, the tip portion might be introduced deeply into the inner part of the outer ear canal causing serious injuries to the subject. To substantially avoid this risk, the head portion of the otoscope adapted for carrying out a method according to the present invention (also having a tapered shape) preferably exhibits a diameter of at least 4 mm, preferably of more than 5 mm, more preferably of more than 6 mm, at a position along the longitudinal axis of the head portion of no more than 4 mm from a distal end point of the head portion. Thus, it is geometrically excluded to introduce the distal end of the head portion too far into the subject's ear canal. Different geometries of tapers may preferably be used according to the age group of the subject. For children, for example, the head portion of the otoscope adapted to carry out a method according to the present invention may exhibit a diameter of about 5 mm at a position along the longitudinal axis of the head portion of no more than 4 mm away from a distal end point of the head portion.

In a method according to the present invention, preferably, a step of relatively moving at least a portion of a probe cover covering the head portion with respect to the electronic imaging unit or the at least one optical axis is carried out, especially by a probe cover moving mechanism which is arranged for axial motion. In particular, moving the probe cover can ensure that an optical axis of the electronic imaging unit or camera can be arranged with a relatively large radial offset, especially without evoking the problem of any earwax particles obstructing visibility or with reduced probability of such earwax particles. Earwax particles or a layer of earwax often cover an inner surface of the ear canal. Thus, for an optical axis being arranged with a high radial offset, i.e. close to an inner lateral surface of the ear canal, there may be an increased likelihood of earwax particles adhering to the probe cover at a section covering the optical axis, thereby obstructing the view onto the eardrum. In other words: during insertion into the ear canal, an optical axis located radially offset at an edge of the distal tip is more likely to be obstructed by earwax. An optical axis which is radially offset is more likely to be obstructed than an optical axis which is arranged at least approximately centrically. Moving the probe cover, especially in an axial direction, can ensure that the view onto the eardrum is not obstructed, even in case the optical axis is arranged with a maximum radial offset close to an inner lateral surface of the ear canal. Thus, the present invention is based on the finding that by moving the probe cover, observation of the eardrum from an eccentric observation point with a relatively large radial offset can be made more practicable and more reliable. Moving the probe cover can ensure that the concept of "looking around the corner" is feasible and can be realized in a convenient way, even in case a layperson does not clean the ear canal prior to introduction of the head portion.

In particular, for displacing any particles or ear wax out of the line of sight, a relative motion or displacement of the probe cover induced by the moving mechanism is most effective in case the optical axis is positioned radially offset, especially with a maximum radial offset. The present invention is based on the finding that in most cases, it may be most favorable displacing the entire probe cover, apart from a central distal point at the distal tip of the probe cover. In other words: The whole probe cover can e.g. be pulled backwards in a proximal direction, except for a central distal point at the distal tip of the probe cover. At this distal point, preferably, a probe cover reservoir is provided. Thus, relative motion between the probe cover and the head portion may be minimum at the distal point, but maximum at any point of the distal tip which is positioned radially offset.

In a method according to the present invention, preferably, the probe cover is axially positioned in at least one specific axial position relative to the head portion by an adapter of the moving mechanism to which the probe cover is connected. A predefined axial position can ensure that the prove cover is moved in an axial direction only under specific conditions, e.g. when a specific (axial) force is exerted on the probe cover or the head portion, especially during insertion of the head portion into the ear canal.

In a method according to the present invention, preferably, the probe cover is axially guided along the head portion by the adapter. Axial guidance enables unfolding the probe cover such that in front of a camera, the probe cover is tensioned homogeneously.

In a method according to the present invention, preferably, during axial displacement, a reaction force is exerted on the adapter, especially in a distal axial direction, preferably by elastically deformable energy storage means. A reaction force threshold can ensure that the probe cover is only moved or displaced backwards at a time when the head portion or the distal tip of the head portion is positioned in its end position in a transition area between soft connective tissue and hard bone confining the ear canal, especially in a mechanical way.

In a method according to the present invention, preferably, the probe cover is axially displaced only if an axial force exerted on the probe cover and on the moving mechanism in the proximal direction exceeds a threshold value. A threshold value can be adjusted such that the otoscope is adapted for a specific group of persons, or for a specific kind of application. For example, the threshold value can be adjusted based on practical values, or the threshold value can be adjustable, e.g. by displacing or prestressing any energy storage means, especially elastically deformable energy storage means.

In a method according to the present invention, preferably, a displacement of the probe cover is detected by a motion sensor which is connected to the imaging unit and/or to at least one light source and/or to a logic unit of the otoscope. Detection of displacement can provide a way of coupling the displacement of the probe cover with any further method step, e.g. powering-up the camera or capturing at least one image.

In a method according to the present invention, preferably, a displacement of the probe cover is detected by the imaging unit of the otoscope. Detecting relative motion of the probe cover by the electronic imaging unit allows for control of the probe cover moving mechanism without the need of any further sensor. Controlling the step of moving the probe cover can minimize the relative motion. Preferably, the probe cover is only displaced such that an optical axis of the electronic imaging unit is not obstructed by e.g. ear wax. Friction between the probe cover and the head portion or between the probe cover and the ear canal can be minimized. Irritation of tissue can be minimized. Detection can be carried out e.g. based on transparency of the probe cover, especially in case the probe cover exhibits a varying wall thickness, or based on the color of the probe cover, especially in case the probe cover exhibits specific sections with specific colors.

In a method according to the present invention, preferably, displacement detecting by the electronic imaging unit may be combined with actuating an electromechanical latch, thus allowing for movement of the probe cover only after image analysis has revealed adequate insertion depth and/or axial or radial positioning. The electromechanical latch may be actuated only if a specific position has been detected bay the electronic imaging unit.

In a method according to the present invention, preferably, displacement of the probe cover is carried out in dependence on displacement of the electronic imaging unit or the at least one optical axis and/or the at least one light source, especially prior to any displacement of the electronic imaging unit or the at least one optical axis and/or the at least one light source. In particular, during displacement of the electronic imaging unit, images can be captured, especially continuously. Therefore, displacing the probe cover prior to any displacement of the electronic imaging unit can ensure that any potential favorable observation point is not obstructed by ear wax or other objects.

In a method according to the present invention, preferably, verifying appropriate positioning of the electronic imaging unit or the at least one optical axis is carried out based on the at least one captured image, especially during the step of introducing the electronic imaging unit, such that a user can be guided. Guidance is preferably carried out by verifying positioning based on a captured image, optionally in conjunction with data acquired by an infrared sensor unit. Guidance can facilitate use of the otoscope by laypersons. A layperson can be provided with a feedback about an appropriate insertion depth and insertion direction. Guidance can be implemented as an optical user feedback, e.g. lighted directional arrows, or as an acoustical feedback, e.g. an alerting sound, providing instructions to the user as to how to position the probe inside the ear canal.

User guidance can be carried out in conjunction with a specific method for capturing images and illuminating the ear canal. In particular, a camera or optical axis can be moved by some millimeters on a circular track while at least two light sources, especially LEDs, are alternatingly switched on. A series of images can then be captured in order to subtract artifacts, e.g. artifacts caused by dirt on a probe cover, or hairs and ear wax, and in order to discriminate the shape of the ear drum. The camera movement can be induced by a servo motor and controlled by a logic unit. According to one method, the camera is moved twice by a distance of ca. 1 mm, e.g. within ca. one second. In each of the corresponding three positions, the camera captures two images, preferably one with illumination provided by a light source arranged on one side of the camera, and one with illumination provided by a light source arranged on the other (opposed lateral) side of the camera. Both images can be averaged and subtracted, respectively. The averaged images can then be taken for calculating a final (calculated) picture through elimination of artifacts. The final picture can be freed of any (glossy) reflexes. Color information of this final picture can be evaluated, especially by quantifying the "red"

components. The subtracted images measure if light reflexes vary upon changing illumination from right to left. The difference of the light reflex pattern upon switching the LEDs is very strong on a glossy surface that is near to the camera such as ear wax but weak for the ear drum reflex. This discriminates the ear drum reflex (no variation) from glossy ear wax (strong variation).

In a method according to the present invention, preferably, the user is informed by an instruction indicating an insertion depth of a handle portion of an ostoscope used for carrying out the method. Providing instructions relating to the insertion depth can reduce the risk of introducing the head portion as far as considerably within the bony part of the ear canal.

In a method according to the present invention, preferably, the user is informed by an instruction indicating a direction of rotation of a handle portion of an ostoscope used for carrying out the method. Providing instructions relating to a specific radial position or rotational position facilitates positioning of the observation point or optical axis in a favorable position with good visibility of the (entire) eardrum.

In a method according to the present invention, preferably, the user is informed by an instruction indicating a tilting angle of a handle portion of an ostoscope used for carrying out the method, especially with respect to a longitudinal axis of the ear canal. Providing instructions relating to a tilting angle can ensure that the final position of the distal tip can be found easily, eve by laypersons which are not aware of the anatomical structure of the ear canal.

In a method according to the present invention, preferably, identifying objects comprises pattern recognition of geometrical patterns, especially circular or ellipsoid shapes, or geometrical patterns characterizing the malleus bone, or further anatomical characteristics of the outer ear or the middle ear. Pattern recognition allows for more reliable identification of the eardrum. Pattern recognition can comprise recognition based on features and shapes such as the shape of e.g. the malleus, the malleus handle, the eardrum or specific portions of the eardrum such as the pars flaccida or the fibrocartilagenous ring. In particular, pattern recognition may comprise edge detection and/or spectral analysis, especially shape detection of a circular or ellipsoid shape with an angular interruption at the malleus bone or pars flaccida. Pattern recognition may be carried out in conjunction with user guidance. Especially, pattern recognition may be carried out in order to guide the user and indicate which kind of objects are observed.

In a method according to the present invention, preferably, pattern recognition is based on determination of an angle or range of angles of the objects, especially an angle with respect to an inner lateral surface of the ear canal or a longitudinal axis of the ear canal. Evaluation of the angle allows for more reliable identification of objects, especially the eardrum. Typically, the eardrum is arranged at an angle of about 30° to 60°, especially 40° to 50° with respect to an inner lateral surface of the ear canal or to a longitudinal axis of a section of the ear canal of the outer ear adjacent to the eardrum. It has been found that this anatomical characteristic can be used in order to facilitate identification of the eardrum, especially based on the assumption that any other objects within the ear canal are not arranged at any (single) specific angle. A method according to the present invention can be carried out with an otoscope comprising a logic unit which is arranged to determine the angle.

In a method according to the present invention, preferably, capturing the at least one image is carried out with the distal end, especially the distal tip, being positioned at a distance of at least 10 mm, preferably of at least 15 mm to the eardrum, especially adjacent to a curvature of the ear canal in a transition area between the two types of tissue confining the ear canal, wherein the distal end preferably is mechanically blocked and centered within the ear canal. Such a distance can ensure a good overview of the whole ear canal. Also, such a position allows for safe application of the otoscope by laypersons.

In a method according to the present invention, preferably, during introduction of the at least one optical electronic imaging unit, a force exerted on the head portion is detected, especially a force exerted in the direction of the longitudinal axis. This allows for guiding the user in dependence on the forces applied to the otoscope. Also, force detection allows for controlling a moving mechanism or a motion mechanism based on the forces applied to the otoscope, i.e. based on the position within the ear canal, e.g. relating to a situation in which the distal tip of the head portion is blocked within the ear canal, especially at an end position between the two types of tissue.

In a method according to the present invention, preferably, user guidance is carried out based on specific values of detected forces. Such a user guidance can encourage the user to further introduce the head portion, or to reduce the force exerted on the head portion. In other words: force detection can facilitate user guidance, as is can be determined if the distal tip is already positioned in an end position, or if the distal tip is not introduced deep enough yet. Also, detecting the force exerted on the probe cover or on the head portion allows for controlling or adjusting an appropriate instant of time for relatively moving the probe cover, especially automatically, such that the use of the otoscope is easy to understand for laypersons. The layperson does not have to decide whether or when the probe cover has to be moved or not.

In a method according to the present invention, preferably, forces are detected by force detection means which are coupled to a/the motion mechanism. Such force detection means allow for activating the motion mechanism in dependence on forces exerted on the head portion, especially axial forces exerted from a lateral surface of the ear canal. Such a method allows for activating the motion mechanism at a time when the distal tip of the head portion is positioned in an end position adjacent to the inner curvature of the ear canal.

Alternatively or in addition, the force detection means which are coupled to a moving mechanism for moving a probe cover arranged at the head portion, wherein the force detection means activate, especially release the moving mechanism, preferably in case a threshold value of the force is exceeded. The threshold value can be defined such that an appropriate insertion depth can be ensured. In particular, according to one preferred method, a probe cover should only be displaced at a time when the head portion is arranged at an end position. Such a threshold value, which can be defined based on e.g. experience values, ensures that the head portion is introduced deep enough. In particular, such a force detection is advantageous in context with head portions exhibiting a diameter which is larger than in prior art, in order to prevent that the head portion is introduced too deep.

In a method according to the present invention, preferably, the ear canal is illuminated by a plurality of light sources, each light source illuminating a specific section of the ear canal. Thereby, segmented lighting of the ear canal can be carried out. For example, three light sources each illuminate a specific portion of the ear canal. Feedback regulation of each of the light sources allows for homogeneous illumination of the ear canal, especially based on different illumination levels. Preferably, a logic unit is coupled to each of the light sources, the logic unit allowing for feedback regulation and/or adjustment of illumination levels.

In a method according to the present invention, preferably, the otoscope further comprises an infrared sensor unit detecting temperature of objects within the ear canal, especially of the eardrum, wherein the infrared sensor unit is positioned in the distal end, especially at the distal tip, preferably centrically at the distal tip. Detection of temperature in conjunction with capturing a plurality of images allows for reliable differentiation of objects within the ear canal.

In a method according to the present invention, preferably, identifying objects comprises identifying the eardrum, the method further comprising the step of medically characterizing the eardrum based on at least one image captured of the eardrum, in order to provide medical evidence of the eardrum. This may help the layperson to decide as to whether a physician should be visited or not.

Medically characterizing the eardrum preferably is carried out automatically by the device, especially based on predefined ranges, e.g. with respect to temperature or a specific degree of reddishness. In other words: Medically characterizing the eardrum comprises at least one step of automatically evaluating the imaged captured by the electronic imaging unit, especially by means of a logic unit, e.g. based on one of the characteristics of the eardrum described above. Thereby, pre-diagnosis may be facilitated. Any more advanced or final disease diagnosis has to be carried out by the physician on the basis of other symptoms exhibited by the subject, which are observed by the physician, or by the physician's further examination.

In a method according to the present invention, preferably, medically characterizing the eardrum includes determining the spectral composition of reflections of the eardrum, or an area around the eardrum including the eardrum. Determining the eardrum's degree of reddishness can provide an index for assessing the likelihood of inflammation of the eardrum. Inflammation of the eardrum may suggest e.g. a (bacterial/viral) infection.

In a method according to the present invention, preferably, medically characterizing the eardrum includes identifying objects within the tympanic cavity of the subject. In particular, any opaque body fluid, especially yellow body fluid, within the tympanic cavity can be evaluated as an indicator of a disease. It has been found that a relatively high intensity of illumination (transilluminating the eardrum) allows for (more reliable) acquisition of information relating to the medical condition of the patient. It has been found that any body fluid within the tympanic cavity evokes a higher degree of reflection. The fluid increases reflectance. In contrast, in case the tympanic cavity is empty, any light transilluminating the eardrum is only reflected with inferior intensity, as most of the light is absorbed within the tympanic cavity. Body fluid behind the eardrum, in particular yellow body fluid, can be evaluated as an indicator for otitis media with effusion (OME), i.e. the presence of middle ear effusion, i.e. a liquid behind the eardrum without signs or symptoms of acute infection. In particular, such body fluid can be evaluated as a precursor of an inflammation. Such body fluid may contain serous and/or mucous fluid containing white blood cells due to immune response to infection. In other words: transilluminating the eardrum and evaluating reflected light, especially in dependence on the intensity of illumination, can facilitate determining specific characteristics of the eardrum, e.g. an absolute degree of reddishness, such that the specific characteristics provide more information or more certain information with respect to the probability of any medical condition, e.g. an inflammation. This may help the layperson to decide as to whether a physician should be visited or not. Any more advanced or final disease diagnosis has to be carried out by the physician on the basis of other symptoms exhibited by the subject, which are observed by the physician, or by the physician's further examination.

In particular, the present invention is also based on the finding that the degree of reddishness of the eardrum can depend on the illumination level, i.e. the intensity of illumination. In particular, the degree of reddishness can increase with increasing intensity of illumination. The higher the intensity of illumination, the higher the degree of reddishness. Also, it has been found that at relatively high intensities of illumination, not only the eardrum, but also any other tissue can exhibit a high degree of reddishness. Therefore, observing the tympanic cavity can facilitate determining specific characteristics of the eardrum, e.g. an absolute degree of reddishness, such that the degree of reddishness provides more information or more certain information with respect to the probability of any inflammation, i.e. an inflammation index.

In a method according to the present invention, preferably, medically characterizing the eardrum includes determining a curvature, especially a convexity, of the eardrum. This allows for detecting bulging or retraction of the eardrum. This may facilitate identification of the eardrum. This may also facilitate diagnosis, as in case of body fluid within the tympanic cavity (which is an indicator for specific medical conditions), the curvature of eardrum is convex, indicating an increased pressure within the middle ear. A high amount of body fluid evokes a convex curvature, i.e. towards the otoscope. Bulging or retraction may be an indicator for a specific medical condition or disease, e.g. for OME.

In a method according to the present invention, preferably, medically characterizing the eardrum includes pressurizing the eardrum and detecting mobility of the eardrum. For example, an otoscope for carrying out the method may comprise pressurization means, e.g. a pressure transducer or a pump, configured for applying a varying pressure within the subject's external ear canal. This technique is also known as "pneumatic otoscopy". Preferably, wherein the electronic imaging unit itself is configured for inspecting the mobility of the subject's eardrum when exposed to the varying pressure. The pressure is preferably applied by (compressed) air, wherein an air-tight chamber is formed by the subject's external ear canal and the corresponding device, i.e. the head portion or a probe cover put over the head portion.

The above mentioned object is also achieved by a method of identifying the eardrum in a subject's ear, comprising the following steps:
  introducing an optical electronic imaging unit and at least one light source into an ear canal of a subject's outer ear, wherein the electronic imaging unit exhibits at least one optical axis directed in a distal direction, especially directed at the eardrum of the subject's ear;
  using the electronic imaging unit to capture at least one image from at least one eccentric observation point positioned on the at least one optical axis and positioned eccentrically within the ear canal; and determining brightness and/or color information to identify the eardrum shown in the at least one image by electronic means, in order to automatically identify the objects, especially the eardrum;
the method further comprising the step of medically characterizing the eardrum based on at least one image captured of the eardrum, wherein a user guidance is carried out based on the at least one image captured of the eardrum, wherein the user is informed as how to position the electronic imaging unit in order capture the images of the eardrum, especially images of specific areas of the eardrum. Such a method may enable a layperson to apply the otoscope in order to acquire medical data of the eardrum, for facilitating a pre-diagnosis. The layperson may be guided such that the otoscope (its distal end) is positioned at a favorable observation point with respect to areas of interest of the eardrum. Any more advanced or final disease diagnosis has to be carried out by the physician on the basis of other symptoms exhibited by the subject, which are observed by the physician, or by the physician's further examination.

Medically characterizing the eardrum may comprise diagnosing an ear disease. Such a diagnostic method may comprises all steps of the previously described inventive method of identifying objects in a subject's ear. The inventive object recognition method may form part of the inventive diagnostic method. Firstly, objects shown in the at least on captured image are identified (and distinguished from other objects in the subject's ear), and then the status (such as brightness, color, etc.) of at least one of the identified objects is determined. Such a diagnostic method may even allow for reliably diagnosing e.g. an inflammation of the eardrum without the need of assistance of a skilled physician. An otoscope adapted for carrying out the diagnostic method according to the present invention may automatically detect and identify the eardrum, medically characterize the detected eardrum, and inform the user (who may be a layperson) about a medical condition of the eardrum, e.g. whether the eardrum is inflamed or not. Such a diagnostic method may further also comprise at least some of the preferred features of the method of identifying objects in a subject's ear, as described in detail above.

For hygienic reasons, the otoscope adapted for carrying out a method according to the present invention preferably further comprises an at least partially transparent probe cover configured to be put over the head portion. The probe cover may be made from a plastic material, preferably from a transparent plastic material. Such a probe cover may be designed as a single-use product that can be produced in larger numbers with low costs. The probe cover shall be transparent, at least at the locations where it covers the electronic imaging unit, so as to allow the electronic imaging unit to have a clear view onto the eardrum. The probe cover also inhibits contamination of the head portion of the otoscope comprising the electronic imaging unit, in particular when introducing the head portion into the subject's ear canal.

Preferably, the probe cover is adapted to be fixed to at least one section of either the head portion and/or the handle portion in such a way that the probe cover does not move relative to the handle portion during displacement of the electronic imaging unit by the motion mechanism. Otherwise, artifacts, such as earwax particles, adhering to the probe cover will depicted by the electronic imaging unit, even if the electronic imaging unit is displaced by the motion mechanism. This, however, would interfere with object identification (e.g. if the object to be identified is the eardrum) and elimination of artifacts from the captured images.

The otoscope adapted for carrying out a method according to the present invention may further comprise a probe cover moving mechanism adapted to move at least a portion of the probe cover with respect to the electronic imaging unit. Thus, artifacts, such as earwax particles, adhering to the probe cover and obstructing the view of the electronic imaging unit onto the eardrum can be moved away from the electronic imaging unit by the probe cover moving mechanism. In particular, the probe cover moving mechanism can ensure that an optical axis of the electronic imaging unit or camera can be arranged with a relatively large radial offset, as mentioned above.

Preferably, the probe cover is designed in a way that allows unfolding or peeling of portions of the probe cover in order to move portions of the probe cover contaminated e.g. with earwax away from the electronic imaging unit. A method according to the present invention may further comprise a step of moving the probe cover against the electronic imaging unit or vice versa.

To illuminate the subject's ear canal and eardrum, the otoscope adapted to carry out the inventive method may further comprise at least one light source typically positioned at the distal end of the head portion, especially at the distal tip of the head portion. The term "light source" is understood to apply to any source emitting photons. A light source positioned at the distal end or tip ensures illumination of the ear canal, even in case the distal tip is only introduced as deep as a transition area between the two types of tissue. Distal light sources facilitate realization of the concept of "looking around the corner".

Since geometrical restrictions limit the space at the distal end of the head portion, the light source is preferably formed by the distal end of a light guide. For example, the light guide may exhibit a diameter of less than 1 mm, preferably of less than 0.5 mm, more preferably of about 0.2 mm. The light guide may be connected to an LED located remote from the distal end of the head portion. The light guide may be e.g. a nylon light guide, preferably having a diameter of only about 0.2 mm to 1 mm. Alternatively, a light source may be formed e.g. by a small light emitting diode (LED) that is placed directly at the distal end of the head portion. The LED can ensure illumination with low energy consumption and minimum generation of heat.

The light guide can be made of polymethyl methacrylate (PMMA) or polyamide, especially polyamide 6.6. PMMA provides the advantage of good optical characteristics. Polyamide 6.6 provides the advantage of high flexibility.

It is advantageous, if the otoscope adapted to carry out the inventive method comprises a plurality of light sources at the distal end of the head portion, preferably with each light source being separately controllable. Thereby, the ear canal can be illuminated from a favorable eccentric illumination point, reducing e.g. shadowing. Also, by illuminating objects in the subject's ear canal from different positions, e.g. by sequentially switching on and off the individual light sources, it may also be envisaged to distinguish different objects in the ear, without necessarily having to displace the electronic imaging unit by a motion mechanism within the ear canal. An object relatively far away from the electronic imaging unit, such as the eardrum, will change its appearance only slightly when being illuminated from different positions at the distal end of the head portion. However, artifacts that are relatively close to the electronic imaging unit (such as hair and earwax) will change their appearance (position) drastically. The otoscope therefore preferably comprises means, in particular a logic unit, such as a microprocessor, adapted to distinguish different objects in the subject's ear based on images taken with the objects being illuminated from different positions.

Additionally or alternatively, the at least one light source may be controlled in view of the color, so that the color of the light emitted by the light source is changed. For example green color may be preferred to recognize earwax.

Preferably, a logic unit is coupled with at least two of the light sources and is arranged for individually switching on and off the light sources and/or for individually varying the light intensity. Preferably, the otoscope comprises the logic unit. The logic unit allows for feedback regulation and/or adjustment of illumination levels. Individually switching on and off enables stereoscopic viewing, especially depth analysis along the optical axes due to changes in reflected light patterns. Also, segmented lighting of the ear canal can be carried out. For example, three light sources each illuminate a specific portion of the ear canal. Feedback regulation of each of the light sources allows for homogeneous illumination of the ear canal, especially based on different illumination levels. Varying and adjusting the illumination level facilitates identification of the eardrum, in particular in dependence on the spectral composition of reflections of the eardrum with respect to surrounding tissue and with respect to a specific intensity of illumination. Preferably, the logic unit comprises at least one dimmer switch. Preferably, the least one light source preferably is dimmable, especially continuously dimmable.

Like the electronic imaging unit, the at least one light source is preferably positioned radially offset from the longitudinal axis of the head portion. Such a configuration allows illumination of the eardrum without the need to introduce the light source as deeply into the ear canal as it would be necessary, if the light source were placed centrally on the longitudinal axis of the head portion. The offset may be at least 1 mm, preferably at least 1.5 mm, more preferably at least 2 mm from the longitudinal axis. Preferably, the offset is maximum with respect to the confines of the outer diameter of the head portion. According to one embodiment, the offset is in the same range as a radial offset of the at least one optical axis. According to one embodiment, the radial offset of the at least one light source is as large as a radial offset of a camera of the electronic imaging unit. Such an arrangement is favorable in order to observe the entire eardrum or in order to reduce shadowing.

Preferably, the at least one light source is positioned adjacent to the at least one optical axis, preferably in a distance (b) smaller than 2 mm, more preferable smaller than 1.5 mm, further preferable smaller than 1.3 mm, especially between 1 mm and 1.3 mm or between 0.6 mm and 0.8 mm. Such an arrangement can enable emission of light with respect to one specific camera or optical axis. In particular, shadowing can be reduced. Light can be emitted onto the eardrum from a favorable position, especially e.g. in a direction which is at least approximately parallel to the ear canal. Also, an arrangement close to the optical axis can ensure that the light source can easily be displaced in conjunction with the optical axis in order to position the light source at a favorable eccentric illumination point.

Preferably, the otoscope exhibits at least two light sources or light guides which are arranged in a maximum distance (d) apart from each other, wherein the maximum distance (d) is at least 3.5 mm, more preferable at least 4 mm, further preferred in a range between 4.2 mm and 4.6 mm. Such an arrangement is favorable in order to observe the entire eardrum, especially without the need of rotating the camera or light source in a specific position. The relatively large distance can ensure that it is likely that one of the at least two, three or four light sources is arranged in a favorable eccentric illumination point.

Preferably, the at least one light source is arranged so as to maintain a predetermined distance with respect to the electronic imaging unit, even when the electronic imaging unit is displaced by the motion mechanism. Such a configuration is advantageous, because the predetermined distal relationship between the at least one light source and the electronic imaging unit allows for improved (automatic) image analysis. If a motion mechanism is provided, the motion mechanism preferably also displaces the at least one light source. If the light source is provided in the form of a light guide, the light guide should be sufficiently flexible to allow for such a displacement of the at least one light source. Preferably, the light guide is fixed distally within the head portion, wherein the light guide is elastic, the elasticity allowing for bending and/or twisting. Alternatively, the light guide may be rigid, wherein the entire lightning apparatus may be displaced in conjunction with the head portion.

Preferably, the at least one light source is coupled with the motion mechanism, especially directly or via the electronic imaging unit, such that the motion mechanism allows for at least partial rotation of the at least one light source about an axis of rotation, wherein the axis of rotation preferably corresponds to the longitudinal axis. Rotating the light source in a favorable position can allow for observing the entire eardrum with a high reliability.

Preferably, the at least one light source is fixed at the electronic imaging unit, in particular laterally fixed at a camera of the electronic imaging unit or at a support accommodating at least one optical component of the electronic imaging unit or defining the least one optical axis. With such an arrangement, rotation of both the electronic imaging unit and the light source can be realized quite easily. Thereby, the motion mechanism only has to be coupled with one of these components.

Preferably, the otoscope further comprises an infrared sensor unit positioned at the distal end of the head portion, especially centrically at the distal tip. Providing an otoscope comprising an infrared sensor unit for temperature detection in conjunction with an optical identification of objects allows for more reliable identification of the objects, e.g. of the eardrum.

The otoscope adapted for carrying out the inventive method may further comprise a logic unit, such as a microprocessor. The logic unit may be adapted to control the electronic imaging unit and/or the at least one light source and/or an infrared sensor unit. The logic unit may analyze the images obtained by the electronic imaging unit e.g. in order to compare two images obtained with the electronic imaging unit located at different positions within the ear and/or with the object illuminated from different positions, so as to identify and discriminate different objects in the subject's ear. The logic unit may further be adapted to generate or calculate a new image wherein predetermined objects that have been previously identified are eliminated.

DESCRIPTION OF THE FIGURES

Exemplary embodiments of methods as well as otoscopes adapted for carrying out the method of the present invention will be described in more detail in the following with respect to the drawings, wherein:

FIG. 1 schematically shows a cross-sectional view of a head portion and of a part of a handle portion of an embodiment of an otoscope for carrying out the inventive method;

FIG. 2 shows an enlarged view of a plate covering a bore provided in the head portion illustrated in FIG. 1;

FIG. 13A schematically shows an otoscope which can be used for a method according to the present invention, with its head portion partially introduced into the patient's ear canal;

FIG. 13B schematically shows the otoscope shown in FIG. 13A with its head portion introduced into the patient's ear canal as far as to an end position in which the ear drum can be observed;

In case any reference sign is not explicitly described in a respective figure, it is referred to the other figures. In other words: Like reference characters refer to the same parts or the same type or group of device throughout the different views.

DESCRIPTION OF PREFERRED EMBODIMENTS

Figure 3:
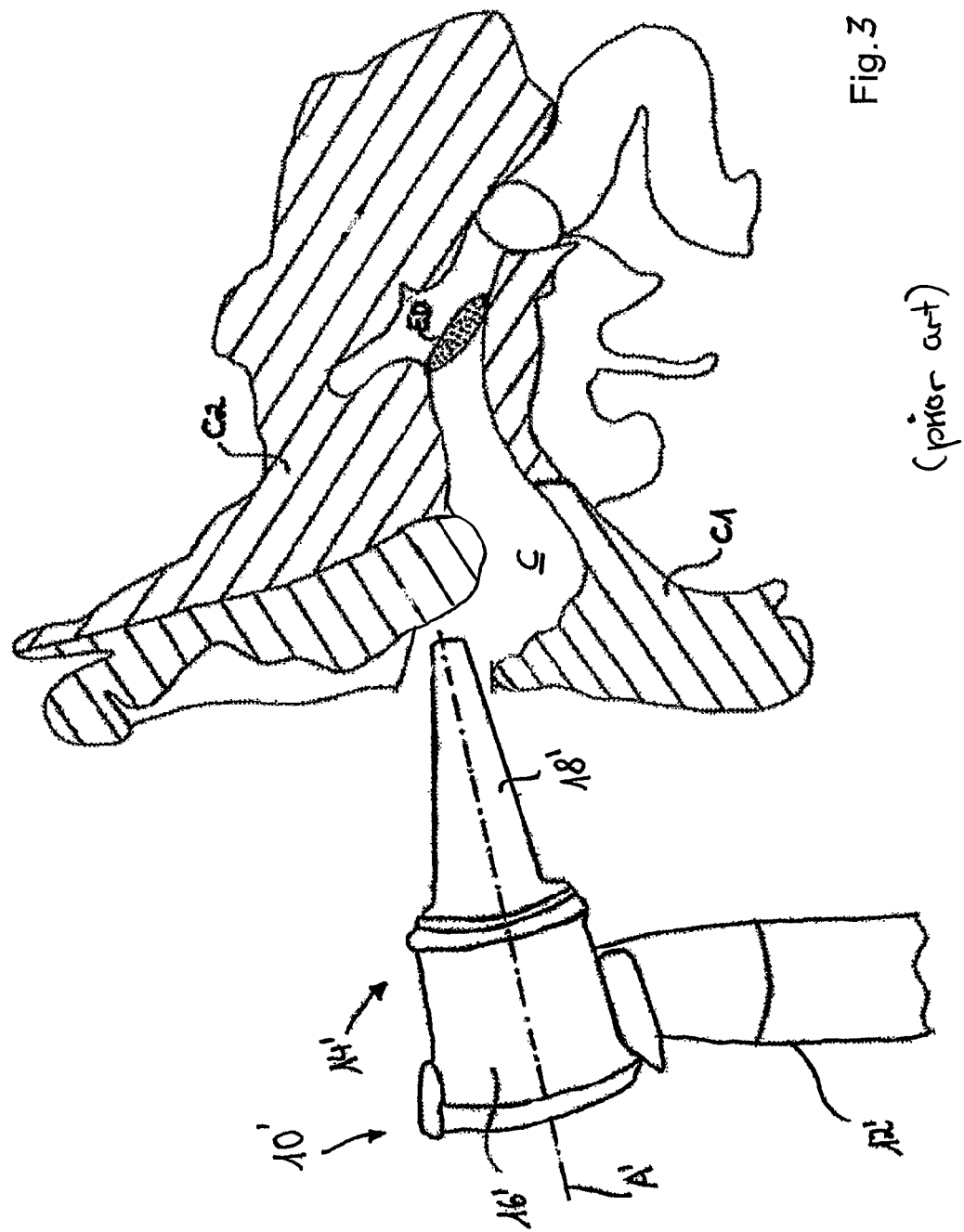
FIG. 3 shows an otoscope of the prior art, with its head portion partially introduced into the subject's ear canal.
Figure 4:
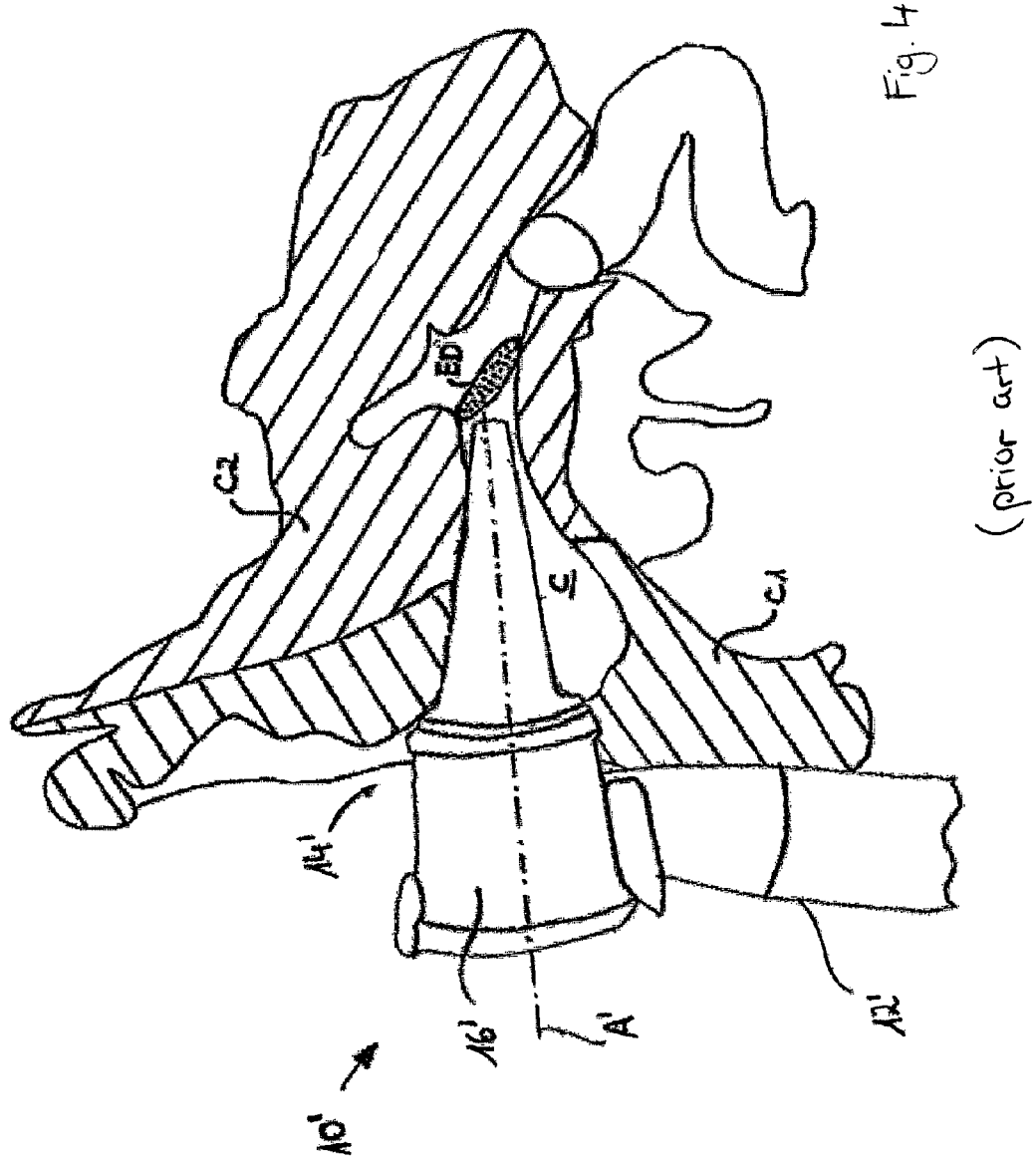
FIG. 4 shows the otoscope of FIG. 3 with its head portion fully introduced into the subject's ear canal.

FIG. 1 schematically shows a cross-sectional view of a head portion 14 and a part of a handle portion 12 (only shown in phantom lines) of an embodiment of an otoscope 10 adapted for carrying out the method according to the present invention. As can be seen from FIG. 1, the head portion 14 has a substantially tapering form extending along a longitudinal axis A of the head portion 14. The head portion 14 comprises a relatively large proximal end 16 adjacent to the handle portion 12 and a smaller distal end 18. The distal end 18 of the head portion 14 is adapted to be introduced into a subject's ear canal.

Furthermore, the head portion 14 comprises a rotatable, radial inner portion 20 and a fixed, radial exterior portion 22. The rotatable portion 20 is rotatable about an axis of rotation R which—in the shown exemplary embodiment—corresponds to the longitudinal axis A of the head portion 14. A motion mechanism 24 comprising a servo motor 26 is positioned within the handle portion 12 and is coupled to the rotatable portion 20 of the head portion 14, so as to rotate the rotatable portion 20 about its axis of rotation R relative to the fixed portion 22 of the head portion and relative to the handle portion 12 of the otoscope 10. The rotatable portion 20 is supported by a radial bearing 28 (also only schematically shown).

In the exemplary embodiment shown, the exterior portion 22 of the head portion 14 comprises a support structure 30 providing the required stability to the head portion 14. The support structure is at least partially covered by an outer cladding 32 formed from a relatively soft material, such as silicone. The cladding 32 makes it more comfortable for the subject to introduce the distal end 18 of the head portion 14 into his ear canal. The cladding 32 may comprise a circular slot-like recess 33 adapted to engage with a complementarily formed circular tongue of a probe cover (not shown). The probe cover may be formed from a plastic material and may be adapted to be put over the head portion 14. Preferably, the probe cover is formed from a transparent material. Its wall may be relatively thin, thereby making the probe cover relatively flexible. At least a portion of the probe cover covering the distal end 18 of the head portion 14 should be transparent, so as to allow an electronic imaging unit (described in the following) which is located at the distal end 18 of the head portion 14 to have a free view through the probe cover. For hygienic reasons, the probe cover is preferably designed as a single-use product. The probe cover also reliably inhibits contamination of the distal end 18 comprising the electronic imaging unit. Without such a probe cover there is a high risk that e.g. earwax particles may adhere to the electronic imaging unit (thereby deteriorating the image quality thereof) when introducing the distal end 18 into the outer part of the ear canal of the subject.

The head portion 14 comprises a distal end point 34 which, in the shown exemplary embodiment, is located substantially on the longitudinal axis A of the head portion 14. However, the head portion 14 might alternatively have a tapering shape that is not substantially symmetrical to its longitudinal axis A (as shown in FIG. 1) but is more adapted to the anatomy of the human ear canal.

Irrespective of the precise shape of the head portion 14, the head portion 14 is preferably dimensioned in such a way that it cannot be introduced into the inner part of the ear canal of the subject's outer ear. In the exemplary embodiment shown, the distal end 18 of the head portion 14 has a substantially round shape. Only a few millimeters (less than 4 mm) from the distal end point 34 in the direction of the longitudinal axis A, the head portion 14 exhibits a diameter of more than 5 mm. Since the inner part of the ear canal of an adult usually exhibits a diameter of 4 mm, there is no risk that the distal end 18 of the head portion 14 is inadvertently introduced too deeply into the subject's ear canal. Therefore, injuries to the sensitive skin of the inner part of the ear canal and/or to the eardrum can be reliably avoided.

The movable portion 20 comprises a bore 36 extending substantially along the axial direction A of the head portion 14, but not exactly parallel thereto. The distal end of the bore 36 is located in proximity to the distal end point 34, but offset with its bore axis B by at least 2 mm from the longitudinal axis A. Furthermore, the distal end of the bore 36 is closed by a plate 38. An enlarged top view of the plate 38 is shown in FIG. 2. Since the bore 36 is cylindrical in shape, the plate 38 has a generally circular appearance in FIG. 2 with the bore axis B forming the center thereof. However, the bore 30 and/or the plate 38 may equally exhibit other shapes.

The plate 38 supports an electronic imaging unit 40 comprising a wide-angle color video camera 40.1 and distal ends of four light guides 42. In the exemplary embodiment, the light guides 42 are located around the video camera 40.1, such that one light guide 42 is associated with each of the four lateral sides of the substantially rectangular video camera 40.1. However, this is not a prerequisite for the present invention. Instead of four light guides 42, for example, only two light guides 42 may be provided in the otoscope 10. The video camera 40.1 is advantageously a wafer-level camera of dimensions between 1 mm and 2 mm having a substantially flat configuration. The wafer-level camera advantageously exhibits dimensions of only about 1 mm×1 mm providing a resolution of about 250 pixels of 250 pixels. The plate 38 has a diameter between 1.5 mm and 2.0 mm and the light guides 42 have a diameter of only about 0.2 mm.

The video camera 40.1 is connected to a distal end of a cable (not shown). The cable, e.g. a ribbon cable, extends through the bore 36 and into the handle portion 12 of the otoscope 10. A distal end of the cable is connected to a logic unit 44, such as a microprocessor, which is schematically illustrated in FIG. 1. Similarly, the light guides 42 (not shown in FIG. 1) extend through the bore 36 and into the handle portion 12 of the otoscope 10. Proximal ends of the light guides 42 are connected to four LEDs 46, respectively. The LEDs 46 are positioned—like the logic unit 44—within the handle portion 12 of the otoscope 10. The LEDs 46 can be switched on and off individually. Furthermore, the handle portion 12 preferably comprises a memory 48 for storing images captured by the video camera 40.1. The memory may be formed e.g. by a storage card slot and a corresponding storage card inserted in the slot. The handle portion 12 may further comprise a display (not shown) for displaying the images taken by the camera 40.1 to the user. Additionally or alternatively, the handle portion 12 may comprise a cable connection port, such as a USB-port, and/or a wireless connection, such as Bluetooth® or WIFI®, and/or an energy supply, such as a (rechargeable) battery. These additional (optional) components of the handle portion 12 are known e.g. from digital cameras.

For capturing images of a subject's inner part of the ear canal, and in particular of a subject's eardrum, the distal end 18 of the head portion 14 has to be introduced into the subject's ear canal. Due to the shape of the head portion 14 there is no risk to insert the distal end 18 too deeply into the ear canal. That is, the shape and geometry of the distal end 18 does not allow for significantly introducing the distal end point 34 into the subject's inner part of the ear canal which is very pain-sensitive. Therefore, injuries to the skin of the inner part of the ear canal and/or the eardrum can be reliably avoided. The geometry and the technology of the inventive otoscope do not require deforming the subject's ear as with an otoscope of the art, as described above. Consequently, the otoscope adapted to carry out the method according to the present invention can also be securely applied by layperperson.

Even though the distal end 18 of the head portion 14 will not be inserted into the inner part of the ear canal, the otoscope, nevertheless, allows for capturing images from the inner part of the ear canal and the eardrum, because of the wide angle camera 40.1 being provided at the distal end 18 of the head portion 14. In order to improve the ability of the camera 40.1 to "see" the eardrum, the camera 40.1 is placed offset from the longitudinal axis A of the head portion 14. Furthermore, the main "viewing direction" of the camera 40.1, corresponding to the bore axis B, is angled with respect to the longitudinal axis A of the head portion 14. The bore axis B and the longitudinal axis A intersect at a point having a predetermined distance from the distal end point 34, wherein the predetermined distance corresponds to the typical length of a subject's inner part of the ear canal, so that the camera 40.1 is directed to the eardrum.

When the distal end 18 of the head portion is introduced in the subject's ear canal, it may happen that objects, such as earwax particles or hair, in front of the camera 40.1, e.g. adhering to the probe cover, partially or even fully obstruct the view onto to eardrum. Therefore, the motion mechanism 24 may turn the rotatable portion 20 of the head portion 14 with respect to the remaining otoscope 10 about its axis of rotation R. For example, the motion mechanism 24 may rotate the rotatable portion from an initial position by about 120° in clockwise direction, then from the initial position by about 120 in counter-clockwise direction, and finally return to the initial position. The camera 40.1 may capture one or more images from each of these equally spaced three positions. The logic unit 44 may identify different objects in the subject's ear by comparing the images received from the camera 40.1. In particular, the logic unit 44 may discriminate the eardrum from other objects by determining their distance to the camera 40.1 according to the principle of stereoscopic viewing, as described in more detail above.

Additionally or alternatively (preferably additionally) to the identification process described above, more than one image may be taken from each of the three positions of the camera 40.1, with different LEDs 46 switched on and off for each captured image. Illumination of the eardrum and other objects from different positions also assists to discriminate these objects, as described in more detail above.

Finally, a new image may be generated (preferably by the logic unit 44) in which objects, such as hair and earwax, are eliminated so as to clearly show the eardrum. The logic unit may discriminate image pixel areas that change their brightness values above a certain threshold when switching between LEDs 46 illuminating from different positions. Further, the logic unit may determine areas which depict objects close to (in the close proximity of) the distal tip by evaluating their reflection intensity. The logic unit may calculate a "mosaic" image, especially by using pixel information from different images taken at different illumination angles, in order to optimize exposure of areas of interest and/or in order to eliminate any obstructive object in the foreground, like e.g. hair and earwax particles. In order to create such "mosaic" or "stitched" or "composed" image, pixel information from separate images as well as from the same image may be averaged, subtracted, added, multiplied, and/or normalized. The degree of reddishness of the eardrum can then be easily determined, especially based on any such image evaluation method as describes above. The user may be provided with corresponding information, assisting him to decide as to whether see the physician, or not. Also if the otoscope failed to detect the eardrum because of massive earwax in the subject's ear canal, corresponding information may be provided to the user. The user may then decide to visit a physician for having his ear canal cleaned.

Alternatively, the otoscope may provide pictures showing only objects other than the eardrum, e.g. showing only an object that has been unintentionally introduced into the ear canal, such as a pencil tip.

Figure 5:
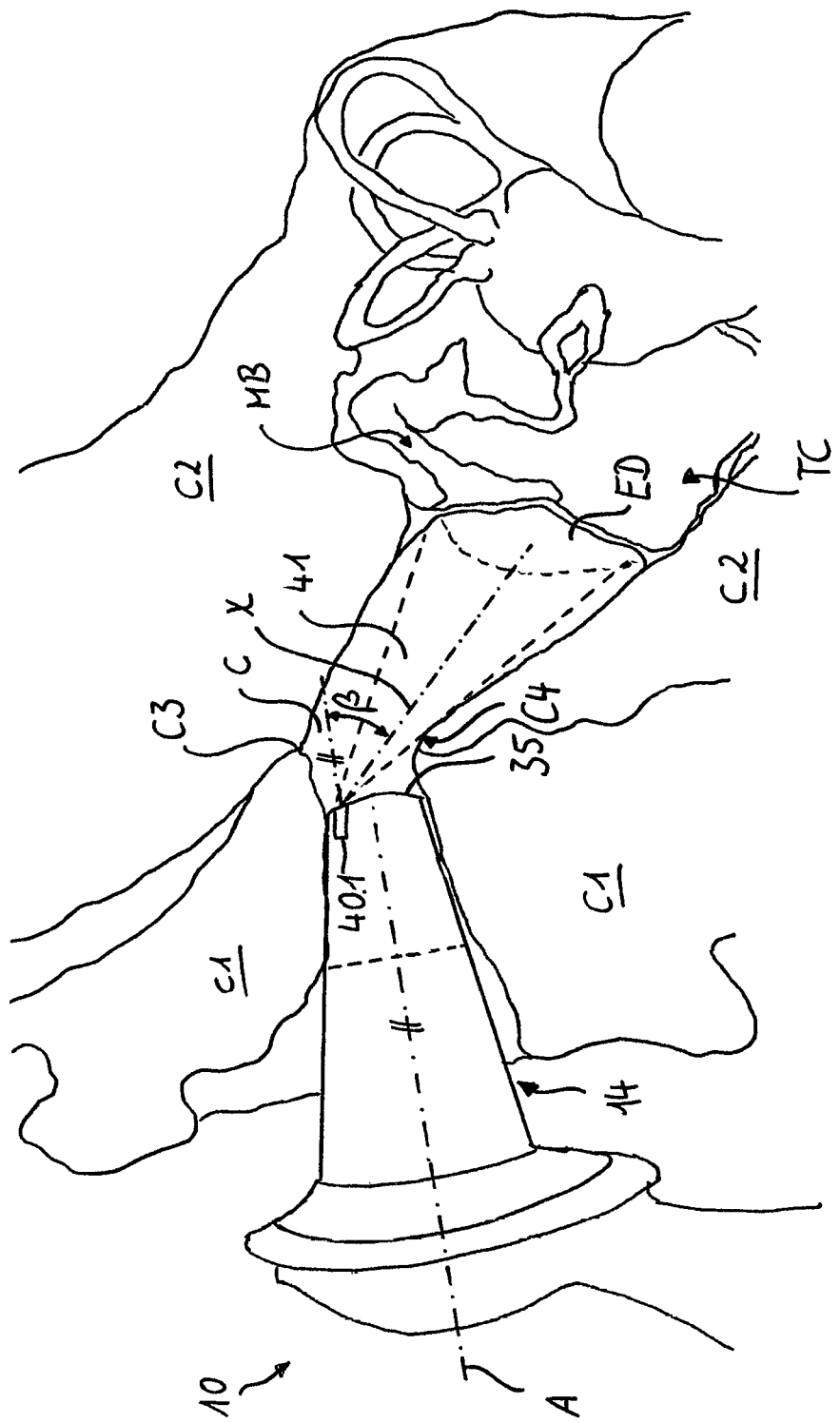
FIG. 5 schematically shows an otoscope which can be used for a method according to the present invention, with its head portion introduced into the patient's ear canal.

In FIG. 5, an otoscope 10 with a head portion 14 including an electronic imaging unit comprising a camera 40.1 is shown, wherein the camera 40.1 is positioned eccentrically (i.e. radially offset) with respect to a longitudinal axis A of the head portion 14. The eccentricity (the radial offset) is, e.g., in the range of 1.5 mm to 2 mm. The head portion 14 is introduced in the ear canal C, and the outer surface of the head portion 14 or a probe cover (not shown) is in contact with the soft connective tissue C1. In contrast to the hard bone C2 confining the ear canal C in a section which is closed to the eardrum ED, the soft connective tissue C1 is elastic and can be widened by the head portion 14.

The eardrum ED partitions off the ear canal C of the outer ear from the tympanic cavity TC. Within the tympanic cavity TC, behind the eardrum ED, the malleus bone MC contacting the eardrum ED is arranged.

The camera 40.1 has a field of vision 41 which is preferably conical. Geometrically, the field of vision 41 can be describes as a conus with an opening angle in the range of at least 80°, preferably of at least 110, e.g. 120°. The camera 40.1 preferably is a wide angle color video camera. An optical axis X of the camera 40.1 is arranged (or can optionally be arranged) at an angle β with respect to the longitudinal axis A, allowing the device to "look around the corner" effectively. The angle β preferably is in the range of 10° to 50°. The tilted arrangement can be provided in addition to a field of vision with a wide angle. The angle β can be fixed or can be variable. The camera 40.1 is arranged to "look around the corner", in order to scan the ear drum ED from an observation point being relatively far away from the eardrum ED. For this purpose, the camera 40.1 is arranged radially offset or positioned at the side of the ear canal which exhibits a relatively large radius of curvature.

In FIG. 5, the anatomy of an ear canal C is shown, the ear canal exhibiting a curvature C4. The curvature C4, which is typical for a large percentage of different shapes of the ear canal, forms a kind of "corner". As the camera 40.1 is arranged to "look around the corner", it is not required to introduce the distal tip 35 of the head portion 14 as far as a transition area or transition point C3 between soft connective tissue C1 and hard bone C2 confining the ear canal C. In other words: it is not required to introduce the distal tip 35 of the head portion 14 as far as a transition area C3 in which the ear canal C has a curvature C4 or a particularly small radius of curvature. Also, it is not required to introduce the distal tip 35 as far as the hard bone C2, i.e. the bony or osseous part of the ear canal C2. In particular, a distance of at least 10 mm, preferably at least 15 mm or even more can be kept between the distal tip 35 and the eardrum ED. This facilitates use of the otoscope 10 by laypersons. Furthermore, a mechanical manipulation of "straightening" the ear canal C is not required. In contrast to commonly used otoscopes, application of the inventive otoscope 10 does not necessarily require assistance by a medical practitioner.

As shown in FIG. 5, the diameter of the head portion 14 is defined such that the distal tip of the head portion 14 does not fit into the section of the ear canal C which is confined by hard bone C2. In particular, it has been found that in average (male and female persons), the external ear canal has a diameter of about 4.8 mm±0.5 mm. A summary referring to the average diameters of men can be found in: Salvinelli F, Maurizi M et al.; Scand. Audiol. 1991; 20(4): 253-6.

Figure 6:
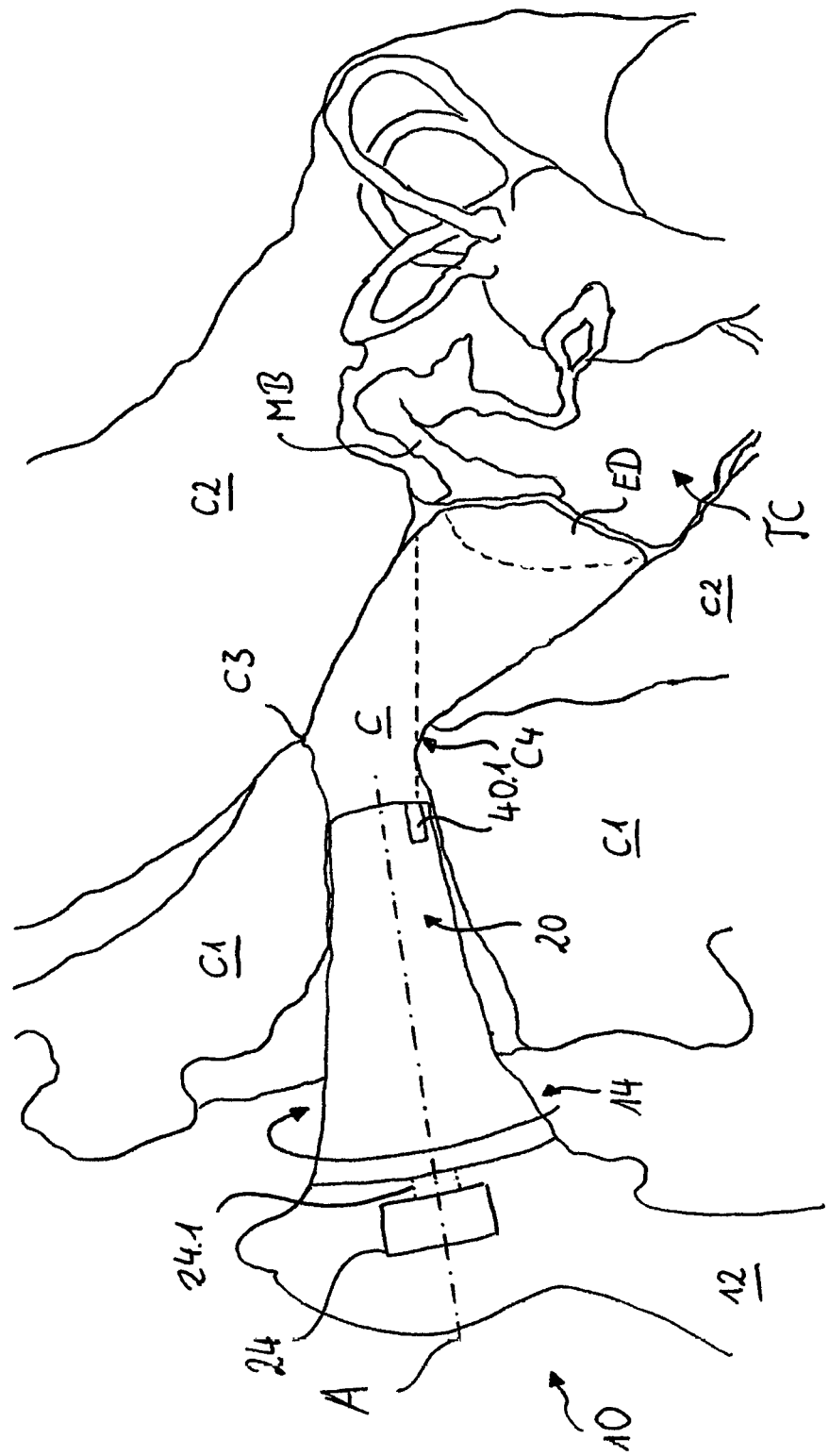
FIG. 6 shows an otoscope which can be used for a method according to the present invention, with its head portion introduced into the patient's ear canal, and with a camera positioned in a first position.

FIG. 6 shows an otoscope 10 with a head portion 14 which can be rotated around a longitudinal axis A of the otoscope 10. An electronic imaging unit comprises a camera 40.1 which is positioned radially offset from the longitudinal axis A. The camera 40.1 is positioned at a distal tip of the head portion 14. In a position (first position) as shown in FIG. 6, the camera 40.1 cannot scan the ear drum ED yet. The camera 40.1 is not in optical communication with the ear drum ED yet. Rather, a curvature C4 of the ear canal C obstructs any optical communication, as illustrated by the dashed line. In the first position as shown in FIG. 6, the ear drum ED cannot be seen at all by the camera 40.1. In order to ensure optical communication with the ear drum ED, firstly, the (radial) position of the camera 40.1 within the ear canal C has to be corrected. This can be done by rotating the head portion 14 or a part of the head portion 14 around the longitudinal axis A, especially without further motion, especially rotation, of a handle portion 12 of the otoscope 10. For this purpose, the otoscope 10 is provided with a motion mechanism 24. The motion mechanism 24 is arranged within the handle portion 12. The motion mechanism 24 includes a drive shaft 24.1 which connects the movable portion 20 with the handle portion 12. The movable portion 20 is supported by a bearing 28, as shown in detail in FIG. 8.

Figure 7:
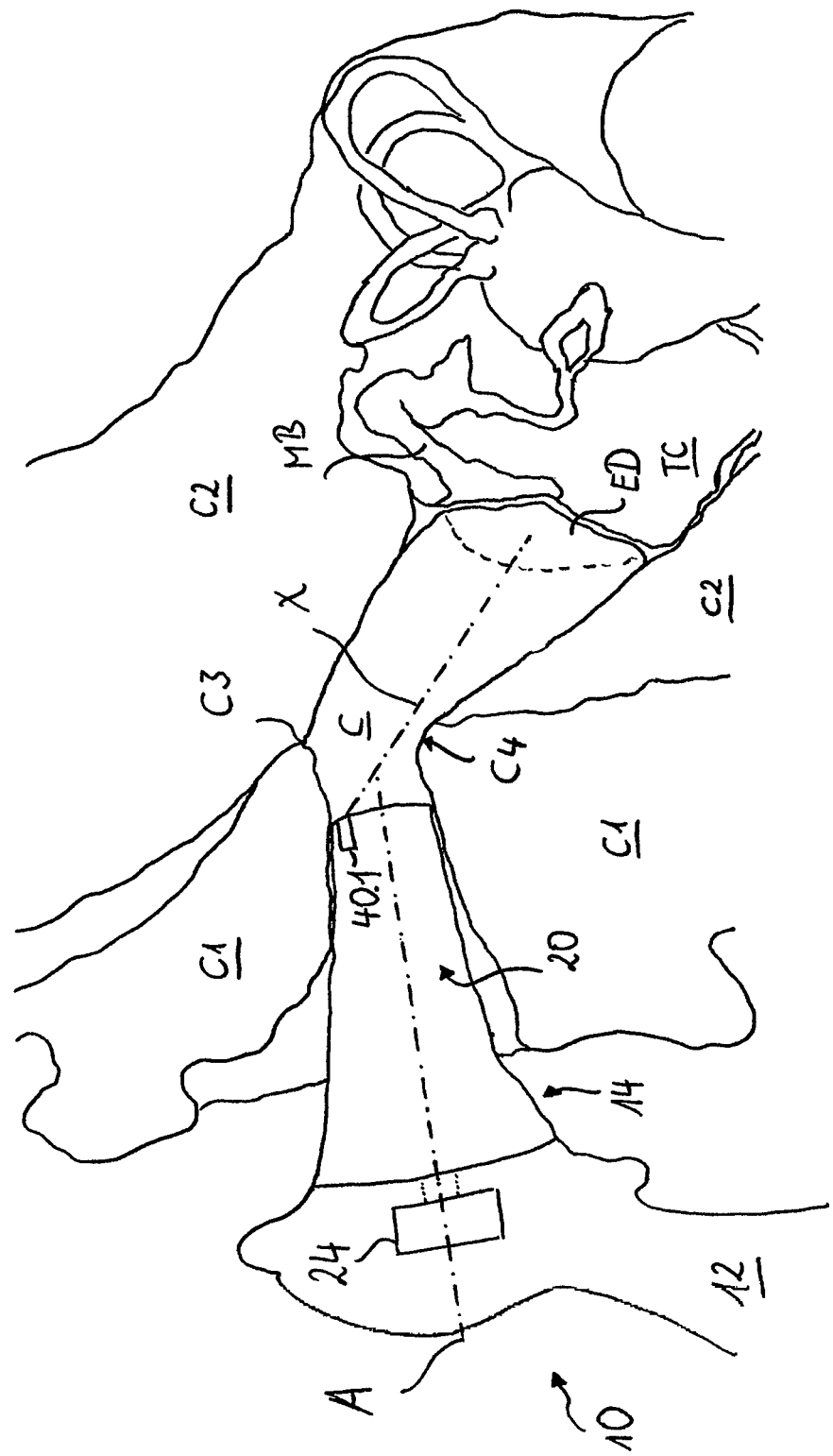
FIG. 7 shows the otoscope according to FIG. 6, with the camera positioned in a second position.

FIG. 7 shows the camera 40.1 in a position in which an optical axis X of the camera 40.1 can be directed on the ear drum ED, although the distal tip of the head portion 14 is not introduced as far as a transition point C3 between the soft connective tissue C1 and the hard bone C2. The camera 40.1 has been rotated in the second position shown in FIG. 7.

Rotation of the camera 40.1 can be carried out as described in the following. A movable portion 20 of the head portion 14 can be attached to a servo motor (not shown), e.g. a small standard servo motor (e.g. Modelcraft Micro-Servo MC1811 JR). The servo motor is arranged to turn the movable portion 20, especially by up to 180°. The servo motor has a height of e.g. about 2 cm and can be arranged directly on the axis of the rotating movable portion 20. The servo motor can exhibit a turning part that exceeds a motor housing by some millimeters. The servo motor can be attached to a chassis of the otoscope by means of a metal part which is designed to be firmly held aligned with the movable portion 20 hold by a bearing. One or more light guides (not shown) and a cable (not shown) can be connected to a printed circuit board (not shown). The cable can be directly soldered to the printed circuit board while the light guides can be directly mounted on light sources (not shown).

Figure 8:
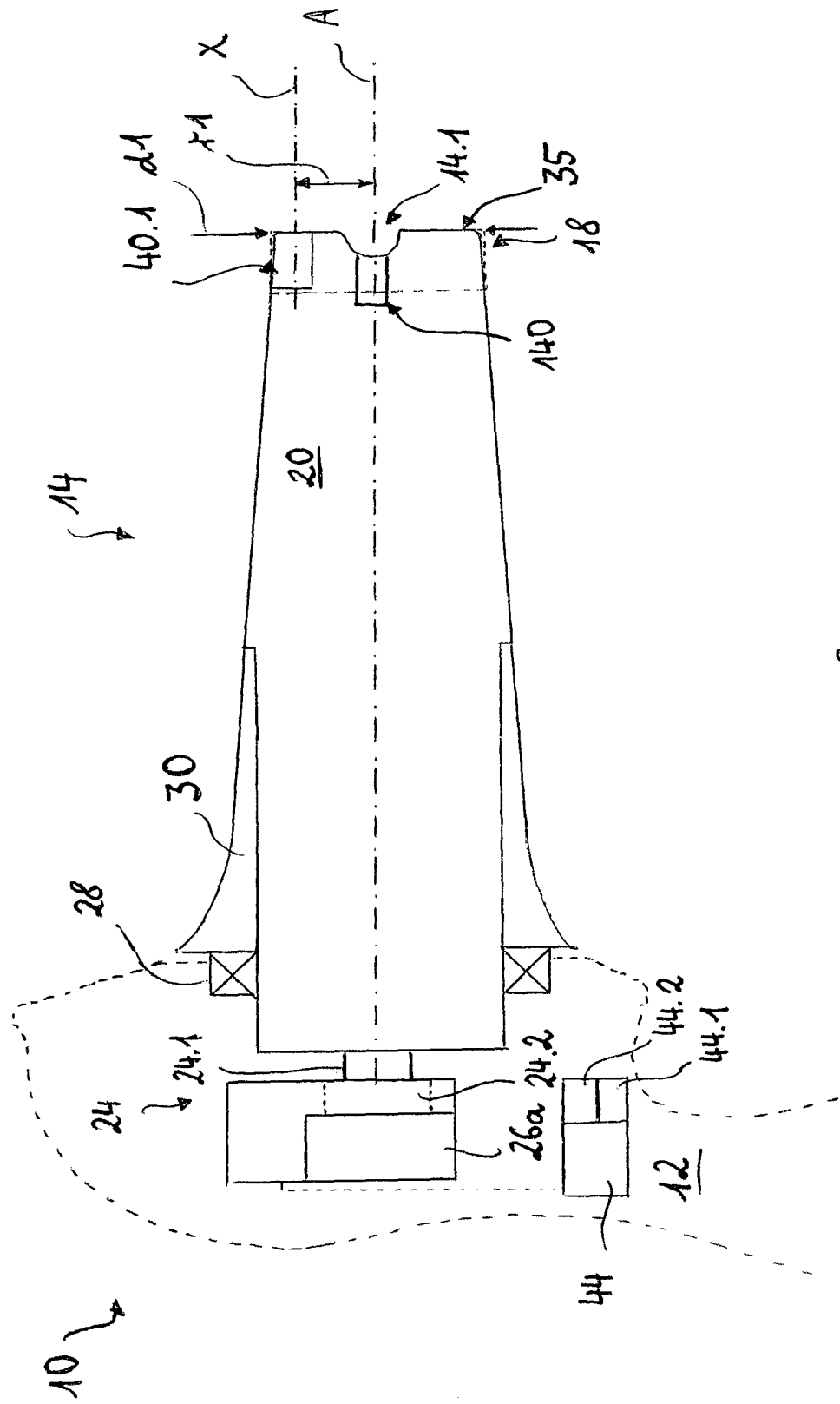
FIG. 8 schematically shows a cross-sectional view of a head portion and of a part of a handle portion of a further embodiment of an otoscope which can be used for a method according to the present invention.

FIG. 8 shows an otoscope 10 with a handle portion 12 and a head portion 14. The head portion includes a movable portion 20 and a support structure 30. The movable portion 20 can be rotated by a motion mechanism 24 which is arranged in the handle portion 12. The movable portion 20 can be rotated with respect to the support structure 30, wherein classical bearings can be used. The motion mechanism 24 includes a drive shaft 24.1 which connects the movable portion 20 with the handle portion 12. The motion mechanism 24 includes a brushless motor 26*a* which is connected to the drive shaft 24.1. Optionally, a gear 24.2 is provided between the motor 26*a* and the drive shaft 24.1. Preferably, the gear 24.2 is a worm gear, especially in order to reduce acoustic emission. The movable portion 20 is supported by the bearing 28 which itself is supported by the handle portion 12. The support structure 30 is supported by the handle portion 12. The support structure 30 provides a portion of the outer lateral surface of the head portion 14. In other words: the shape of the head portion 14 is partially defined by the support structure 30. In particular, the shape of a proximal portion of the head portion 14 is defined by the support structure 30. The support structure 30 is fixed at the handle portion 12 my means of the bearing 28.

The head portion 14 has a distal end 18 including a distal tip 35, wherein the distal end 18 has concial shape or a cylindrical shape (as indicated by the dashed line). An infrared sensor unit 140 is positioned centrically at the distal end 18. This position is only illustrated as an example. The infrared sensor unit 140 shown in FIG. 8 can be provided in conjunction with the other embodiments of the otoscopes as described in the preceding or following figures also. The distal end 18 is provided with an indentation 35 for accommodating a portion of a probe cover (not shown). A camera 40.1 having an optical axis X is arranged radially offset with respect to a longitudinal axis A of the head portion 14, wherein the radial offset r1 of the optical axis X preferably is in a range between 1.5 mm and 2 mm. The camera 40.1 is arranged adjacent to an inner lateral surface of the distal end 18. Preferably, the camera 40.1 is in contact with the inner lateral surface of the distal end 18.

The otoscope 10 comprises a logic unit 44. The logic unit 44 can be arranged for determining the distance of any objects within the ear canal, especially with respect to the distal tip 35, and/or for determining an angle of any objects, especially an angle with respect to an inner lateral surface of the ear canal or a longitudinal axis of the ear canal. As an alternative, the logic unit 44 can comprise means 44.1 for determining the distance and/or means 44.2 for determining the angle.

In the FIGS. 6, 7 and 8, a probe cover is not shown. According to the present invention, a probe cover either can be rotated together with the head portion or can be stationary. Preferably, the probe cover is not rotated, i.e. the probe cover is stationary.

Figure 9A:
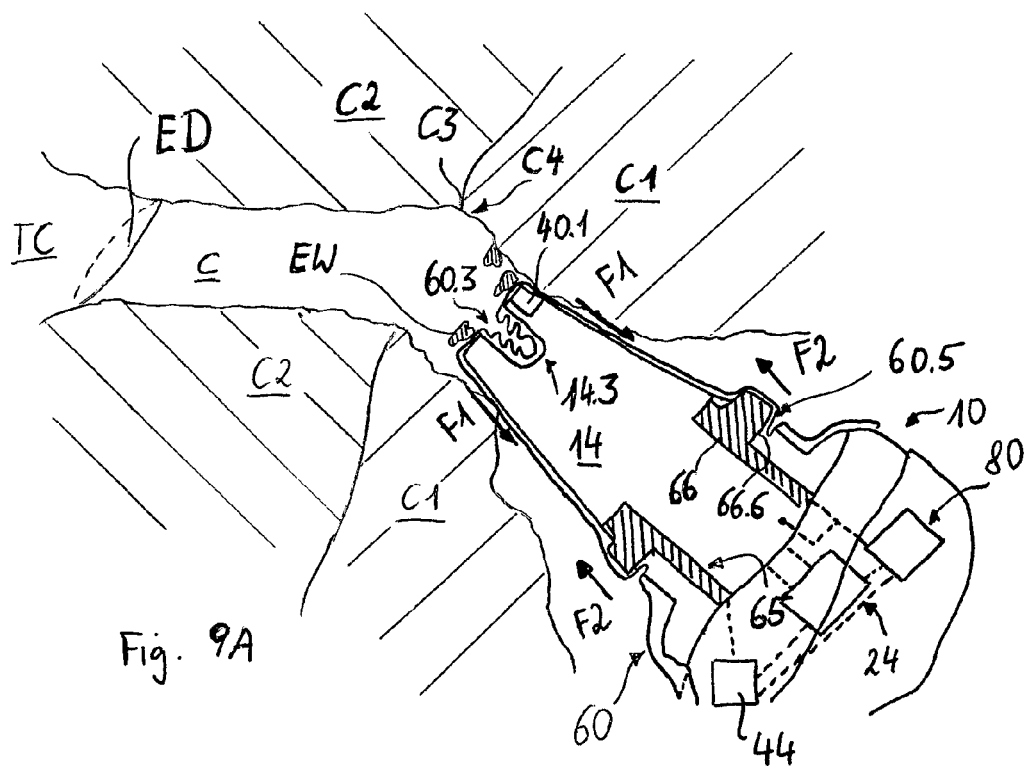
FIGS. 9A and 9B schematically show cross-sectional views of a probe cover arranged on a head portion of a further embodiment of an otoscope which can be used for a method according to the present invention, the head portion being positioned in a first and second position within an ear canal.

FIG. 9A shows a head portion of an otoscope 10 which is arranged within an ear canal C. The ear canal C is partly surrounded or confined by soft connective tissue C1 and— further down towards the ear drum ED—partly by hard bone C2. In order to appropriately observe the ear drum ED, the head portion 14 has to be introduced as far as a curvature C4 which is located at a transition point C3 between the soft connective tissue C1 and the hard bone C2. A camera 40.1 is arranged with a radial offset within the head portion 14.

The otoscope 10 exhibits a motion mechanism 24 which is arranged for displacing the camera 40.1 and/or any light source (not shown). Further, a moving mechanism 65 is arranged within the head portion 14. Both the motion mechanism 24 and the moving mechanism 65 are coupled to a logic unit 44 which is arranged for controlling the mechanisms 24, 65, be it separately or be it in dependence on each other. The moving mechanism 65 exhibits an adapter 66 having a shoulder 66.6. The adapter 66 is shown in a first position. A probe cover 60 exhibiting a probe cover reservoir 60.3 is provided over the head portion 14. The head portion 14 exhibits a groove or indentation 14.3 for accommodating the probe cover reservoir 60.3. The probe cover 60 exhibits a U-shaped or sigmoid shaped section or inward protrusion which engages or encompasses the shoulder 66.6 such that the probe cover 60 can be positioned axially by means of the moving mechanism 65. The axial position of the probe cover 60 can be defined by the moving mechanism 65, i.e. by the axial position of the adapter 66.

Ear wax EW and/or other objects are partially obstructing the ear canal C. In particular, ear wax EW adheres on the outer surface of the probe cover 60 and obstructs optical communication of the camera 40.1 with the ear drum ED.

Figure 9B:
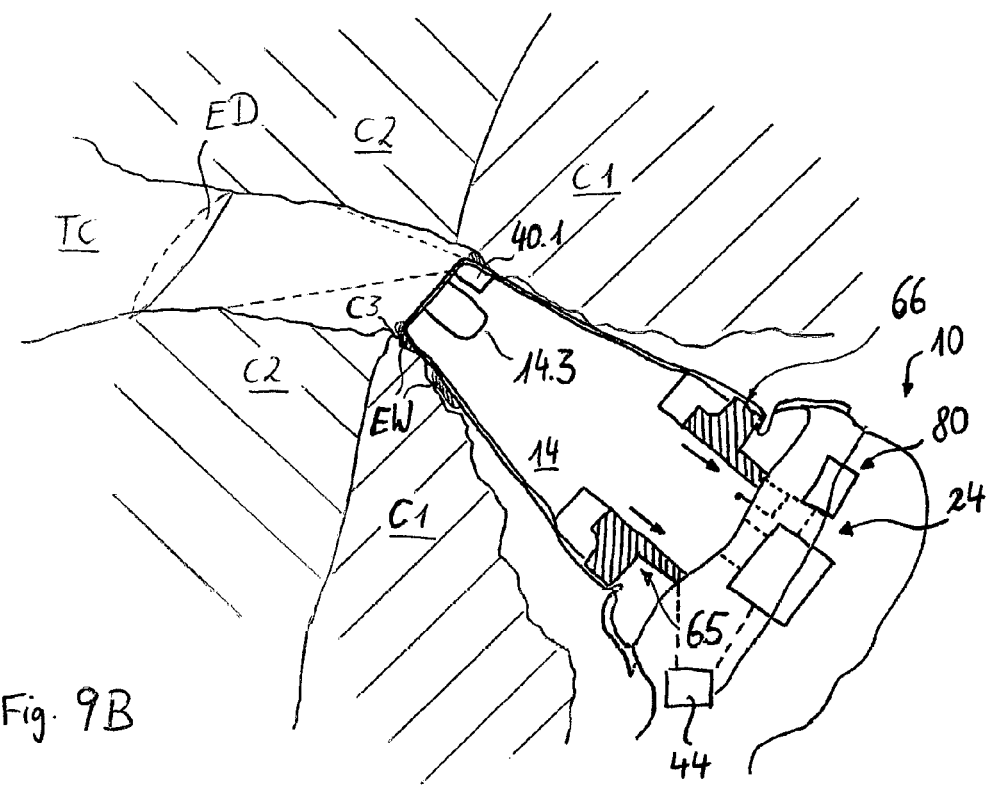

FIG. 9B shows the head portion 14 in a second position within the ear canal. The distal tip of the head portion 14 is introduced as far as the transition point C3. The probe cover 60 and the adapter 66 have been displaced in a proximal direction, as indicated by the two arrow heads. Thereby, a pulling force in the proximal direction is exerted on the probe cover 60. The adapter 66 is shown in a second axial position. The probe cover reservoir 60.3 has been pulled out of the indentation 14.3. The reservoir 60.3 has been displaced from the distal tip towards a lateral surface of the head portion 14, at least partially. Thereby, ear wax EW has been displaced towards the lateral surface, too. The field of vision of the camera 40.1 is not obstructed by any ear wax any more.

In the positions shown in FIGS. 9A and 9B, detection of a force exerted on the probe cover 60 or the head portion 14 can be carried out, especially by force detection means 80 which are coupled to the moving mechanism 65, especially the adapter 66, and/or to the head portion 14. The force detection means 80 are coupled to the logic unit 44 and/or the motion mechanism 24.

There is a friction force F1 exerted between tissue, especially the soft connective tissue C1, and the outer lateral surface of the probe cover 60. A force F2, especially an introducing or insertion force, is exerted from the head portion 14 on the probe cover 60. The moving mechanism 65 can provide a reaction force (corresponding to the insertion force F2), especially in order to determine a threshold value for an axial force which has to be exceeded in order to axially displace the probe cover in the proximal direction with respect to the head portion. The force detection means 80 may be arranged for releasing the moving mechanism 65, especially at a time the threshold value is exceeded. Alternatively or in addition, the moving mechanism 65 may exhibit a latch mechanism which can be released upon a specific force. The force detection means 80 may exhibit a force sensor, e.g. any common force sensor arranged for detection a compression force.

Figure 10:
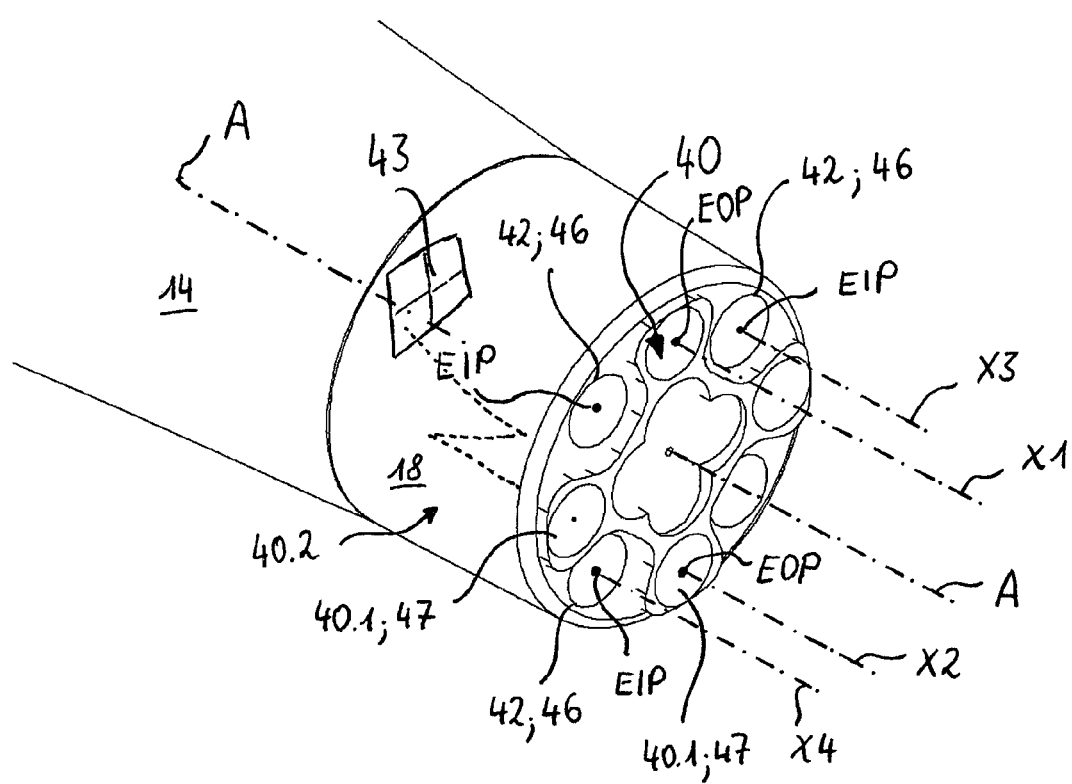
FIG. 10 schematically shows a perspective side view of a head portion of an otoscope which can be used for a method according to the present invention.

FIG. 10 shows a head portion 14 of an otoscope, wherein at a distal end 18, an electronic imaging unit 40 is arranged. The electronic imaging unit 40 exhibits a plurality of optical axes X1, X2 as well as a plurality of illumination axes X3, X4, each axis X1, X2, X3, X4 being arranged radially offset with respect to a longitudinal axis A of the head portion 14. The plurality of optical axis X1, X2 may be provided by beam splitter optics 40.2 of the electronic imaging unit 40, at least partially. The radial position of the illumination axes X3, X4 can be defined by an eccentric illumination point EIP, respectively. The radial position of the optical axes X1, X2 can be defined by an eccentric observation point EOP, respectively. The beam splitter optics 40.2 may comprise a plurality of lenses 47 and/or mirrors which are configured for providing radially offset (eccentric) observation points EOP (as schematically illustrated by the dashed line). The beam splitter optics 40.2 optically couple the lenses 47 with an image sensor 43. The respective eccentric illumination point EIP is centrically arranged at a front surface of a light guide 42 or light source or LED 46. The respective eccentric observation point EOP is centrically arranged at a front surface of a camera 40.1 or any other optical component or lens 47 of the electronic imaging unit 40. The optical components 47 can be in optical communication with the single image sensor 43 of the electronic imaging unit 40, which is preferably centrically arranged, as schematically illustrated in FIG. 10. The image sensor 43 may be provided with different sections or segments, e.g. four segments (as schematically illustrated), in order to provide one section for one optical axis, respectively.

Figure 11:
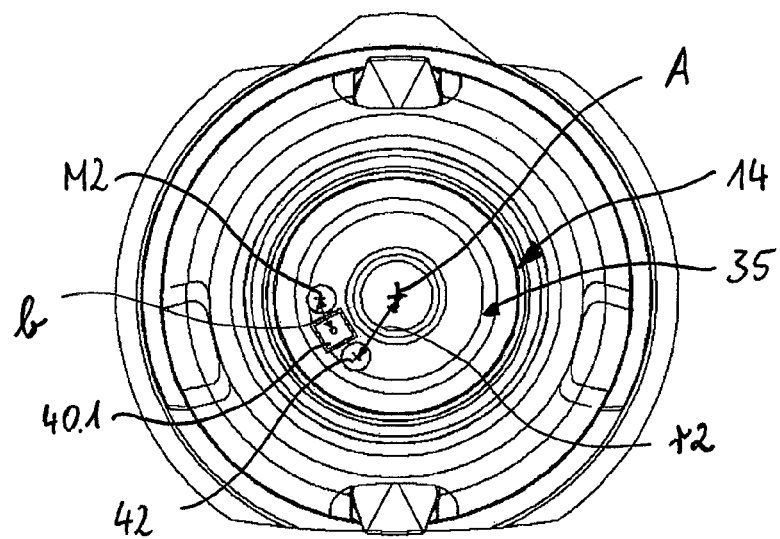
FIG. 11 schematically shows a front view of a head portion of an otoscope which may be used for a method according to the present invention, wherein the radial position of light sources and a camera of the otoscope is illustrated.

FIG. 11 shows a head portion 14 accommodating an electronic imaging unit 40 which comprises one single camera 40.1. The camera 40.1 is positioned radially offset with a maximum radial offset at a distal tip 35 of the head portion 14. Two light guides or light sources 42 (e.g. LEDs) are arranged adjacent to the camera 40.1, especially on the same pitch circle as the camera 40.1. The light sources 42 are arranged with a radial offset r2 which corresponds to a radial distance between a longitudinal (middle) axis A of the head portion 14 and a middle axis M2 of the respective light source 42. In particular, the radial offset r2 of the light sources 42 can correspond to the radial offset of the camera 40.1 or, as an alternative, is even larger than the radial offset of the camera 40.1.

Preferably, the camera 40.1 can be rotated by a motion mechanism (not shown), especially together with the light guides 42 or at least the distal ends of the light guides 42. The diameter of the light guides 42 is in a range between 0.2 and 1.5 mm, preferably 0.7 mm and 1.2 mm, especially 1.0 mm. The (eccentric) radial distance or offset r2 is in the range of 1.8 mm to 2.5 mm, preferably 1.9 mm to 2.3 mm, further preferable 2.0 mm to 2.1 mm, depending on the diameter of the light guides 42. The two light guides 42 are arranged adjacent to the camera 40.1 in a distance b to the camera, wherein the distance b corresponds to the length of (a part of) a circular arc of the pitch circle on which the camera 40.1 and the two light guides 42 are arranged. The distance b is measured between a middle axis of the camera 40.1 and the middle axis M2 of the respective light guide 42. Preferably, the distance b is in the range of 0.5 mm to 2 mm, more preferable 0.8 mm to 1.8 mm, especially about 1.5 mm.

Figure 12:
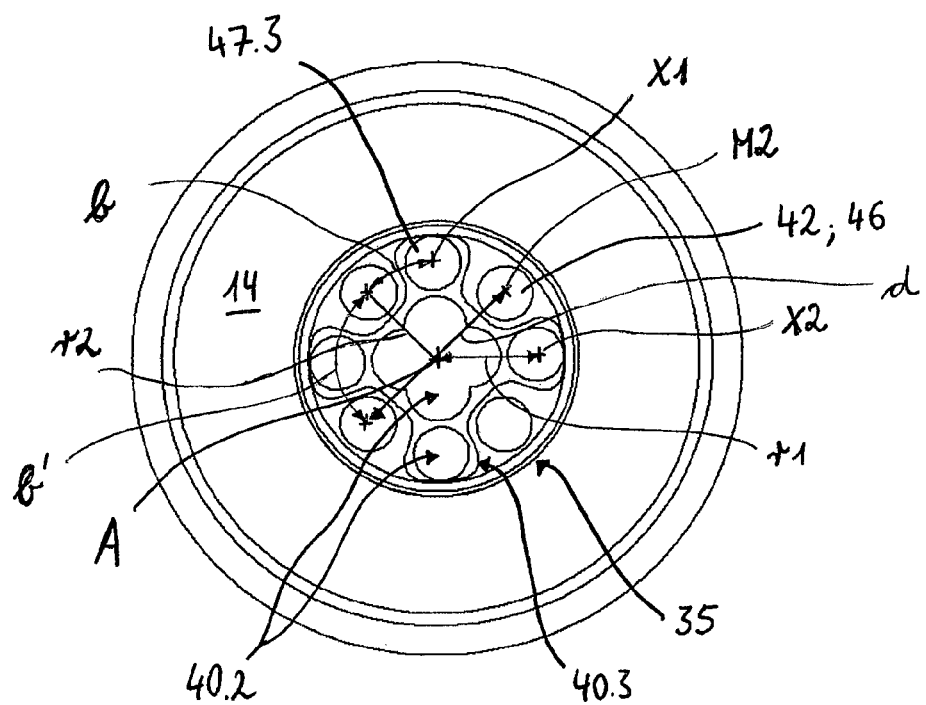
FIG. 12 schematically shows a front view of a head portion of an otoscope which may be used for a method according to the present invention, wherein the radial position of light sources and a plurality of optical axes of the otoscope is illustrated.

FIG. 12 shows a head portion 14 with a distal tip 35. An electronic imaging unit is positioned within the distal tip 35. The electronic imaging unit 40 comprises beam splitter optics 40.2 which exhibit a plurality of lenses or optical surfaces 47.3 (especially sixteen lenses or optical surfaces), from which eight are shown in FIG. 12. The beam splitter optics 40.2 provide four different optical paths X1, X2. Each optical path is defined by four optical surfaces. Those lenses which define an optical path are arranged in the same plane, respectively. Four light guides or light sources 42 or LEDs 46 are arranged between the lenses 47.3, respectively. The light guides 42 or LEDs 46 are arranged adjacent to the lenses 47.3 having the largest radial offset, especially in a distance b to each lens 47.3. The distance b corresponds to the length of a circular arc of a pitch circle on which the lenses 47.3 and the light guides 42 are arranged. The distance b is measured between a middle axis of the respective to the lens 47.3 and a middle axis M2 of the respective light guide 42. Preferably, the distance b is smaller than 2 mm, e.g. 1.5 mm, more preferable smaller than 1.5 mm, e.g. 1.35 mm, further preferable smaller than 1.3 mm, especially between 1 mm and 1.3 mm, depending on the diameter of the light guides 42.

An outer lateral surface of a support 40.3 accommodating the lenses is arranged adjacent to an inner lateral surface of the distal tip 35. The outer lateral surface of the support 40.3 touches the inner lateral surface, in particular at four different sections. The light sources 42 or LEDs 46 are arranged within recesses or grooves 40.3a of the support 40.3.

The light sources 42 are arranged with a radial offset r2 which corresponds to a radial distance between a longitudinal (middle) axis A of the head portion 14 and a middle axis M2 of the respective light source 42. In particular, the radial offset r2 of the light sources 42 can correspond to the radial offset of the camera 40.1 or, as an alternative, is even larger than the radial offset of the camera 40.1. The (eccentric) radial distance or offset r2 is in the range of 1.8 mm to 2.5 mm, preferably 1.9 mm to 2.3 mm, further preferable 2.0 mm to 2.1 mm, depending on the diameter of the light guides 42.

Two of the light sources 42 or LEDs 46 are arranged in a distance b' to each other, respectively. The distance b' corresponds to the length of (a part of) a circular arc of the pitch circle on which the light sources 42 or LEDs 46 are arranged. Preferably, the distance b' is in a range between 5 mm and 3 mm, e.g. 4 mm, more preferable between 3.5 mm and 4.5 mm. With such an arrangement, light can be provided effectively, especially by two of the light guides 42 or LEDs 46 with respect to one of the lenses 47.3. In particular, by means of the arrangement of four light sources 42 in conjunction with four optical axes X1, X2 shown in FIG. 12, an ear canal can be observed substantially independent of the exact position of the respective lens 47.3 or light source 42 or LED 46 within the ear canal.

At least two of the light sources or light guides 42 or LEDs 46 are arranged in a maximum distance d apart from each other. The maximum distance d is measured between the middle axes M2 of the respective light guides 42. Preferably, the maximum distance d is at least 3.5 mm, more preferable at least 4 mm, further preferred in a range between 4.2 mm and 4.6 mm. This relatively large distance d facilitates stereoscopic viewing, especially by emitting light from two points which are most distant from each other, in order to analyse reflected light which is reflected from different directions. This relatively large distance d also facilitates evaluation of depth information, which can be helpful in order to distinguish the eardrum from any objects (e.g. ear wax) within the ear canal.

FIG. 13A shows an ear canal C which has an S-shaped (sigmoid) form with a first curvature C4' and a second curvature C4, the second curvature C4 being closer to the ear drum ED than the first curvature C4'. A head portion 14 of an otoscope 10 is introduced within the ear canal C. In the position shown in FIG. 13A, the second curvature C4 of the ear canal C obstructs any optical communication of a distal end 18 of the head portion 14 with the ear drum ED.

In FIG. 13A, the section of the ear canal C which is confined by hard bone C2 exhibits a straight-line geometry characterized by a longitudinal axis C5. This section is confined by an inner lateral surface C6. The eardrum ED is arranged at an angle of about 40° to 50° with respect to the inner lateral surface C6 or with respect to the longitudinal axis C5 of the ear canal C.

From the position shown in FIG. 13B, the eardrum ED can be observed entirely, i.e. in its entirety. The eardrum ED can be observed entirely from an eccentric observation point EOP which is arranged on an optical axis of an electronic imaging unit (not shown) arranged at the distal tip of the head portion 14. Likewise, the eardrum ED can be illuminated entirely from an eccentric illumination point EIP. But, it is not even required introducing the head portion 14 as far as to the position shown in FIG. 13B. The otoscope 10 is introduced within the ear canal C as far as the second curvature C4, i.e. nearly as far as a transition area C3 between soft connective tissue C1 and hard bone C2. In the position shown in FIG. 13B, the otoscope 10 is able to "look around the corner". The "corner" can be defined as the second curvature C4 of the ear canal C.

Likewise as shown in FIG. 5, the diameter of the head portion 14 can be shaped such that it does not fit into the section of the ear canal C which is confined by hard bone C2. FIG. 13A only illustrates or refers to the relative axial position of the head portion 14, but not to any preferred diameter of the head portion 14. In particular, the outer diameter of the head portion 14, especially at the distal tip, preferably is bigger than the inner diameter of the section of the ear canal C which is confined by hard bone C2.

A distal tip 35 or front surface of the head portion 14 is arranged at an angle with respect to the inner lateral surface C6 or with respect to the longitudinal axis C5 of the ear canal C which is smaller than the respective angle at which the eardrum ED is arranged.

Figure 14:
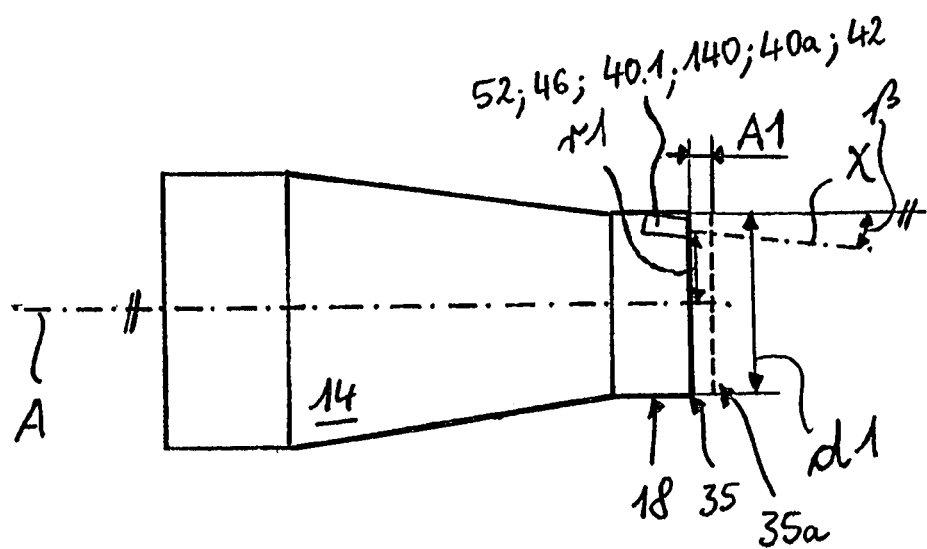
FIG. 14 schematically shows a head portion of an ear inspection device according to the present invention, the head portion exhibiting a cylindrical distal end.

FIG. 14 shows a head portion 14 exhibiting a distal end 18 or distal tip 35 having a diameter d1. The diameter d1 is in the range of 4.7 mm to 5.2 mm, preferably 4.8 mm to 5 mm, especially 4.9 mm. The distal end 18 has a cylindrical shape. At least one camera 40.1 and/or infrared sensor unit 52; 140 and/or light guide 42 or light source 46 and/or mobility sensor unit 40a is arranged radially offset with a radial offset r1 with respect to a longitudinal axis A of the head portion 14. The camera 40.1 or the respective device has an optical axis X. The camera 40.1 and its optical axis X are tilted against the longitudinal axis A. The tilt angle β is e.g. in the range of 10° to 30°. The optical axis X is tilted with respect to a lateral surface of the distal end 18.

The at least one camera 40.1 is arranged at a most distal position, i.e. contacting or providing the distal tip 35. Exemplary, an alternative configuration is shown, the distal tip being provided in a position with a distance A1 (protruding distal tip 35a). The distance A1 is a distance between the most distal front side or front surface of the head portion 14, i.e. the protruding distal tip 35a, and the most distal (optical) component of the camera 40.1 or the infrared sensor unit 52; 140 or the light source 46. Preferably, each device is positioned at a distance A1 of less than 3 mm, preferably less than 2 mm, more preferable less than 1 mm, from the protruding distal tip 35a. This may ensure that a radial offset can provide a most eccentric position of on observation point or illumination point or temperature detection point within the ear canal.

Figure 15:
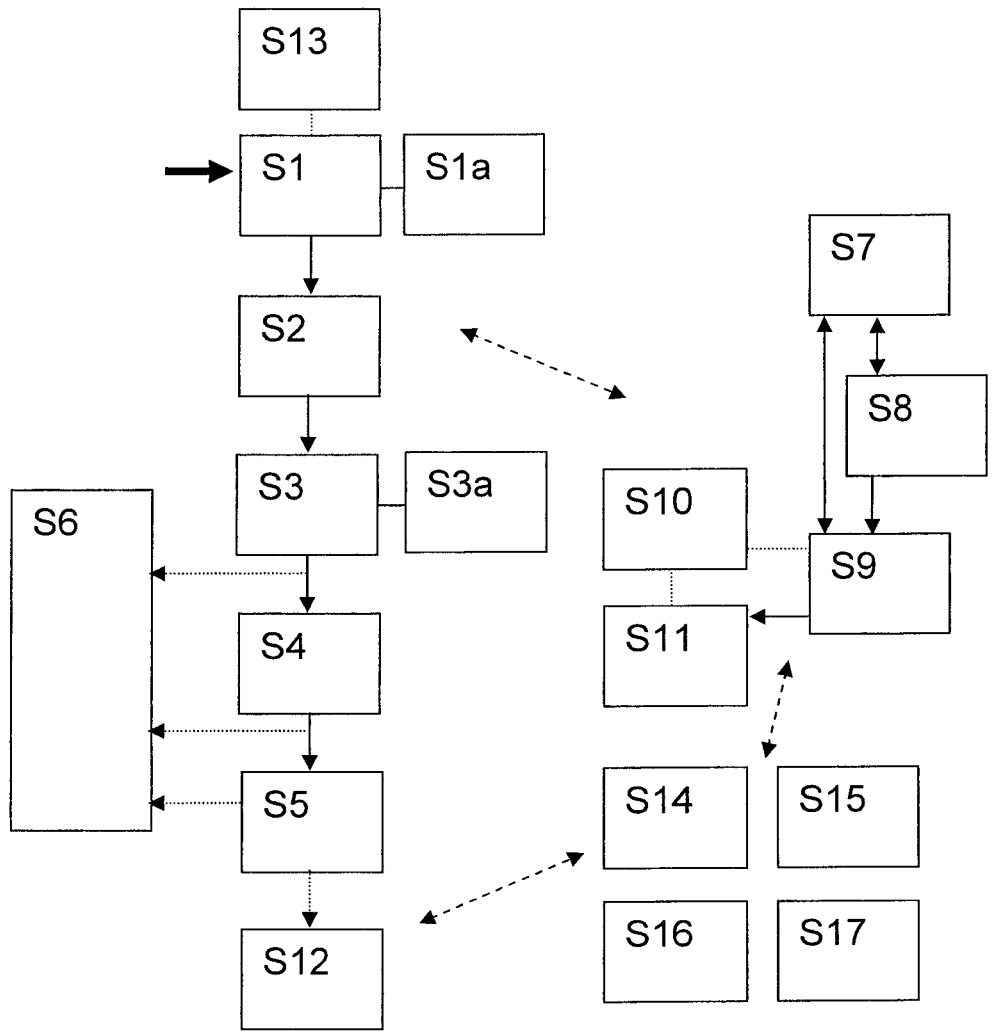
FIG. 15 schematically shows a diagram of steps of a method according to embodiments of the invention.

In FIG. 15, method steps S1 to S17 of methods according to embodiments of the invention as well as interdependencies there between are illustrated. Step S1 comprises introducing the electronic imaging unit. Step S1a comprises introducing the electronic imaging unit in conjunction with an infrared sensor unit. Step S2 comprises capturing at least one image. Step S3 comprises determining brightness and/or color information for identifying objects. Step S3a comprises detecting infrared radiation in conjunction with determining brightness and/or color information for identifying objects. Step S4 comprises comparing images. Step S5 comprises generating a calculated image. Step S6 comprises informing the user that identification of the eardrum has failed.

Step S7 comprises displacing the electronic imaging unit and/or at least one light source. Step S8 comprises tilting the electronic imaging unit or an optical axis thereof, or tilting the light source. Step S9 comprises moving the probe cover with respect to the head portion. Step S10 comprises detecting a force exerted on the probe cover or the head portion. Step S11 comprises motion detection of the probe cover. Step S12 comprises medically characterizing the eardrum. Step S13 comprises user guidance. Step S14 comprises passing a gas through the probe cover. Step S15 comprises calibration. Step S16 comprises segmented lighting. Step S17 comprises temperature measurement by means of an infrared sensor unit.

Methods according to embodiments of the invention start at step S1. Alternatively to step S1, step S1a can be carried out. Alternatively to step S3, step S3a can be carried out. Steps S1 to S6 can be carried out sequentially. Step S6 can be carried out optionally at different steps. Step S12 can be carried out optionally. Step S10 can be carried out independently or in conjunction with e.g. step S9 or S11. Steps S7 to S11 can be carried out in conjunction with each other, and in conjunction with one of steps S1 to S6 or with S12. Steps S7 and S8 can be carried out with respect to a displacement of an (optional) infrared sensor unit also. Step S13 is preferably carried out during step S1 or S1a. Steps S14 to S17 can be carried out in conjunction with each other and/or in conjunction with one of the other steps.

Figure 16:
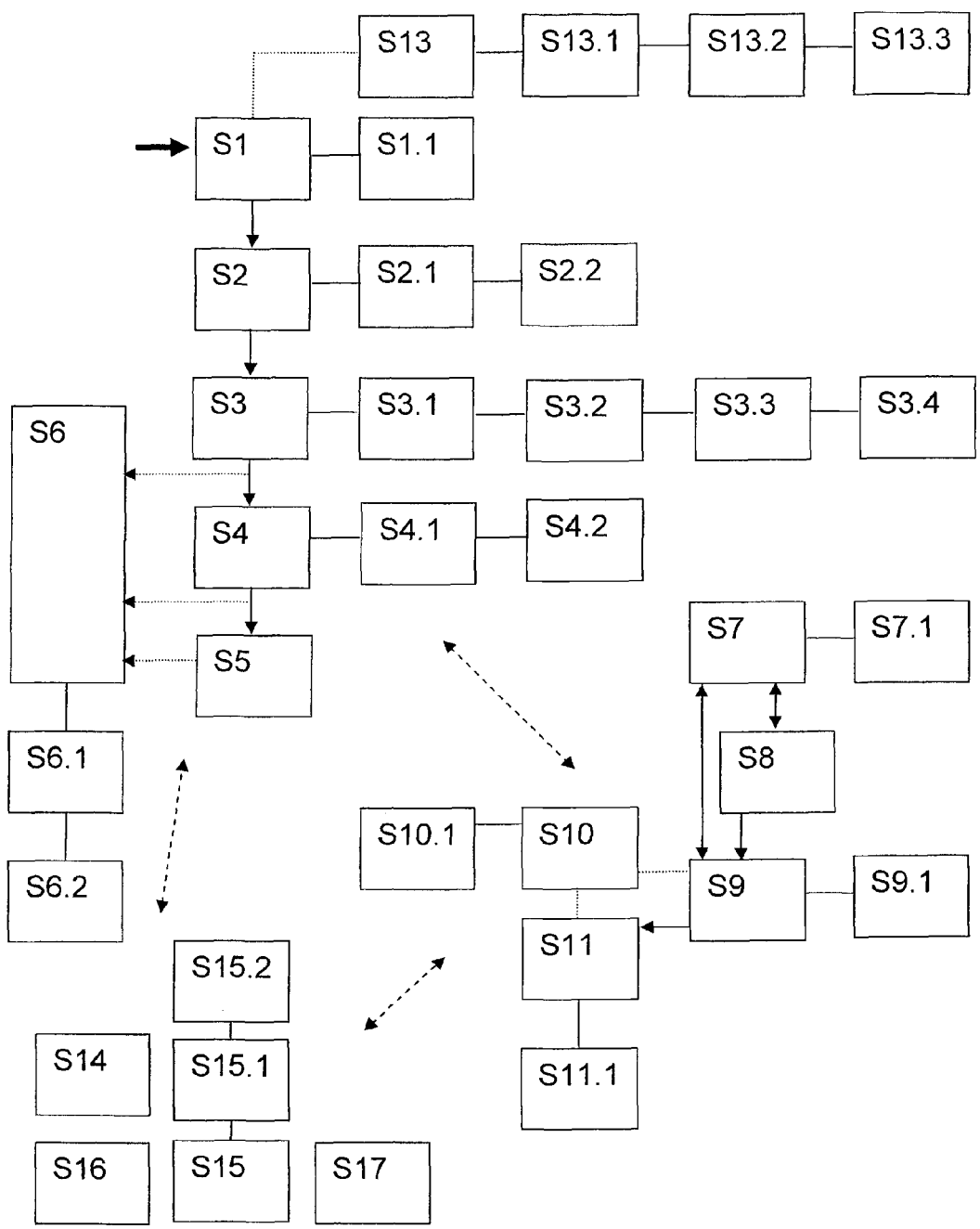
FIG. 16 schematically shows a detailed diagram of steps of methods according to embodiments of the invention.

In FIG. 16, method steps of methods according to embodiments of the invention as well as interdependencies there between are schematically illustrated in detail. In context with steps S1 to S17, it is referred to FIG. 15. In step S1, also, capturing a plurality of images within a specific time frame can be carried out. At the maximum, e.g., 60 images are captures per second, especially during displacement of the respective optical axis or camera. The step S1 can comprise the step S1.1 of introducing the electronic imaging unit no further than a predefined distance to the eardrum. The step S2 can comprise the step S2.1 of capturing at least two images from different positions and/or the step S2.2 of capturing at least two images with illumination from different positions or during illumination from different positions. The step S3 can comprise the step S3.1 of determining the spectral composition of reflections, especially the degree of reddishness, of the eardrum, or an area around the eardrum including the eardrum, and/or the step S3.2 of varying an intensity of illumination, especially for determining the degree of reddishness and/or the step S3.3 of pattern recognition, especially for identifying the eardrum, and/or the step S3.4 of determining the distance of objects, especially for identifying the eardrum. The step S4 can comprise the step S4.1 of discriminating objects by comparing their positions in images captured from different positions and/or the step S4.2 of discriminating objects by comparing their positions in images captured with illumination from different positions. The step S6 can comprise the step S6.1 of informing the user by an acoustic signal and/or the step S6.2 of informing the user by a visual signal.

The steps S1 to S6 relate to capturing images of objects. A method according to the present invention can further comprise at least one of the steps S7 to S11, wherein the steps S7 to S11 are related to a displacement of an optical component of the otoscope and/or a displacement of a probe cover and/or a displacement of an infrared sensor unit. The step S7 can comprise the step S7.1 of rotating the electronic imaging unit an/or at least one light source. The step S9 can comprise the step S9.1 of axially positioning the probe cover. The step S10 can comprise the step S10.1 of activating, especially releasing the moving mechanism in dependence on detected force. The step S11 can comprise the step S11.1 of detecting relative motion of the probe cover by the electronic imaging unit. The step S15 can comprise the step S15.1 of calibrating a spectral sensitivity of the electronic imaging unit and/or the step S15.2 of calibrating color and/or brightness of the at least one light source.

During the step S1, a user guidance can be carried out, in order to position the otoscope more easily within the ear canal, especially with a distal tip arranged in the transition area between soft connective tissue and hard bone, or at the second curvature. A user guidance can be described schematically by a step S13. The step S13 can further comprise the step S13.1. The step S13.1 includes indicating an insertion depth. The step S13 can further comprise the step S13.2. The step S13.2 includes indicating a direction of rotation. The step S13 can further comprise the step S13.3. The step S13.3 includes indicating a tilting angle of the handle portion. The steps S7, S8, S9, S10 and S11 can be carried out during any of the steps S1, S13, S2, S3, S4, S5 and S6.

As shown in FIG. 16, methods according to embodiments of the invention can be carried out without any method step of medically characterizing the eardrum. The method steps shown in FIG. 16 relate to identification of objects.

Figure 17:
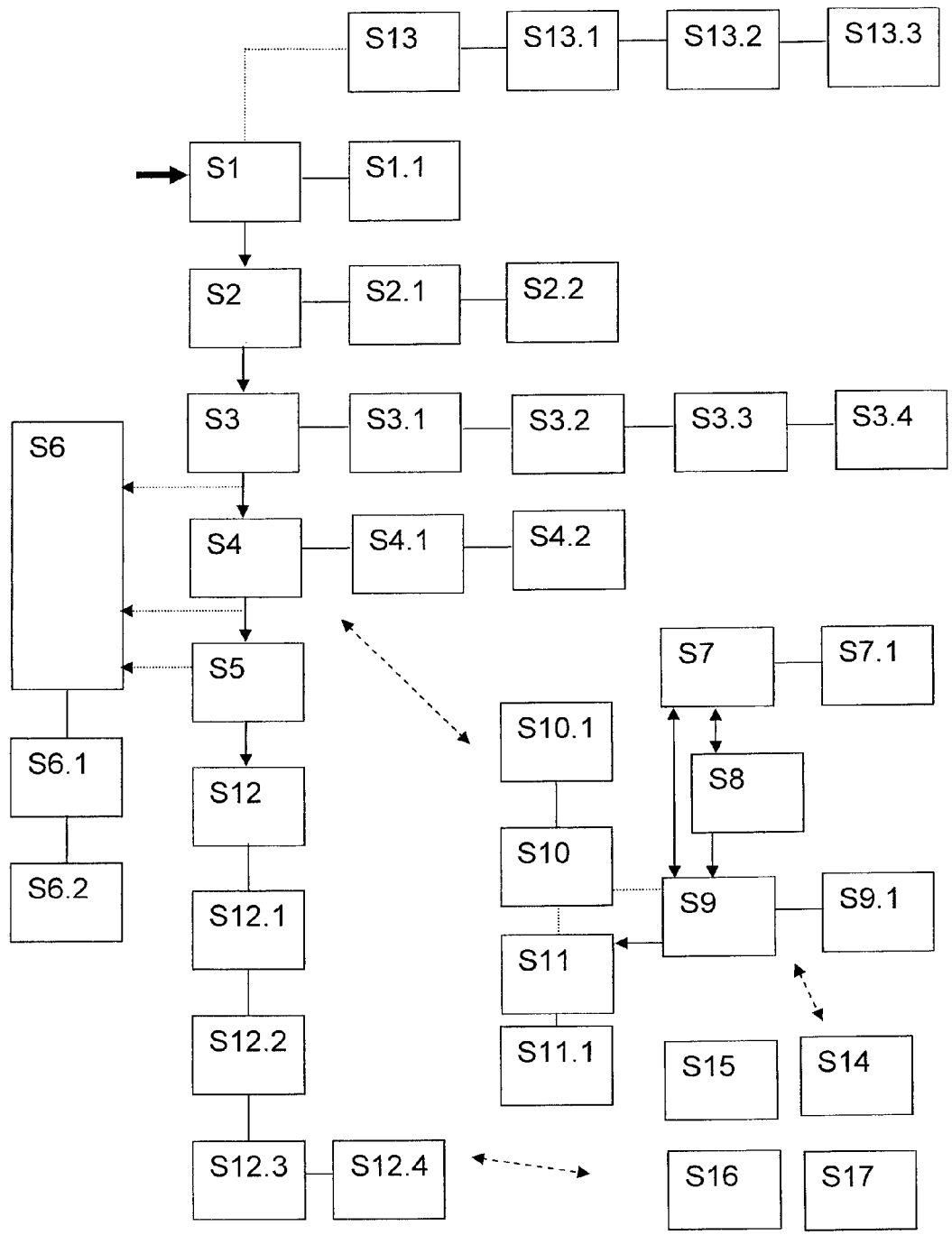
FIG. 17 schematically shows a detailed diagram of steps of methods according to further embodiments of the invention.

In FIG. 17, in addition to the method steps shown in FIG. 16, the methods according to embodiments of the invention include an additional step S12 of medically characterizing the eardrum. The step S12 includes, e.g., providing a suggestion to the user, especially a layperson, as to whether a physician should be visited or not. The step S12 includes, e.g., providing an inflammation index to the user. The step S12 can further comprise the step S12.1. The step S12.1 includes determining the degree of reddishness of the eardrum. The step S12 can further comprise the step S12.2. The step S12.2 includes identifying objects within the tympanic cavity behind the eardrum. The step S12 can further comprise the step S12.3. The step S12.3 includes determining a curvature of the ear drum. The step S12 can further comprise the step S12.4. The step S12.4 includes pressurizing the ear drum. The step S12 can further comprise the step S12.5. The step S12.5 includes determining whether the head portion is positioned within the left or the right ear.

The steps S7, S8, S9, S10, S11 and S12 can be carried out during any of the steps S1, S13, S2, S3, S4, S5 and S6 as well as during any of the steps S14 to S17.

The invention claimed is:

1. A method of identifying objects in a subject's ear, comprising:
    introducing an optical electronic imaging unit and at least one light source into an ear canal of a subject's outer ear, wherein the electronic imaging unit exhibits at least one optical axis directed in a distal direction;
    using the electronic imaging unit to capture at least one image from at least one eccentric observation point positioned on the at least one optical axis and positioned eccentrically within the ear canal; and
    determining brightness or color information to identify objects shown in the at least one image by an electronic system using pattern recognition of geometrical patterns, in order to automatically identify the objects.

2. The method according to claim 1 wherein during capture of the at least one image, the ear canal is illuminated from an eccentric illumination point positioned eccentrically within the ear canal.

3. The method according to claim 1, further comprising:
    using the electronic imaging unit to capture at least two images from different positions within the ear canal and/or with illumination from different positions within the ear canal; and
    comparing the at least two captured images with each other to identify objects shown in the images.

4. The method according to claim 3 wherein the at least two images are captured within a specific time frame.

5. The method of claim 4 wherein the at least two images are captured from at least two eccentric observation points.

6. The method of claim 3, further comprising using the electronic imaging unit to capture at least two images from different eccentric observation points within the ear canal and/or with illumination from different eccentric illumination points within the ear canal.

7. The method according to claim 1 wherein identifying objects comprises identifying the eardrum, the method further comprising medically characterizing the eardrum based on at least one image captured of the eardrum, wherein medically characterizing the eardrum includes determining the spectral composition of reflections of the eardrum and/or identifying objects within the tympanic cavity of the subject or determining a curvature of the eardrum or pressurizing the eardrum and detecting mobility of the eardrum.

8. The method of claim 7 wherein the curvature is a convexity.

9. The method of claim 1 wherein the distal direction is directed at the eardrum of the subject's ear and the objects include the eardrum.

10. The method of claim 1 wherein the identifying objects comprises pattern recognition of circular or ellipsoid shapes or geometrical patterns characterizing the malleus bone and pattern recognition is based on determination of an angle with respect to an inner lateral surface of the ear canal or a longitudinal axis of the ear canal.

11. The method of claim 1 wherein pattern recognition is based on determination of an angle or range of angles of the objects.

12. A method of identifying objects in a subject's ear, comprising:
    introducing an optical electronic imaging unit and at least one light source into an ear canal of a subject's outer ear, wherein the electronic imaging unit exhibits at least one optical axis directed in a distal direction;
    using the electronic imaging unit to capture at least one image from at least one eccentric observation point positioned on the at least one optical axis and positioned eccentrically within the ear canal;
    determining brightness or color information to identify objects shown in the at least one image by an electronic system using pattern recognition of geometrical patterns, in order to automatically identify the objects;
    using the electronic imaging unit to capture at least two images from different positions within the ear canal and/or with illumination from different positions within the ear canal; and
    comparing the at least two captured images with each other to identify objects shown in the images;
    wherein the different positions are defined or adjusted such that the captured images allow for stereoscopic viewing, the different positions being spaced apart from each other in a distance of at least 2 mm.

13. The method of claim 12 wherein the different positions are spaced apart from each other in a distance of between 3.7 mm and 4.4 mm for a distance between the positions for capturing the images.

14. The method of claim 12 wherein the different positions are spaced apart from each other in a distance of between 3.7 mm and 4.6 mm for a distance between the positions for illumination.

15. A method of identifying objects in a subject's ear, comprising:
- introducing an optical electronic imaging unit and at least one light source into an ear canal of a subject's outer ear, wherein the electronic imaging unit exhibits at least one optical axis directed in a distal direction;
- using the electronic imaging unit to capture at least one image from at least one eccentric observation point positioned on the at least one optical axis and positioned eccentrically within the ear canal;
- determining brightness or color information to identify objects shown in the at least one image by an electronic system using pattern recognition of geometrical patterns, in order to automatically identify the objects;
- using the electronic imaging unit to capture at least two images from different positions within the ear canal and/or with illumination from different positions within the ear canal; and
- comparing the at least two captured images with each other to identify objects shown in the images;
- wherein during capture of the at least two images, illumination is sequentially switched on and off.

16. The method of claim 15 wherein the at least one light source is provided by an LED and illumination is synchronized with a shutter of the electronic imaging unit.

17. A method of identifying objects in a subject's ear, comprising:
- introducing an optical electronic imaging unit and at least one light source into an ear canal of a subject's outer ear, wherein the electronic imaging unit exhibits at least one optical axis directed in a distal direction;
- using the electronic imaging unit to capture at least one image from at least one eccentric observation point positioned on the at least one optical axis and positioned eccentrically within the ear canal;
- determining brightness or color information to identify objects shown in the at least one image by an electronic system using pattern recognition of geometrical patterns, in order to automatically identify the objects;
- using the electronic imaging unit to capture at least two images from different positions within the ear canal and/or with illumination from different positions within the ear canal;
- comparing the at least two captured images with each other to identify objects shown in the images; and
- discriminating different objects by comparing their positions in at least two images captured from different positions within the ear canal, or by comparing their appearance in at least two images captured with illumination from different positions within the ear canal.

18. The method of claim 17 wherein the different objects are the eardrum and artifacts.

19. A method of identifying objects in a subject's ear, comprising:
- introducing an optical electronic imaging unit and at least one light source into an ear canal of a subject's outer ear, wherein the electronic imaging unit exhibits at least one optical axis directed in a distal direction;
- using the electronic imaging unit to capture at least one image from at least one eccentric observation point positioned on the at least one optical axis and positioned eccentrically within the ear canal;
- determining brightness or color information to identify objects shown in the at least one image by an electronic system using pattern recognition of geometrical patterns, in order to automatically identify the objects;
- wherein the at least one optical axis of the electronic imaging unit or the at least one light source is displaced within the ear canal of the subject's outer ear along a predetermined path or by a predetermined distance between the moment of capturing a first image and the moment of capturing a second image.

20. A method of identifying objects in a subject's ear, comprising:
- introducing an optical electronic imaging unit and at least one light source into an ear canal of a subject's outer ear, wherein the electronic imaging unit exhibits at least one optical axis directed in a distal direction;
- using the electronic imaging unit to capture at least one image from at least one eccentric observation point positioned on the at least one optical axis and positioned eccentrically within the ear canal; and
- determining brightness or color information to identify objects shown in the at least one image by an electronic system using pattern recognition of geometrical patterns, in order to automatically identify the objects;
- wherein an otoscope is used to carry out the method, the otoscope comprising:
- a handle portion allowing a user to manipulate the otoscope during its application; and
- a head portion exhibiting a substantially tapering form extending along a longitudinal axis of the head portion, wherein the head portion has a proximal end adjacent to the handle portion and a smaller distal end configured to be introduced into the ear canal of the subject's outer ear,
- wherein the otoscope further comprises the electronic imaging unit positioned in the distal end of the head portion, the at least one optical axis being positioned radially offset from the longitudinal axis.

21. The method according to claim 20 wherein at least two images are captured using at least two cameras of the electronic imaging unit each defining an optical axis of the electronic imaging unit or using beams splitter optics defining at least two optical axes of the electronic imaging unit.

22. The method according to claim 21 wherein the electronic imaging unit or at least one optical axis or the at least one light source is rotated, the rotation being carried out by a motor.

23. The method of claim 21 wherein the beams splitter optics are used in conjunction with a single image sensor.

24. The method according to claim 22 wherein identifying objects comprises determining the distance of the objects within the ear canal during rotation or from at least two different eccentric observation points.

25. The method according to claim 22 wherein the at least one light source is rotated so as to maintain a predetermined distance with respect to the electronic imaging unit or the at least one optical axis, when the electronic imaging unit or the at least one optical axis is rotated.

26. The method of claim 22 wherein the electronic imaging unit or at least one optical axis or the at least one light source is rotated on a pitch circle having a maximum radial offset with respect to a diameter of a distal tip of the head portion and the rotation is carried out by a brushless motor of a motion mechanism.

27. The method according to claim 20 wherein the electronic imaging unit or the at least one optical axis or the at least one light source is tilted against an axis of rotation of the electronic imaging unit or against the longitudinal axis so as to be continuously directed to a predetermined point on the axis of rotation or the longitudinal axis, the predetermined point having a fixed distance to the electronic imaging unit.

28. The method according to claim 20, further comprising relatively moving at least a portion of a probe cover put over the head portion with respect to the electronic imaging unit or the at least one optical axis.

29. The method according to claim 28 wherein displacing the probe cover is carried out in dependence on displacement of the electronic imaging unit or the at least one optical axis or the at least one light source.

30. The method of claim 29 wherein the displacing the probe cover is carried out prior to the displacement.

31. The method of claim 28, further comprising relatively moving at least a portion of a probe cover put over the head portion with respect to the electronic imaging unit or the at least one optical axis by a probe cover moving mechanism which is arranged for axial motion.

32. The method according to claim 20 wherein capturing the at least one image is carried out with the distal end being positioned at a distance of at least 10 mm.

33. The method of claim 32 wherein capturing the at least one image is carried out with the distal tip being positioned at a distance of at least 10 mm to the eardrum.

34. The method of claim 32 wherein capturing the at least one image is carried out with the distal end being positioned at a distance of at least 15 mm to the eardrum.

35. The method according to claim 20 wherein during introduction of the at least one optical electronic imaging unit, a force exerted on the head portion is detected.

36. The method according to claim 35, wherein a user guidance is carried out based on specific values of detected forces, wherein forces are detected by a force detection system.

37. The method of claim 36 wherein the force detection system is coupled to a motion mechanism or to a moving mechanism for moving a probe cover arranged at the head portion.

38. The method of claim 35 wherein the force is exerted in the direction of the longitudinal axis.

39. The method of claim 20 wherein the otoscope comprises the electronic imaging unit positioned at a distal tip of the head portion.

40. The method of claim 20 wherein the radial offset is at least one quarter of the radial dimension of the distal end.

41. A method of identifying objects in a subject's ear, comprising:
    introducing an optical electronic imaging unit and at least one light source into an ear canal of a subject's outer ear, wherein the electronic imaging unit exhibits at least one optical axis directed in a distal direction;
    using the electronic imaging unit to capture at least one image from at least one eccentric observation point positioned on the at least one optical axis and positioned eccentrically within the ear canal;
    determining brightness or color information to identify objects shown in the at least one image by an electronic system using pattern recognition of geometrical patterns, in order to automatically identify the objects; and
    verifying appropriate positioning of the electronic imaging unit or the at least one optical axis based on the at least one captured image such that a user can be guided, wherein the user is informed by an instruction indicating an insertion depth of a handle portion of an otoscope used for carrying out the method, or by an instruction indicating a direction of rotation of the handle portion, or by an instruction indicating a tilting angle of the handle portion.

42. The method of claim 41 wherein verifying appropriate positioning of the electronic imaging unit or the at least one optical axis occurs during the introducing the electronic imaging unit and the instruction indicates a tilting angle of the handle portion with respect to a longitudinal axis of the ear canal.

* * * * *